(12) United States Patent
Giasolli et al.

(10) Patent No.: US 10,022,250 B2
(45) Date of Patent: Jul. 17, 2018

(54) DEPLOYMENT DEVICE FOR PLACEMENT OF MULTIPLE INTRALUMINAL SURGICAL STAPLES

(75) Inventors: Robert Giasolli, Orange, CA (US); Peter Schneider, Honolulu, HI (US)

(73) Assignee: Intact Vascular, Inc., Wayne, PA (US)

(*) Notice: Subject to any disclaimer, the term of this patent is extended or adjusted under 35 U.S.C. 154(b) by 391 days.

(21) Appl. No.: 13/179,458

(22) Filed: Jul. 8, 2011

(65) Prior Publication Data

US 2012/0035705 A1 Feb. 9, 2012

Related U.S. Application Data

(63) Continuation-in-part of application No. 13/118,388, filed on May 28, 2011, now abandoned, which is a (Continued)

(51) Int. Cl.
*A61F 2/89* (2013.01)
*A61F 2/86* (2013.01)
(Continued)

(52) U.S. Cl.
CPC .................. *A61F 2/86* (2013.01); *A61F 2/89* (2013.01); *A61F 2/844* (2013.01); *A61F 2/848* (2013.01);
(Continued)

(58) Field of Classification Search
CPC ..... A61F 2/82–2/945; A61F 2/95–2/97; A61F 2002/821–2002/91591; A61F 2002/9505–2002/9665
(Continued)

(56) References Cited

U.S. PATENT DOCUMENTS 3,221,746 A 12/1965 Noble
3,635,223 A 1/1972 Klieman
(Continued)

FOREIGN PATENT DOCUMENTS

AU 2008335140 11/2012
AU 2011274392 11/2013
(Continued)

OTHER PUBLICATIONS

Notice of Acceptance in Australian Patent Application No. 201127439, dated Nov. 14, 2013, including accepted (allowed) claims, 9 pages.
(Continued)

*Primary Examiner* — Victor Nguyen
*Assistant Examiner* — Jonathan Hollm
(74) *Attorney, Agent, or Firm* — Knobbe, Martens, Olson & Bear, LLP

(57) ABSTRACT

A system for delivering a surgical staple can include various components. The system may include an elongate body with a proximal end, a distal end, and a plurality of delivery platforms disposed adjacent the distal end. A sheath can move relative to the elongate body from a first position in which the distal end of the sheath is disposed distally of a distal-most distal delivery platform to a second position in which the distal end of the sheath is disposed proximally of at least one delivery platform. A plurality of intravascular tacks can be within the system with each disposed about a corresponding delivery platform.

29 Claims, 47 Drawing Sheets

Related U.S. Application Data continuation-in-part of application No. 12/790,819, filed on May 29, 2010, which is a continuation-in-part of application No. 12/483,193, filed on Jun. 11, 2009, now Pat. No. 8,128,677, and application No. 13/179,458, Jul. 8, 2011, which is a continuation-in-part of application No. 13/153,257, filed on Jun. 3, 2011, now Pat. No. 9,375,327, which is a continuation-in-part of application No. 12/790,819, filed on May 29, 2010, which is a continuation-in-part of application No. 12/483,193, filed on Jun. 11, 2009, now Pat. No. 8,128,677.

(60) Provisional application No. 61/362,650, filed on Jul. 8, 2010, provisional application No. 61/349,836, filed on May 29, 2010.

(51) Int. Cl.

| | |
|---|---|
| A61F 2/844 | (2013.01) |
| A61F 2/848 | (2013.01) |
| A61F 2/91 | (2013.01) |
| A61F 2/92 | (2013.01) |
| A61F 2/966 | (2013.01) |
| A61F 2/82 | (2013.01) |
| A61F 2/915 | (2013.01) |
| A61F 2/95 | (2013.01) |
| A61F 2/958 | (2013.01) |

(52) U.S. Cl.
CPC . *A61F 2/91* (2013.01); *A61F 2/92* (2013.01); *A61F 2/966* (2013.01); *A61F 2002/823* (2013.01); *A61F 2002/825* (2013.01); *A61F 2002/826* (2013.01); *A61F 2002/8483* (2013.01); *A61F 2002/9155* (2013.01); *A61F 2002/9517* (2013.01); *A61F 2002/9583* (2013.01); *A61F 2002/9665* (2013.01); *A61F 2220/0016* (2013.01); *A61F 2230/0065* (2013.01); *A61F 2250/0039* (2013.01); *A61F 2250/0062* (2013.01)

(58) Field of Classification Search
USPC ...................................... 623/1.11–1.12, 1.35
See application file for complete search history.

(56) References Cited

U.S. PATENT DOCUMENTS

| | | | |
|---|---|---|---|
| 4,292,974 A | 10/1981 | Fogarty et al. | |
| 4,446,867 A | 5/1984 | Leveen et al. | |
| 4,465,072 A | 8/1984 | Taheri | |
| 4,515,587 A | 5/1985 | Schiff | |
| 4,545,367 A | 10/1985 | Tucci | |
| 4,545,390 A | 10/1985 | Leary | |
| 4,552,127 A | 11/1985 | Schiff | |
| 4,576,591 A | 3/1986 | Kay et al. | |
| 4,589,412 A | 5/1986 | Kensey | |
| 4,641,654 A | 2/1987 | Samson et al. | |
| 4,651,738 A | 3/1987 | Demer et al. | |
| 4,687,465 A | 8/1987 | Prindle et al. | |
| 4,723,550 A | 2/1988 | Bales et al. | |
| 4,723,936 A | 2/1988 | Buchbinder et al. | |
| 4,723,938 A | 2/1988 | Goodin et al. | |
| 4,726,374 A | 2/1988 | Bales et al. | |
| 4,758,223 A | 7/1988 | Rydell | |
| 4,762,130 A | 8/1988 | Fogarty et al. | |
| 4,781,192 A | 11/1988 | Demer | |
| 4,784,636 A | 11/1988 | Rydell | |
| 4,846,174 A | 7/1989 | Willard et al. | |
| 4,848,342 A | 7/1989 | Kaltenbach | |
| RE33,166 E | 2/1990 | Samson | |
| 5,009,659 A | 4/1991 | Hamlin et al. | |
| 5,024,668 A | 6/1991 | Peters et al. | |
| 5,042,707 A | 8/1991 | Taheri | |
| 5,047,015 A | 9/1991 | Foote et al. | |
| 5,102,390 A | 4/1992 | Crittenden et al. | |
| 5,196,024 A | 3/1993 | Barath | |
| 5,201,757 A | 4/1993 | Heyn et al. | |
| 5,242,452 A | 9/1993 | Inoue | |
| 5,246,420 A | 9/1993 | Kraus et al. | |
| 5,250,029 A | 10/1993 | Lin et al. | |
| 5,250,060 A | 10/1993 | Carbo et al. | |
| 5,263,962 A | 11/1993 | Johnson et al. | |
| 5,269,758 A | 12/1993 | Taheri | |
| 5,304,121 A | 4/1994 | Sahatjian | |
| 5,318,529 A | 6/1994 | Kontos | |
| 5,336,234 A | 8/1994 | Virgil et al. | |
| 5,344,397 A | 9/1994 | Heaven et al. | |
| 5,383,890 A | 1/1995 | Miraki et al. | |
| 5,397,305 A | 3/1995 | Kawula et al. | |
| 5,397,355 A | 3/1995 | Marin et al. | |
| 5,421,955 A | 6/1995 | Lau et al. | |
| 5,423,851 A | 6/1995 | Samuels | |
| 5,423,885 A | 6/1995 | Williams | |
| 5,501,689 A | 3/1996 | Green et al. | |
| 5,534,007 A | 7/1996 | St. Germain et al. | |
| 5,536,252 A | 7/1996 | Imran et al. | |
| 5,540,659 A | 7/1996 | Teirstein | |
| 5,545,135 A | 8/1996 | Iacob et al. | |
| 5,562,728 A | 10/1996 | Lazarus et al. | |
| 5,569,272 A | 10/1996 | Reed et al. | |
| 5,571,135 A | 11/1996 | Fraser et al. | |
| 5,591,197 A | 1/1997 | Orth et al. | |
| 5,593,417 A | 1/1997 | Rhodes | |
| 5,616,149 A | 4/1997 | Barath | |
| 5,643,312 A | 7/1997 | Fischell et al. | |
| 5,665,116 A | 9/1997 | Chaisson et al. | |
| 5,681,346 A | 10/1997 | Orth et al. | |
| 5,704,913 A | 1/1998 | Abele et al. | |
| 5,725,572 A * | 3/1998 | Lam et al. | 623/1.16 |
| 5,728,158 A | 3/1998 | Lau et al. | |
| 5,746,716 A | 5/1998 | Vigil et al. | |
| 5,746,764 A | 5/1998 | Green et al. | |
| 5,776,161 A | 7/1998 | Globerman | |
| 5,797,951 A | 8/1998 | Mueller | |
| 5,800,526 A | 9/1998 | Anderson et al. | |
| 5,813,977 A | 9/1998 | Hinchliffe et al. | |
| 5,817,152 A * | 10/1998 | Birdsall et al. | 623/1.16 |
| 5,833,694 A * | 11/1998 | Poncet | A61F 2/95 623/1.11 |
| 5,843,033 A | 12/1998 | Ropiak | |
| 5,911,725 A | 6/1999 | Boury | |
| 5,925,061 A | 7/1999 | Ogi et al. | |
| 5,928,247 A | 7/1999 | Barry et al. | |
| 5,954,742 A | 9/1999 | Osypka | |
| 5,957,949 A | 9/1999 | Leonhardt et al. | |
| 5,968,068 A | 10/1999 | Dehdashtian et al. | |
| 5,968,088 A * | 10/1999 | Hansen et al. | 623/1.12 |
| 5,972,023 A | 10/1999 | Tanner et al. | |
| 5,980,552 A | 11/1999 | Pinchasik et al. | |
| 6,004,328 A | 12/1999 | Solar | |
| 6,007,543 A | 12/1999 | Ellis et al. | |
| 6,009,614 A | 1/2000 | Morales | |
| 6,013,854 A | 1/2000 | Moriuchi | |
| 6,036,725 A | 3/2000 | Avellanet | |
| 6,048,360 A | 4/2000 | Khosravi et al. | |
| 6,053,941 A | 4/2000 | Lindenberg et al. | |
| 6,053,943 A | 4/2000 | Edwin et al. | |
| 6,080,177 A | 6/2000 | Igaki | |
| 6,090,135 A | 7/2000 | Plaia et al. | |
| 6,110,198 A | 8/2000 | Fogarty et al. | |
| 6,123,722 A | 9/2000 | Fogarty et al. | |
| 6,126,685 A | 10/2000 | Lenker et al. | |
| 6,129,754 A | 10/2000 | Kanesaka et al. | |
| 6,139,573 A | 10/2000 | Sogard et al. | |
| 6,143,016 A | 11/2000 | Bleam et al. | |
| 6,146,358 A | 11/2000 | Rowe | |
| 6,152,937 A | 11/2000 | Peterson et al. | |
| 6,157,852 A | 12/2000 | Selmon et al. | |
| 6,165,199 A | 12/2000 | Barbut | |
| 6,187,034 B1 | 2/2001 | Frantzen | |

(56) References Cited

U.S. PATENT DOCUMENTS

| | | |
|---|---|---|
| 6,197,013 B1 | 3/2001 | Reed |
| 6,197,103 B1 | 3/2001 | Davies et al. |
| 6,203,568 B1 | 3/2001 | Lombardi et al. |
| 6,203,569 B1 | 3/2001 | Wijay |
| 6,221,102 B1 | 4/2001 | Baker et al. |
| 6,241,667 B1 | 6/2001 | Vetter et al. |
| 6,254,628 B1 | 7/2001 | Wallace et al. |
| 6,258,117 B1 | 7/2001 | Camrud et al. |
| 6,266,550 B1 | 7/2001 | Selmon et al. |
| 6,270,524 B1 | 8/2001 | Kim |
| 6,273,909 B1 | 8/2001 | Kugler et al. |
| 6,290,728 B1 | 9/2001 | Phelps et al. |
| 6,312,444 B1 | 11/2001 | Barbut |
| 6,312,460 B2 | 11/2001 | Drasler et al. |
| 6,325,824 B2 | 12/2001 | Limon |
| 6,364,901 B1 | 4/2002 | Inoue |
| 6,364,904 B1 | 4/2002 | Smith |
| 6,371,962 B1 | 4/2002 | Ellis et al. |
| 6,387,113 B1 | 5/2002 | Hawkins et al. |
| 6,409,863 B1 | 6/2002 | Williams et al. |
| 6,425,915 B1 | 7/2002 | Khosravi et al. |
| 6,428,550 B1 | 8/2002 | Vargas et al. |
| 6,428,566 B1 | 8/2002 | Holt |
| 6,475,237 B2 | 11/2002 | Drasler et al. |
| 6,485,510 B1 | 11/2002 | Camrud et al. |
| 6,491,707 B2 | 12/2002 | Makower et al. |
| 6,508,822 B1 | 1/2003 | Peterson et al. |
| 6,517,573 B1 | 2/2003 | Pollock et al. |
| 6,547,817 B1 | 4/2003 | Fischell et al. |
| 6,551,353 B1 | 4/2003 | Baker et al. |
| 6,648,911 B1 | 11/2003 | Sirhan et al. |
| 6,660,031 B2 | 12/2003 | Tran et al. |
| 6,692,504 B2 | 2/2004 | Kurz et al. |
| 6,699,277 B1 | 3/2004 | Freidberg et al. |
| 6,706,061 B1 | 3/2004 | Fischell et al. |
| 6,716,240 B2 | 4/2004 | Fischell et al. |
| 6,719,775 B2 | 4/2004 | Slaker et al. |
| 6,730,116 B1 | 5/2004 | Wolinsky et al. |
| 6,746,475 B1 | 6/2004 | Rivelli, Jr. |
| 6,752,828 B2 | 6/2004 | Thornton |
| 6,786,922 B2 | 9/2004 | Schaeffer |
| 6,790,221 B2 | 9/2004 | Monroe et al. |
| 6,790,227 B2 | 9/2004 | Burgermeister |
| 6,810,882 B2 | 11/2004 | Langberg et al. |
| 6,814,752 B1 | 11/2004 | Chuter |
| 6,827,731 B2 | 12/2004 | Armstrong et al. |
| 6,843,400 B1 | 1/2005 | Lee |
| 6,849,087 B1 | 2/2005 | Chuter |
| 6,896,697 B1 | 5/2005 | Yip et al. |
| 6,899,718 B2 | 5/2005 | Gifford, III et al. |
| 6,913,600 B2 | 7/2005 | Valley et al. |
| 6,942,680 B2 | 9/2005 | Grayzel et al. |
| 6,951,554 B2 | 10/2005 | Johansen et al. |
| 6,986,784 B1 | 1/2006 | Weiser et al. |
| 7,001,422 B2 | 2/2006 | Escamilla et al. |
| 7,001,424 B2 | 2/2006 | Patel et al. |
| 7,007,698 B2 | 3/2006 | Thornton |
| 7,018,402 B2 | 3/2006 | Vito et al. |
| 7,025,791 B2 | 4/2006 | Levine et al. |
| 7,037,330 B1 | 5/2006 | Rivelli, Jr. et al. |
| 7,041,130 B2 | 5/2006 | Santini, Jr. et al. |
| 7,087,088 B2 | 8/2006 | Berg et al. |
| 7,122,043 B2 | 10/2006 | Greenhalgh et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,147,661 B2 | 12/2006 | Chobotov et al. |
| 7,150,745 B2 | 12/2006 | Stern et al. |
| 7,160,312 B2 | 1/2007 | Saadat |
| 7,163,552 B2 | 1/2007 | Diaz |
| 7,166,125 B1 | 1/2007 | Baker et al. |
| 7,169,158 B2 | 1/2007 | Sniffin et al. |
| 7,169,163 B2 | 1/2007 | Becker |
| 7,179,284 B2 | 2/2007 | Khosravi et al. |
| 7,201,770 B2 | 4/2007 | Johnson et al. |
| 7,211,101 B2 | 5/2007 | Carley et al. |
| 7,258,697 B1 | 8/2007 | Cox et al. |
| 7,261,731 B2 | 8/2007 | Patel et al. |
| 7,270,673 B2 | 9/2007 | Yee et al. |
| 7,273,492 B2 | 9/2007 | Cheng et al. |
| 7,279,007 B2 | 10/2007 | Nikolic et al. |
| 7,294,146 B2 | 11/2007 | Chew et al. |
| 7,296,577 B2 | 11/2007 | Lashinski et al. |
| 7,300,456 B2 | 11/2007 | Andreas et al. |
| 7,303,572 B2 | 12/2007 | Meisheimer et al. |
| 7,306,617 B2 | 12/2007 | Majercak |
| 7,309,341 B2 | 12/2007 | Ortiz et al. |
| 7,309,350 B2 | 12/2007 | Landreville et al. |
| 7,323,006 B2 | 1/2008 | Andreas et al. |
| 7,323,007 B2 | 1/2008 | Sano |
| 7,326,236 B2 | 2/2008 | Andreas et al. |
| 7,329,279 B2 | 2/2008 | Haug et al. |
| 7,331,987 B1 | 2/2008 | Cox |
| 7,331,992 B2 | 2/2008 | Randall et al. |
| 7,351,255 B2 | 4/2008 | Andreas |
| 7,399,307 B2 | 7/2008 | Evans et al. |
| 7,402,168 B2 | 7/2008 | Sanderson et al. |
| 7,431,729 B2 | 10/2008 | Chanduszko |
| 7,445,631 B2 | 11/2008 | Salaheih et al. |
| 7,476,245 B2 | 1/2009 | Abbate |
| 7,500,986 B2 | 3/2009 | Lye et al. |
| 7,510,575 B2 | 3/2009 | Spenser et al. |
| 7,524,330 B2 | 4/2009 | Berreklouw |
| 7,537,607 B2 | 5/2009 | Gerberding |
| 7,617,007 B2 | 11/2009 | Williams et al. |
| 7,618,432 B2 | 11/2009 | Pedersen et al. |
| 7,655,034 B2 | 2/2010 | Mitchell et al. |
| 7,666,216 B2 | 2/2010 | Hogendijk et al. |
| 7,695,507 B2 | 4/2010 | Rivelli, Jr. et al. |
| 7,720,521 B2 | 5/2010 | Chang et al. |
| 7,736,387 B2 | 6/2010 | Pollock et al. |
| 7,758,632 B2 | 7/2010 | Hojeibane et al. |
| 7,763,063 B2 | 7/2010 | Arbefeuille et al. |
| 7,806,918 B2 | 10/2010 | Nissl et al. |
| 7,833,262 B2 | 11/2010 | McGuckin, Jr. et al. |
| 7,842,080 B2 | 11/2010 | Chouinard |
| 7,846,194 B2 | 12/2010 | Hartley et al. |
| 7,867,267 B2 | 1/2011 | Sullivan et al. |
| 7,871,431 B2 | 1/2011 | Gurm et al. |
| 7,883,537 B2 | 2/2011 | Grayzel et al. |
| 7,896,911 B2 | 3/2011 | Schneider et al. |
| 7,905,913 B2 | 3/2011 | Chew et al. |
| 7,922,755 B2 | 4/2011 | Acosta et al. |
| 7,933,660 B2 | 4/2011 | Carr |
| 7,955,315 B2 | 6/2011 | Feinberg et al. |
| 7,963,987 B2 | 6/2011 | Melsheimer et al. |
| 7,967,855 B2 | 6/2011 | Furst et al. |
| 7,972,373 B2 | 7/2011 | Contiliano et al. |
| 8,002,725 B2 | 8/2011 | Hogendijk |
| 8,024,851 B2 | 9/2011 | Barr et al. |
| 8,043,354 B2 | 10/2011 | Greenberg et al. |
| 8,048,151 B2 | 11/2011 | O'Brien et al. |
| 8,052,738 B2 | 11/2011 | Craven |
| 8,128,677 B2 | 3/2012 | Giasolli et al. |
| 8,177,831 B2 | 5/2012 | Andreas |
| 8,236,045 B2 | 8/2012 | Benichou et al. |
| 8,292,938 B2 | 10/2012 | Case |
| 8,308,790 B2 | 11/2012 | Arbefeuille et al. |
| 8,323,243 B2 | 12/2012 | Schneider et al. |
| 8,366,766 B2 | 2/2013 | Berreklouw |
| 8,414,636 B2 | 4/2013 | Nabulsi et al. |
| 8,474,460 B2 | 7/2013 | Barrett et al. |
| 8,500,787 B2 | 8/2013 | Simpson et al. |
| 8,500,789 B2 | 8/2013 | Wuebbeling et al. |
| 8,585,747 B2 | 11/2013 | Andreas et al. |
| 8,784,467 B2 | 7/2014 | Connelly et al. |
| 8,888,841 B2 | 11/2014 | Pandelidis et al. |
| 8,900,289 B2 | 12/2014 | Thompson |
| 8,956,398 B2 | 2/2015 | George et al. |
| 8,986,362 B2 | 3/2015 | Snow et al. |
| 9,050,181 B2 | 6/2015 | Hartley |
| 9,101,503 B2 | 8/2015 | Lowe et al. |
| 9,113,999 B2 | 8/2015 | Taylor et al. |
| 9,216,082 B2 | 12/2015 | Von Segesser et al. |

(56) References Cited

U.S. PATENT DOCUMENTS

| | | |
|---|---|---|
| 9,237,959 B2 | 1/2016 | Cage |
| 9,370,437 B2 | 6/2016 | Chuter et al. |
| 9,375,327 B2 | 6/2016 | Giasolli et al. |
| 9,398,967 B2 | 7/2016 | Cornelius |
| 9,480,826 B2 | 11/2016 | Schneider et al. |
| 9,603,730 B2 | 3/2017 | Giasolli et al. |
| 2002/0007211 A1 | 1/2002 | Pinchasik et al. |
| 2002/0055772 A1 | 5/2002 | McGuckin, Jr. et al. |
| 2002/0120323 A1 | 8/2002 | Thompson |
| 2002/0123790 A1 | 9/2002 | White et al. |
| 2002/0143386 A1 | 10/2002 | Davila et al. |
| 2002/0151955 A1* | 10/2002 | Tran et al. .................. 623/1.12 |
| 2002/0156496 A1* | 10/2002 | Chermoni .................. 606/194 |
| 2002/0169495 A1 | 11/2002 | Gifford et al. |
| 2003/0018377 A1* | 1/2003 | Berg et al. .................. 623/1.11 |
| 2003/0055491 A1 | 3/2003 | Schwartz et al. |
| 2003/0069630 A1 | 4/2003 | Burgermeister et al. |
| 2003/0130720 A1 | 7/2003 | DePalma |
| 2003/0220683 A1 | 11/2003 | Minasian et al. |
| 2003/0225446 A1 | 12/2003 | Hartley |
| 2003/0225448 A1 | 12/2003 | Gerberding |
| 2004/0010307 A1 | 1/2004 | Grad et al. |
| 2004/0098077 A1 | 5/2004 | Gianotti |
| 2004/0143287 A1 | 7/2004 | Konstantino et al. |
| 2004/0158308 A1* | 8/2004 | Hogendijk et al. .......... 623/1.11 |
| 2004/0186551 A1 | 9/2004 | Kao et al. |
| 2004/0215324 A1 | 10/2004 | Vonderwalde et al. |
| 2004/0215326 A1 | 10/2004 | Goodson, IV et al. |
| 2004/0230291 A1 | 11/2004 | Richter |
| 2004/0230293 A1 | 11/2004 | Yip |
| 2004/0267348 A1 | 12/2004 | Gunderson et al. |
| 2005/0010275 A1 | 1/2005 | Sahatjian et al. |
| 2005/0096727 A1 | 5/2005 | Allen et al. |
| 2005/0131525 A1 | 6/2005 | Hartley |
| 2005/0149163 A1 | 7/2005 | Sahota |
| 2005/0171592 A1* | 8/2005 | Majercak .................. 623/1.11 |
| 2005/0172471 A1 | 8/2005 | Vietmeier |
| 2005/0222670 A1 | 10/2005 | Schaeffer |
| 2005/0228485 A1 | 10/2005 | Rolando et al. |
| 2005/0246008 A1 | 11/2005 | Hogendijk et al. |
| 2005/0251164 A1 | 11/2005 | Gifford, III et al. |
| 2005/0288764 A1* | 12/2005 | Snow et al. .................. 623/1.11 |
| 2005/0288766 A1 | 12/2005 | Plain et al. |
| 2006/0069424 A1 | 3/2006 | Acosta et al. |
| 2006/0074478 A1 | 4/2006 | Feller, III |
| 2006/0095113 A1 | 5/2006 | Niermann |
| 2006/0111769 A1 | 5/2006 | Murray |
| 2006/0149349 A1 | 7/2006 | Garbe |
| 2006/0184225 A1* | 8/2006 | Pryor .................. 623/1.11 |
| 2006/0184227 A1* | 8/2006 | Rust .................. A61F 2/07 623/1.13 |
| 2006/0193892 A1 | 8/2006 | Furst et al. |
| 2006/0200231 A1 | 9/2006 | O'Brien et al. |
| 2006/0206190 A1* | 9/2006 | Chermoni .................. 623/1.11 |
| 2006/0229700 A1* | 10/2006 | Acosta et al. .................. 623/1.11 |
| 2006/0248698 A1 | 11/2006 | Hanson et al. |
| 2006/0271151 A1 | 11/2006 | McGarry et al. |
| 2006/0276871 A1 | 12/2006 | Lamson et al. |
| 2006/0282147 A1 | 12/2006 | Andreas |
| 2006/0282149 A1 | 12/2006 | Kao |
| 2007/0021826 A1* | 1/2007 | Case .................. A61F 2/2418 623/1.15 |
| 2007/0088420 A1 | 4/2007 | Andreas et al. |
| 2007/0093744 A1 | 4/2007 | Elmaleh |
| 2007/0156223 A1* | 7/2007 | Vaughan .................. 623/1.11 |
| 2007/0156225 A1* | 7/2007 | George et al. .................. 623/1.12 |
| 2007/0179587 A1 | 8/2007 | Acosta et al. |
| 2007/0191926 A1 | 8/2007 | Nikanorov et al. |
| 2007/0255391 A1 | 11/2007 | Hojeibane et al. |
| 2007/0276461 A1 | 11/2007 | Andreas et al. |
| 2008/0033522 A1 | 2/2008 | Grewe et al. |
| 2008/0051867 A1 | 2/2008 | Davila et al. |
| 2008/0077229 A1 | 3/2008 | Andres et al. |
| 2008/0082154 A1 | 4/2008 | Tseng et al. |
| 2008/0132989 A1 | 6/2008 | Snow et al. |
| 2008/0132999 A1 | 6/2008 | Mericle |
| 2008/0208327 A1 | 8/2008 | Rowe |
| 2008/0221658 A1 | 9/2008 | Martin et al. |
| 2008/0255653 A1 | 10/2008 | Schkolnik |
| 2008/0264102 A1 | 10/2008 | Berra |
| 2008/0319528 A1 | 12/2008 | Yribarren et al. |
| 2009/0018637 A1 | 1/2009 | Paul, Jr. et al. |
| 2009/0018645 A1 | 1/2009 | Cambronne et al. |
| 2009/0076594 A1 | 3/2009 | Sabaria |
| 2009/0082841 A1 | 3/2009 | Zacharias et al. |
| 2009/0149943 A1 | 6/2009 | Tower |
| 2009/0171427 A1* | 7/2009 | Melsheimer et al. ....... 623/1.11 |
| 2009/0214615 A1 | 8/2009 | Zhao |
| 2009/0216284 A1 | 8/2009 | Chin et al. |
| 2009/0248141 A1 | 10/2009 | Shandas et al. |
| 2009/0270965 A1 | 10/2009 | Sinha et al. |
| 2009/0270967 A1 | 10/2009 | Fleming, III et al. |
| 2009/0276031 A1 | 11/2009 | Kao |
| 2010/0131045 A1 | 5/2010 | Globerman et al. |
| 2010/0137966 A1* | 6/2010 | Magnuson .................. 623/1.11 |
| 2010/0298921 A1 | 11/2010 | Schlun et al. |
| 2010/0318173 A1* | 12/2010 | Kolandaivelu et al. ..... 623/1.11 |
| 2011/0004237 A1 | 1/2011 | Schneider et al. |
| 2011/0077731 A1 | 3/2011 | Lee et al. |
| 2011/0152992 A1 | 6/2011 | Schneider et al. |
| 2011/0230954 A1 | 9/2011 | Schneider et al. |
| 2011/0301685 A1 | 12/2011 | Kao |
| 2011/0301690 A1 | 12/2011 | Giasolli et al. |
| 2011/0307049 A1 | 12/2011 | Kao |
| 2012/0016457 A1 | 1/2012 | Chobotov et al. |
| 2012/0035705 A1 | 2/2012 | Giasolli et al. |
| 2012/0083872 A1 | 4/2012 | Schneider et al. |
| 2012/0191176 A1 | 7/2012 | Nagl et al. |
| 2013/0144375 A1 | 6/2013 | Giasolli et al. |
| 2014/0194967 A1 | 7/2014 | Schneider et al. |
| 2014/0288629 A1 | 9/2014 | Amendt et al. |
| 2017/0000629 A1 | 1/2017 | Giasolli et al. |
| 2017/0181873 A1 | 6/2017 | Schneider et al. |
| 2017/0296366 A1 | 10/2017 | Giasolli et al. |
| 2017/0319361 A1 | 11/2017 | Giasolli et al. |
| 2017/0319364 A1 | 11/2017 | Jung et al. |

FOREIGN PATENT DOCUMENTS

| | | |
|---|---|---|
| AU | 2014201067 | 3/2014 |
| AU | 2010259907 | 8/2015 |
| AU | 2013212056 | 7/2016 |
| AU | 2015207895 | 5/2017 |
| AU | 2014280976 | 7/2017 |
| CA | 2705275 | 7/2013 |
| CN | 101262835 | 9/2008 |
| CN | 101754727 | 6/2010 |
| CN | 102724931 | 10/2012 |
| CN | 104887365 | 9/2015 |
| CN | 103313682 | 8/2016 |
| CN | 104220026 | 9/2016 |
| CN | 106466205 | 3/2017 |
| CN | 106473786 | 3/2017 |
| CN | 106473849 | 3/2017 |
| CN | 107028691 | 8/2017 |
| CN | 107157632 | 9/2017 |
| CN | 107205834 | 9/2017 |
| CN | 104887365 | 12/2017 |
| DE | 60030705 T2 | 5/2007 |
| DE | 10 2009 041 025 | 3/2011 |
| DE | 202011107781 | 12/2011 |
| DE | 20 2011 110 714 | 12/2015 |
| DE | 102014016588 | 5/2016 |
| DE | 20 2011 110 818 | 9/2016 |
| DK | 2775968 | 12/2017 |
| EP | 0497620 | 8/1992 |
| EP | 0714640 | 6/1996 |
| EP | 0855883 | 8/1998 |
| EP | 0812580 | 2/2004 |
| EP | 1393766 | 3/2004 |
| EP | 1803423 | 7/2007 |
| EP | 1894545 | 3/2008 |
| EP | 2219535 | 8/2010 |
| EP | 2440155 | 4/2012 |

(56) References Cited

FOREIGN PATENT DOCUMENTS

| | | |
|---|---|---|
| EP | 2775968 | 9/2014 |
| EP | 2806826 | 12/2014 |
| EP | 2881086 | 6/2015 |
| EP | 2699207 | 10/2015 |
| EP | 2590602 | 12/2015 |
| EP | 3015078 | 5/2016 |
| EP | 3058900 | 8/2016 |
| EP | 3072463 | 9/2016 |
| EP | 2775968 | 9/2017 |
| EP | 3217927 | 9/2017 |
| FR | 2714816 | 7/1995 |
| GB | 201106757 | 6/2011 |
| JP | H11-501526 | 2/1999 |
| JP | H11-506665 | 6/1999 |
| JP | 2007-503923 | 3/2007 |
| JP | 2008-504078 | 2/2008 |
| JP | 2008-246214 | 10/2008 |
| JP | 2008-537891 | 10/2008 |
| JP | 2016-135278 | 7/2016 |
| JP | 6006808 | 10/2016 |
| KR | 2017084214 | 7/2017 |
| WO | WO 96/09013 | 3/1996 |
| WO | WO 1996/037167 | 11/1996 |
| WO | WO 1999/048440 | 9/1999 |
| WO | WO 1999/049440 | 9/1999 |
| WO | WO 2000/066034 | 11/2000 |
| WO | WO 2001/076509 | 10/2001 |
| WO | WO 03/047651 | 6/2003 |
| WO | WO 03/101310 | 12/2003 |
| WO | WO 2004/006983 | 1/2004 |
| WO | WO 2004/032799 | 4/2004 |
| WO | WO 2006/026371 | 3/2006 |
| WO | WO 2007/088549 | 8/2007 |
| WO | WO 2007/109621 | 9/2007 |
| WO | WO 2009/076517 | 6/2009 |
| WO | WO 2010/037141 | 4/2010 |
| WO | WO 2010/118432 | 10/2010 |
| WO | WO 2010/144845 | 12/2010 |
| WO | WO 2011/153110 | 12/2011 |
| WO | WO 2012/006602 | 1/2012 |
| WO | WO 2012/143731 | 10/2012 |
| WO | WO 2013/068127 | 5/2013 |
| WO | WO 2013/112768 | 8/2013 |
| WO | WO 2016/074799 | 5/2016 |

OTHER PUBLICATIONS

Patent Examination Report No. 1 in Australian Patent Application No. 201127439, issued May 3, 2013, 3 pages.
International Search Report and Written Opinion for International Application No. PCT/US2011/043471 dated Feb. 9, 2012.
Supplementary European Search Report for European Application No. EP11804455.1 dated Jun. 11, 2014.
International Search Report and Written Opinion for International Application No. PCT/US2013/023030, Notification dated Apr. 16, 2013.
Colombo, A. et al., "Intravascular Ultrasound-Guided Percutaneous Transluminal Coronary Angioplasty With Provisional Spot Stenting for Treatment of Long Coronary Lesions", Journal of the American College of Cardiology, vol. 38, No. 5, Nov. 1, 2001, in 9 pages.
Mosseri, M. et al., "New Indicator for Stent Covering Area", in Catheterization and Cardiovascular Diagnosis, 1998, vol. 44, in 5 pages.
Australian Office Action, re AU Application No. 2008335140, dated Apr. 21, 2011.
Australian Office Action, re AU Application No. 2008335140, dated Mar. 15, 2011.
European Office Action and Supplementary Partial European Search Report, re EP Application No. 08858824.9, dated Sep. 27, 2012.
International Search Report and Written Opinion, re PCT Application No. PCT/US2010/038379, dated Feb. 25, 2011.
International Search Report and Written Opinion, re PCT Application No. PCT/US2011/038468, dated Jan. 18, 2012.
International Search Report and Written Opinion, re PCT Application PCT/US2008/086396, dated Jul. 27, 2009.
International Search Report, re PCT Application No. PCT/US2013/023030, dated Apr. 16, 2013.
Bosiers, M. et al., "Results from the Tack Optimized Balloon Angioplasty (TOBA) study demonstrate the benefits of minimal metal implants for dissection repair after angioplasty", Journal of Vascular Surgery, vol. 64, Jul. 2016, in 8 pages.
Kokkinidis, D. et al., "Emerging and Future Therapeutic Options for Femoropopliteal and Infrapopliteal Endovascular Intervention", Interventional Cardiology Clinics, vol. 6, 2017, in 17 pages.
Shishehbor, M. et al., "Endovascular Treatment of Femoropopliteal Lesions", Journal of the American College of Cardiology, vol. 66, 2015, in 4 pages.
Zeller, T. et al., "Novel Approaches to the Management of Advanced Peripheral Artery Disease: Perspectives on Drug-Coated Balloons, Drug-Eluting Stents, and Bioresorbable Scaffolds", Current Cardiology Reports, vol. 17, Sep. 2015, in 6 pages.
International Preliminary Report on Patentability, re PCT Application No. PCT/US2008/086396, dated Jun. 15, 2010.
International Preliminary Report on Patentability, re PCT Application No. PCT/US2011/038468, dated Dec. 13, 2012.
International Preliminary Report on Patentability, re PCT Application No. PCT/US2011/043471, dated Jan. 17, 2013.
International Preliminary Report on Patentability, re PCT Application No. PCT/US2013/023030, dated Aug. 7, 2014.
Office Action dated Jan. 1, 2018 in Australian Patent No. 2016247190 in 5 pages.
English translation of the first Office Action and Search Report in Chinese Application No. 201610546800.2 in 5 pages dated Sep. 28, 2017.
English translation of the first Office Action and Search Report in Chinese Application No. 201610546643.5 in 5 pages dated Oct. 17, 2017.

* cited by examiner

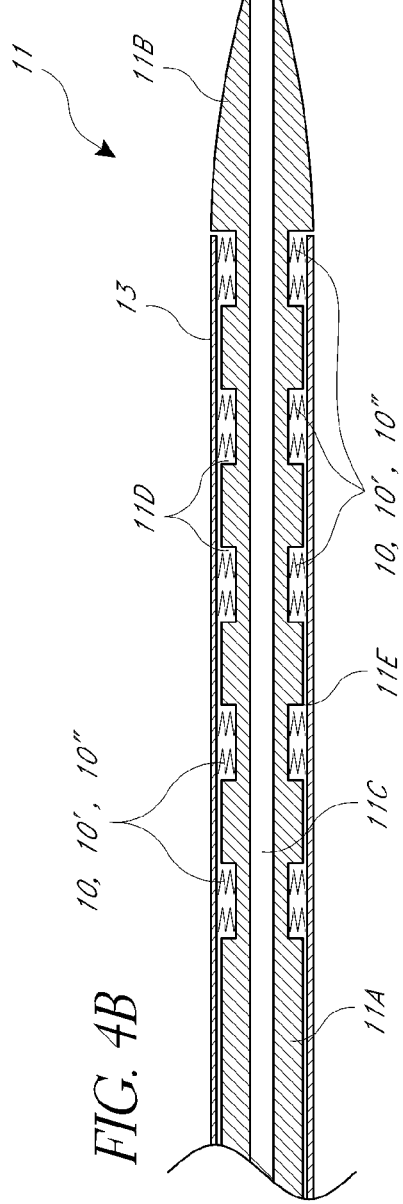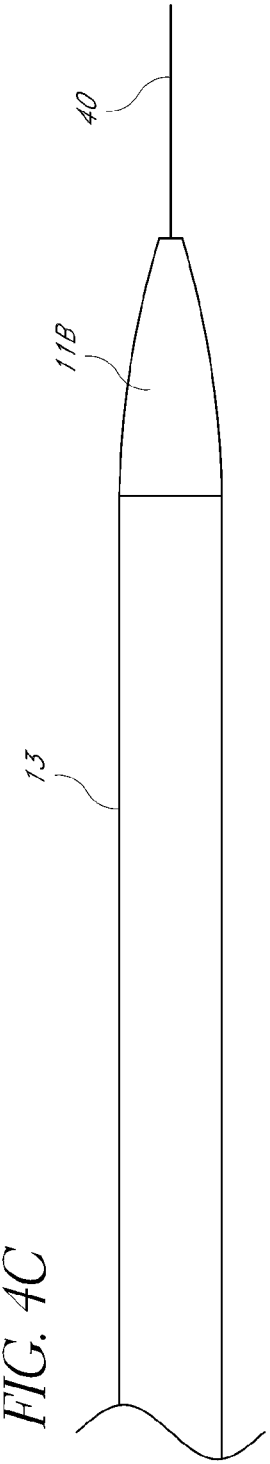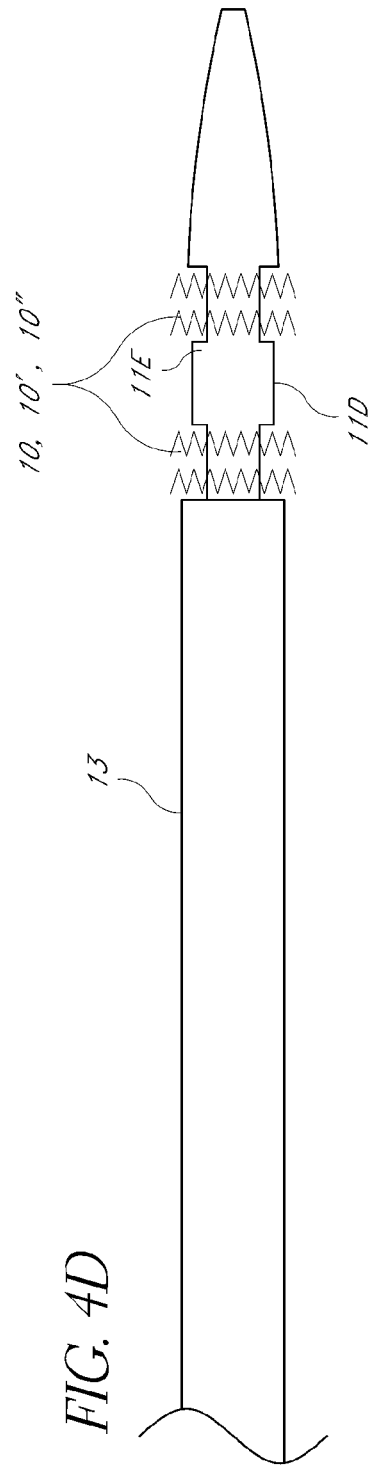
FIG. 4B
FIG. 4C
FIG. 4D

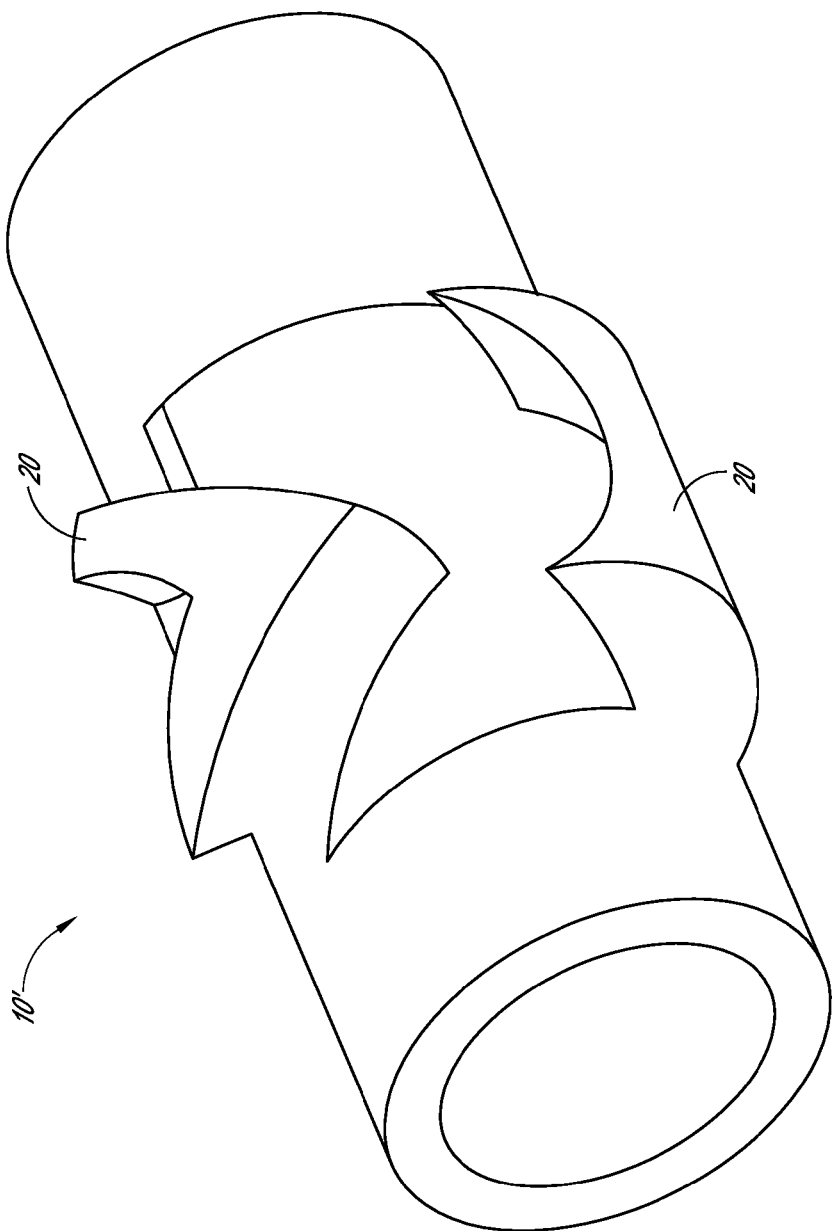
FIG. 5C1

FEE

FEE

FEE

FEE

FEE

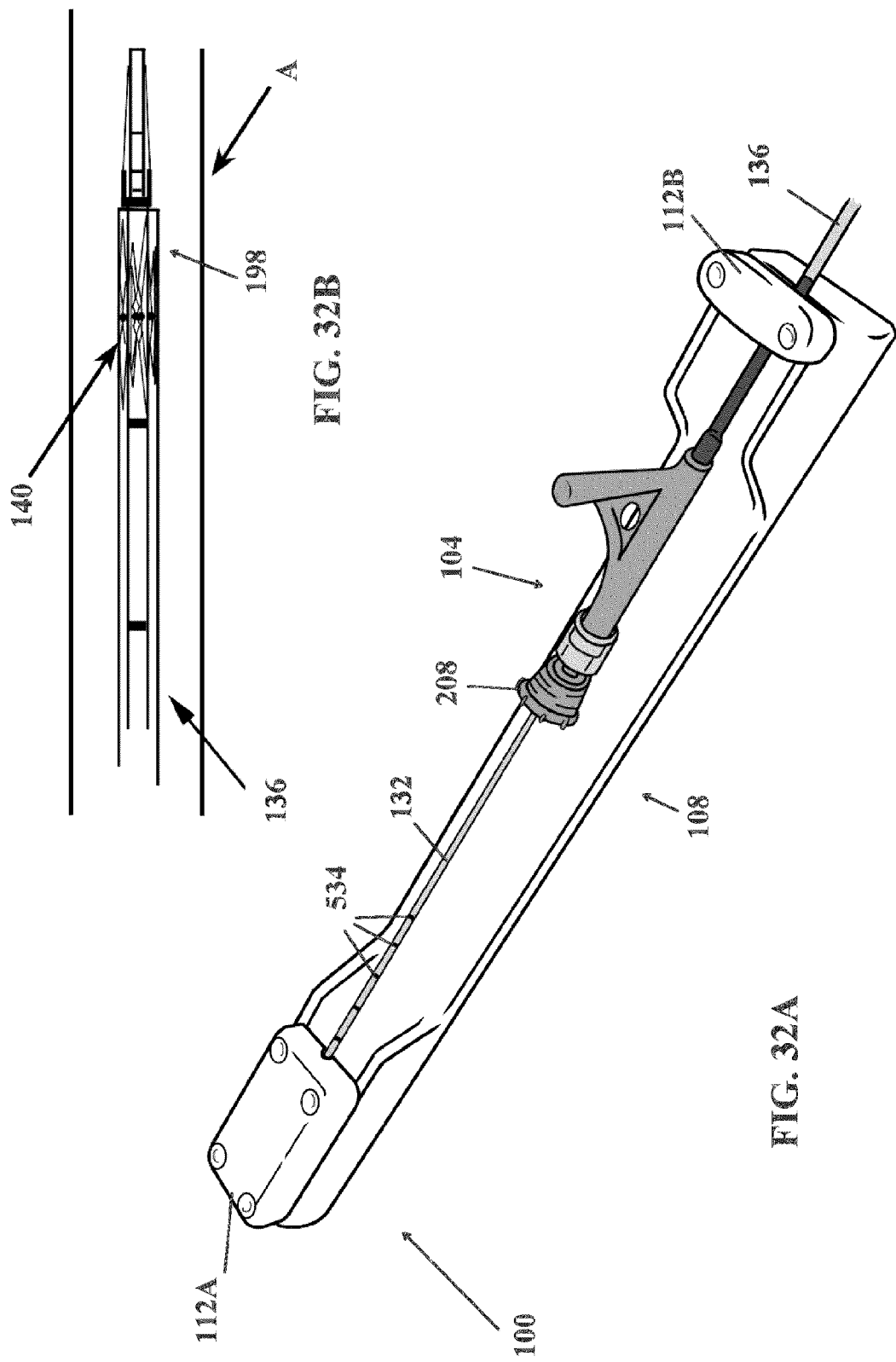

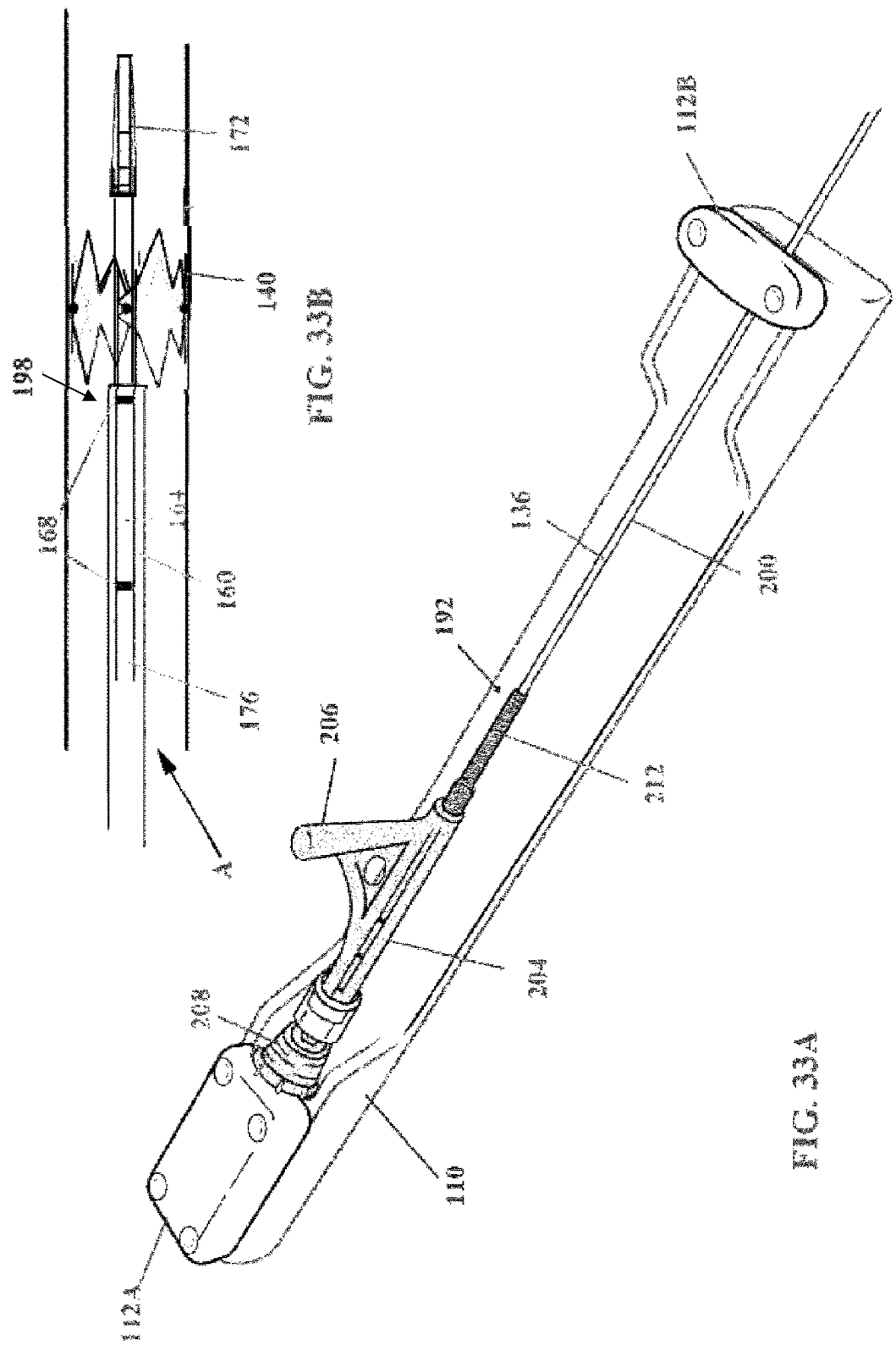

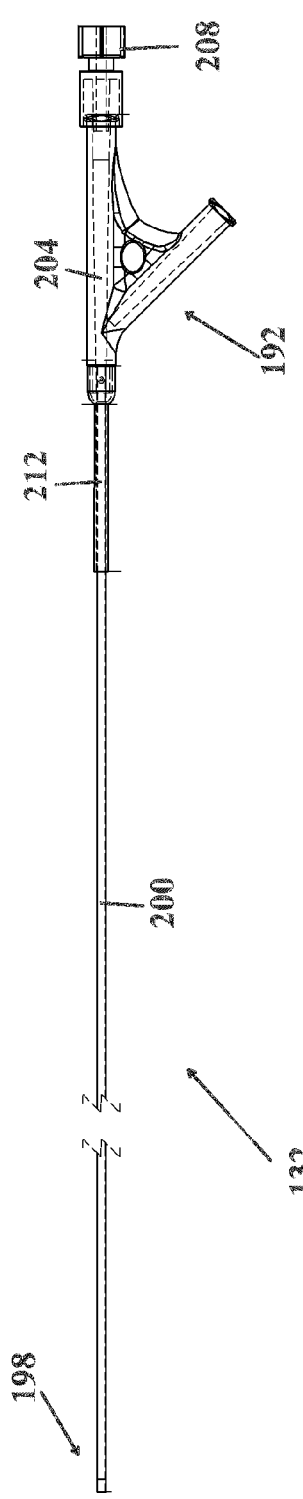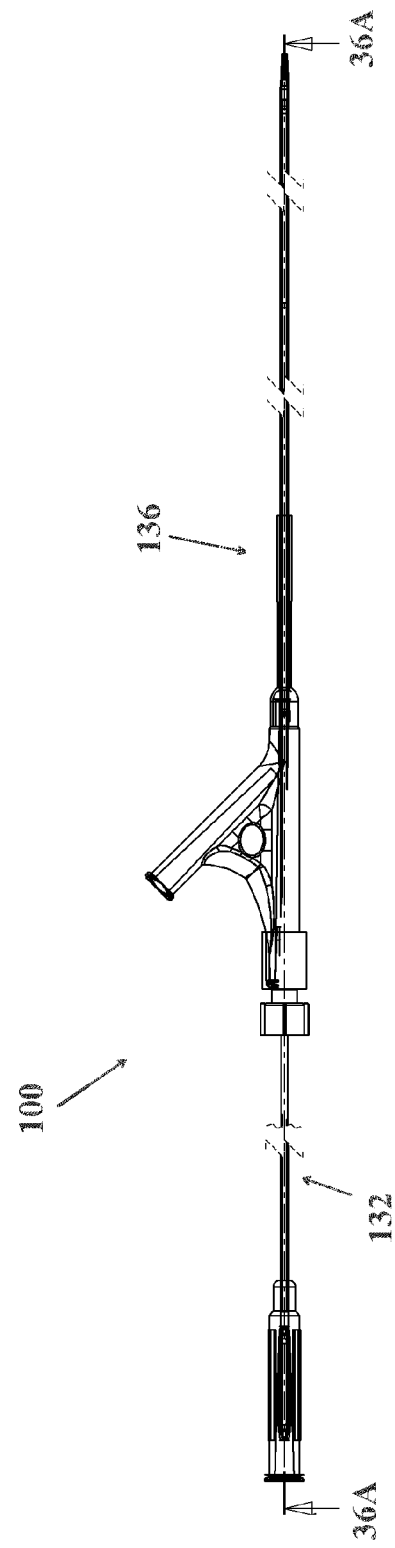
FIG. 35
FIG. 34

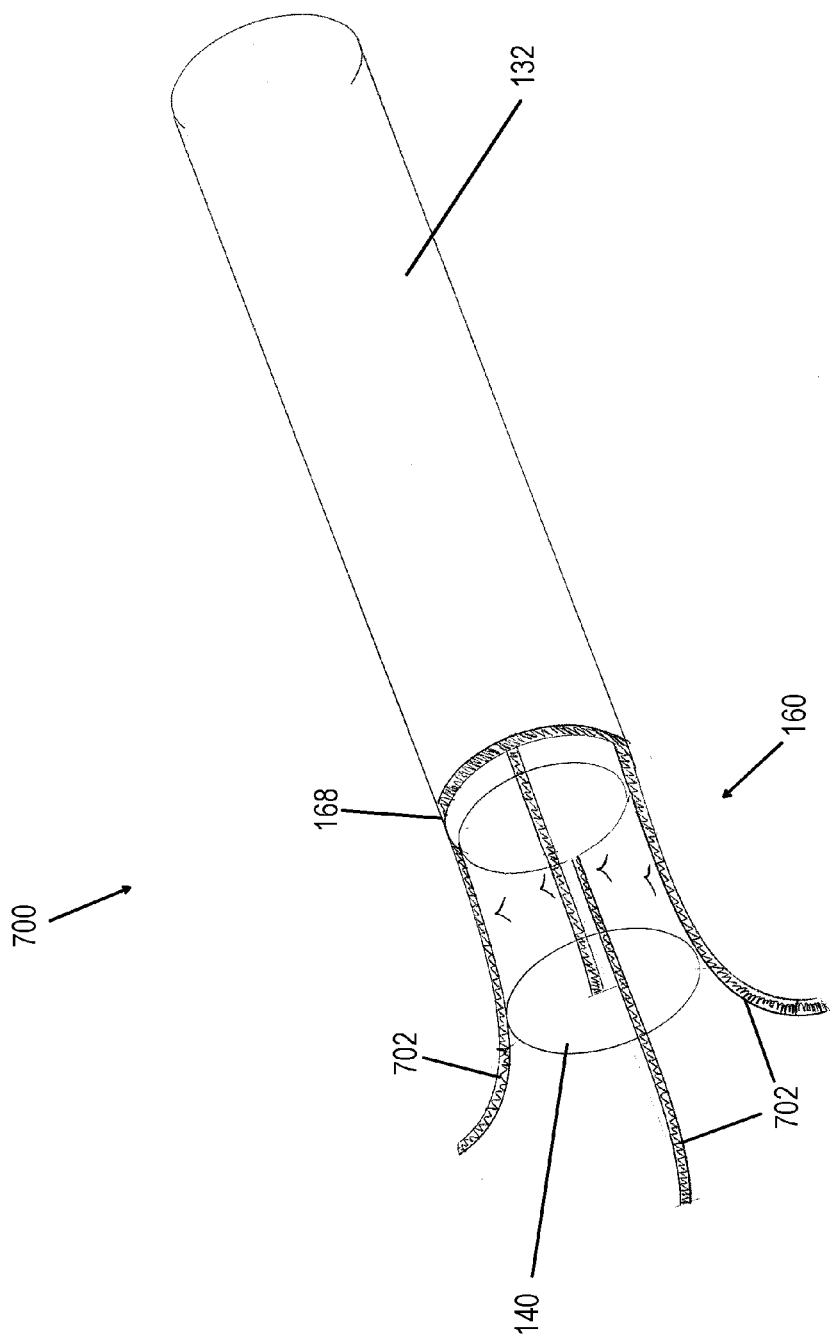

DEPLOYMENT DEVICE FOR PLACEMENT OF MULTIPLE INTRALUMINAL SURGICAL STAPLES

CROSS-REFERENCE TO RELATED APPLICATIONS

This application is a continuation-in-part of U.S. patent application Ser. No. 13/153,257, filed Jun. 3, 2011 and is continuation-in-part of U.S. patent application Ser. No. 13/118,388, filed May 28, 2011, both of which are continuations-in-part of U.S. patent application Ser. No. 12/790,819, filed May 29, 2010, which is a continuation-in-part of U.S. patent application Ser. No. 12/483,193, filed Jun. 11, 2009. This application also claims the benefit of priority of U.S. Provisional Application No. 61/362,650, filed Jul. 8, 2010. U.S. patent application Ser. No. 13/118,388 claims the benefit of U.S. Provisional Application No. 61/349,836, filed May 28, 2010. All of the above applications are incorporated by reference herein and made a part of this specification.

BACKGROUND OF THE INVENTION

Field of the Invention

This invention relates to treatment of atherosclerotic occlusive disease by intravascular procedures for pushing and holding plaque accumulated on the blood vessel walls out of the way for reopened blood flow.

Atherosclerotic occlusive disease is the primary cause of stroke, heart attack, limb loss, and death in the US and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty can form a dissection. A dissection occurs when a portion of the plaque is lifted away from the artery, is not fully adherent to the artery and may be mobile or loose. The plaque that has been disrupted by dissection protrudes into the flow stream. If the plaque lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is better to place a metal retaining structure, such as stent to hold open the artery after angioplasty and force the dissected material back against the wall of the blood vessel to create an adequate lumen for blood flow.

The clinical management of dissection after balloon angioplasty is currently performed primarily with stents. As illustrated in FIG. 1, a stent 3 is a tube having a diameter that is sized to the artery 7. A stent is placed into the artery at the location of a dissection to force the dissection flap against the inner wall of the blood vessel. Stents are usually made of metal alloys. They have varying degrees of flexibility, visibility, and different placement techniques. Stents are placed in every vascular bed in the body. The development of stents has significantly changed the approach to minimally invasive treatment of vascular disease, making it safer and in many cases more durable. The incidence of acute occlusion after balloon angioplasty has decreased significantly with stents.

However, stents have significant disadvantages and much research and development is being done to address these issues. Stents induce repeat narrowing of the treated blood vessel (recurrent stenosis). Recurrent stenosis is the "Achilles heel" of stenting. Depending on the location and the size of the artery, in-growth of intimal hyperplastic tissue from the vessel wall in between struts or through openings in the stent may occur and cause failure of the vascular reconstruction by narrowing or occlusion of the stent. This may occur any time after stent placement. In many cases, the stent itself seems to incite local vessel wall reaction that causes stenosis, even in the segment of the stent that was placed over artery segments that were not particularly narrowed or diseased during the original stent procedure. This reaction of the blood vessel to the presence of the stent is likely due to the scaffolding effect of the stent. This reaction of recurrent stenosis or tissue in growth of the blood vessel is in response to the stent. This activity shows that the extensive use of metal and vessel coverage in the artery as happens with stenting is contributing to the narrowing. The recurrent stenosis is a problem because it causes failure of the stent and there is no effective treatment. Existing treatment methods that have been used for this problem include; repeat angioplasty, cutting balloon angioplasty, cryoplasty, atherectomy, and even repeat stenting. None of these methods have a high degree of long-term success.

Stents may also fracture due to material stress. Stent fracture may occur with chronic material stress and is associated with the development of recurrent stenosis at the site of stent fracture. This is a relatively new finding and it may require specialized stent designs for each application in each vascular bed. Structural integrity of stents remains a current issue for their use. Arteries that are particularly mobile, such as the lower extremity arteries and the carotid arteries, are of particular concern. The integrity of the entire stent is tested any time the vessel bends or is compressed anywhere along the stented segment. One reason why stent fractures may occur is because a longer segment of the artery has been treated than is necessary. The scaffolding effect of the stent affects the overall mechanical behavior of the artery, making the artery less flexible. Available stenting materials have limited bending cycles and are prone to failure at repeated high frequency bending sites.

Many artery segments are stented even when they do not require it, thereby exacerbating the disadvantages of stents. There are several reasons for this. Many cases require more than one stent to be placed and often several are needed. Much of the stent length is often placed over artery segments that do not need stenting and are merely adjoining an area of dissection or disease. Stents that are adjusted to the precise length of the lesion are not available. When one attempts to place multiple stents and in the segments most in need of stenting, the cost is prohibitive since installation and material is required per stent. The time it takes to do this also adds to the cost and risk of the procedure. The more length of artery that receives a stent that it does not need, the more stiffness is conferred to the artery, and the more scaffolding affect occurs. This may also help to incite the arterial reaction to the stent that causes recurrent stenosis.

SUMMARY OF THE INVENTION

There exists a continuing need to develop new and improved devices to assist in the treatment of vascular disease, including atherosclerotic occlusive disease, among other conditions, and such as for the purposes outlined above.

In one embodiment, a system is provided for delivering a vascular prosthesis including an elongate body, a sheath, and a plurality of intravascular tacks. The elongate body has a proximal end, a distal end, and a plurality of delivery platforms disposed adjacent the distal end. Each of the delivery platforms comprises a recess extending distally of an annular marker band. The sheath has a proximal end, a distal end, and an elongate body extending therebetween. The sheath is moveable relative to the elongate body from a first position to a second position. In the first position, the distal end of the sheath is disposed distally of a distal-most distal delivery platform. In the second position, the distal end of the sheath is disposed proximally of at least one delivery platform. Each of the intravascular tack is disposed about a corresponding delivery platform.

In certain embodiments, the system is configured to place at least two tacks at a treatment zone at spaced apart locations. When so placed, a minimum gap can be provided in the treatment zone between the distal end of a proximal tack and a proximal end of a distal tack. Advantageously, the minimum gap can be provided without the need to move the elongate body or the delivery platforms.

The gap advantageously minimizes the chance that two tacks will cause kinking in the vessel or other maladies due to being too close.

A minimum spacing between adjacent distal faces of each annular marker band is provided to minimize movements of the elongate body to ensure a minimum gap of the deployed tacks. For example, in certain embodiments, there is substantially no change in the axial spacing of the deployed tacks compared to the spacing of the tacks on the delivery platforms. As a result, the minimum spacing of the distal faces can assist in preventing a too-close deployed condition of adjacent tacks.

One approach to maintaining a minimum gap, e.g., minimizing change in spacing between the undeployed and the deployed tacks, is to provide a fixture for immobilizing the proximal end of the delivery system so that motion of the system can be focused in the sheath and little if any movement is permitted in the elongate body.

Another approach involves providing a stabilization device disposed on an outer surface of the delivery system to minimize at least one of axial or radial shifting of at least one of the delivery platforms.

In another embodiment, a method is provided for placing an intravascular tack. A catheter system is provided that includes an elongate body having a plurality of spaced apart delivery platforms disposed adjacent a distal portion of the elongate body. The position of at least one of said delivery platforms is indicated by a marker band. Each platform has plaque tack disposed thereon. The distal portion of the elongate body is advanced through the vasculature of a patient until the marker band is proximal or distal of a treatment zone comprising dissected plaque. The marker band is visualized to confirm the location of at least one of said delivery platforms relative to the dissected plaque. The outer sheath is retracted while maintaining the position of the elongated body and thereafter at least two of the tacks are deployed to position the tacks at a pre-determined location and spacing.

In various methods, a stabilizer can be deployed prior to tack deployment. The elongate body can be stabilized by actuating a stabilizer disposed at the distal end of the catheter system or by coupling the elongate body to a fixture at the proximal end to minimize unwanted shifting in the vessel at the distal end of the elongate body in the vicinity of the delivery platforms.

In another embodiment, a system for delivering a vascular prosthesis is provided that includes an elongate body, an elongate packet, and a sheath. The elongate body comprising a distal end, a proximal end, and a plunger disposed adjacent the distal end. The elongate packet has a plurality of intravascular tacks coupled therewith. The tacks are disposed along the length of the elongate packet. The sheath has a proximal end and a distal end and is moveable relative to the elongate body from a first position in which the distal end of the sheath is disposed distally of at least a portion of the elongate packet to a second position in which the distal end of the sheath is disposed proximally of the elongate packet. The elongate packet is configured to maintain a minimum spacing between adjacent tacks during deployment and to permit expansion and separation from the elongate body. The elongate packet is configured to release the tacks to expand toward a vessel wall after deployment.

An endoluminal staple can include proximal and distal circumferential members. The proximal circumferential member can be disposed at a proximal end of the endoluminal staple. The distal circumferential member can be disposed at a distal end of the endoluminal staple. In some embodiments, the distal circumferential member is the distal most aspect of the endoluminal staple and the proximal circumferential member is the proximal most aspect of the endoluminal staple. The proximal and distal circumferential members can be connected by bridge members. The bridge members can include one or more anchors configured to engage the plaque and/or the blood vessel wall. The anchors can an increased material thickness verses the rest of the tack which increases radiopacity of the anchor and eliminates the need for a separate visibility marker.

BRIEF DESCRIPTION OF THE DRAWINGS

These and other features, aspects and advantages are described below with reference to drawings of preferred embodiments, which are intended to illustrate but not to limit the present invention.

FIG. 4B is a plan view of the distal portion of the delivery device shown in

FIG. 4.

FIG. 4C is a cross-sectional view of the distal portion of FIG. 4B showing a plurality of tack devices prepared for implantation.

FIG. 4D shows the deployment of two tack devices upon retraction of a sheath.

FIG. 5C1 shows a variation on the embodiment of FIGS. 5A-5C having an increased size anchor.

FIG. 32A-32B show the proximal and distal end views respectively of a system for delivering a vascular prosthesis, where a distal end of a sheath of the system is disposed distally of one or more plaque tacks.

FIG. 33A-33B show the proximal and distal end views respectively of the system of FIGS. 32A-32B, where the sheath distal end is disposed proximally of one or more plaque tacks.

FIG. 34 shows a system for delivering a vascular prosthesis.

FIG. 35 shows a sheath that can be used to retain and to deploy one or more tacks.

FIG. 49 shows a shuttle deployment device.

DETAILED DESCRIPTION OF THE PREFERRED EMBODIMENT

The subject matter of this application is directed to the improvement of a plaque tack or staple device. The plaque tack or staple device can be used for treating atherosclerotic occlusive disease. The plaque tack can be used to hold loose plaque against a blood vessel wall. The plaque tack can include an annular member configured to apply an expansion force to the loose plaque.

I. Overview of Endolumenal Tack Treatment

Figure 2:
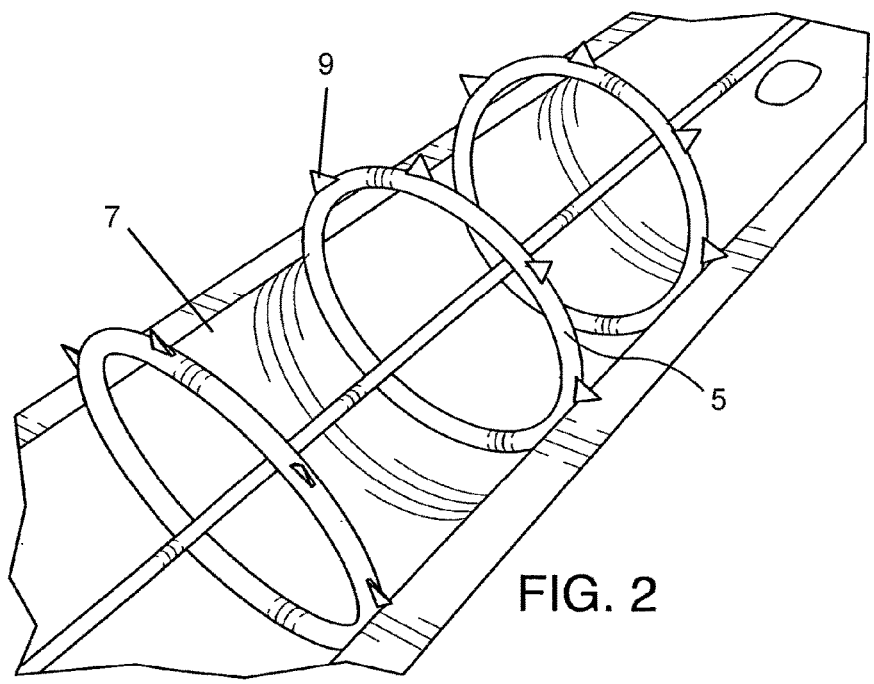
FIG. 2 illustrates the use of plaque tacks installed after an endolumenal procedure demonstrating advantages over the prior art.

FIG. 2 shows one embodiment of a plaque tack or staple device 5 that includes a thin, annular band or ring of durable, flexible material. The tack device can be inserted into a blood vessel in a compressed state and installed in an expanded state against the blood vessel wall using a catheter delivery mechanism at one or more specific positions of loose plaque. The plaque tack 5 can be deployed after or as part of an angioplasty procedure. The plaque tack 5 is adapted to apply an expansion force against the plaque in the blood vessel 7 to press and hold the plaque against the blood vessel walls. The tack device can be radially outwardly expandable under a spring or other expansion force. Preferably the fully expanded diameter of the tack 5 is greater than the transverse size of the vessel to be treated. As discussed below, the tack 5 advantageously can be deployed in a surprising large range of blood vessel sizes.

The plaque tack 5 can include a plurality of plaque anchors 9 on its outer annular periphery. The plaque anchors 9 can be embedded into or at least placed in physical contact with plaque by expanding up against the plaque. In certain embodiments, the plaque anchors 9 are adapted to elevate adjacent sections of the tack 5 relative to the wall of the vessel. In at least this sense, the anchors 9 may have some of the advantages of focal elevating elements that are discussed in SECTION III below. The anchors 9 exert a holding force on the plaque while minimizing the amount of material surface area in contact with the plaque or blood vessel wall. As another feature, the plaque tack 5 can extend over only a small area in the axial direction of the vessel wall, in order to minimize the amount of foreign structure placed in the blood vessel. For example, each plaque tack 5 can have an axial length L that is only a small fraction of the axial length of a typical stent.

The plaque tack devices of the present application are designed as a minimally invasive approach to tacking loose or dissected atherosclerotic plaque to the wall of the artery, as illustrated in FIG. 2. The plaque tack may be used to treat either de novo atherosclerotic lesions or the inadequate results of balloon angioplasty. The plaque tack is designed to maintain adequate lumen in a treated artery without the inherent disadvantages of vascular stents. The device may also be used to administer medications, fluid, or other treatment ("eluting") agents into the atherosclerotic plaque or the wall of the blood vessel or into the bloodstream.

One or more plaque tacks 5 can be accurately deployed in positions along the length of a plaque accumulation site where specific holding forces are needed to stabilize the site and/or hold pieces of plaque out of the way of blood flow.

FIG. 2 shows that in various plaque tack treatments, a plurality of plaque tacks 5 can be deployed to treat locations that are axially spaced along the vessel 7. In this way, targeted treatments can be provided to hold loose plaque against a vessel wall without over-scaffolding as discussed below. The plaque tack 5 and installation procedure may be designed in a number of ways that share a common methodology of utilizing the outward force of a spring-like annular band to enable the tack to be compressed, folded, or plied to take up a small-diameter volume so that it can be moved into position in the blood vessel on a sheath or catheter, then released, unfolded or unplied to an expanded state within the blood vessel.

The plaque tack device can be delivered into the blood vessel from endovascular insertion. SECTION IV below discusses a variety of delivery methodologies and devices that can be used to deploy plaque tacks. The delivery device for the different embodiments can be the same, or can be different with features specifically designed to deliver the specific tack. The plaque tack and installation procedure may be designed in a number of ways that share a common methodology of utilizing an expansion force of the delivery mechanism (such as balloon expansion) and/or the expansion force of a compressible annular band to enable the tack to be moved into position in the blood vessel, then released, unfolded or unplied to an expanded state within the blood vessel.

II. Further Embodiments of Endoluminal Staples

Variations of the plaque tack 5 can have a mesh-like configuration and can be arranged with one or more circumferential members formed with discrete struts, such as in open and closed cell constructions, among other designs.

A. Plaque Tack with Metallic Mesh Construction

Figure 3:
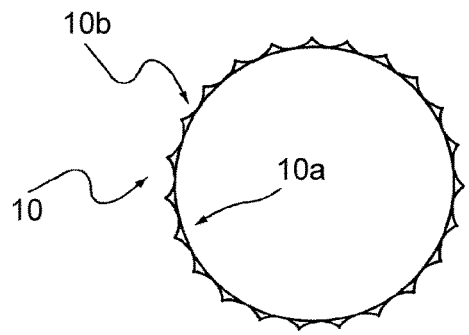
FIG. 3A shows an embodiment of a plaque tack in end view.
FIG. 3B shows it in side view.
FIG. 3C shows the plaque tack in perspective.
FIG. 3D shows a section of the plaque tack in a flat or rolled-out view.
Figure 3B:
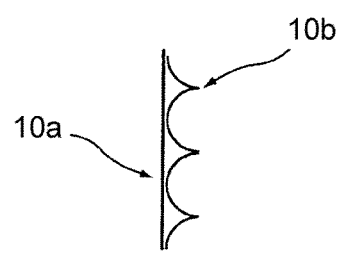
Figure 3C:
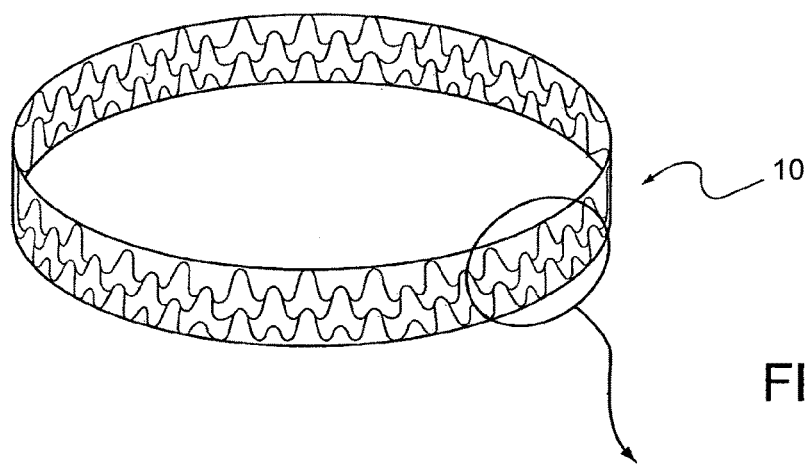
Figure 3D:
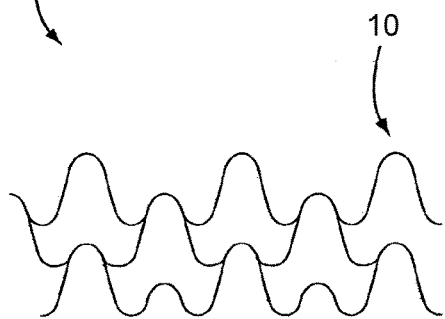

An embodiment of a plaque tack 10 in the form of a metallic mesh construction is illustrated in FIGS. 3A-D. The plaque tack 10 is shown having a closed cell construction with an annular band 10a formed of interleaved mesh, and radially outwardly extending projections 10b. The plaque tack 10 may be laser cut or etched out of a metal tube form or made of thin metal wire which is looped and interleaved in a mesh that is welded, soldered, looped and/or linked together into the desired mesh shape as can be seen in FIGS. 3C-D. The projections 10b can project out from the annular band 10a. The projections 10b can be on an outer surface of the tack and can contact and/or embed into the wall of a blood vessel.

The annular band of the plaque tack 10 can have a dimension in the axial direction of the vessel walls (sometimes referred to herein as length) that is about equal to or less than its expanded diameter, in order to minimize the emplacement of foreign scaffolding structure in the blood vessel. Expanded diameter means final diameter in an unconstrained expansion. One or more tacks can be applied only in positions along the length of a plaque accumulation site where specific holding forces are needed to stabilize the site and/or hold pieces of plaque out of the way of blood flow.

The mesh pattern can be designed so that the plaque tack 10 can be compressed radially inward to a smaller-volume size. This can allow the plaque tack 10 to be loaded onto or within a catheter delivery device to be inserted into the blood vessel. For example, the tack 10 can have an overall circular shape with bends, such as inner V bends, that allow it to be folded in zig-zag fashion to a compressed smaller-volume form for loading in a delivery catheter, such as a deployment tube.

At the desired position in the blood vessel, the compressed plaque tack 10 is released from the delivery catheter. The mesh combined with an annular, ring shape can allow the plaque tack 10 to spring back to its expanded shape. Alternatively, the tack 10 can be expanded by another device, such as by a balloon. FIG. 3C shows the plaque tack 10 at rest in its fully expanded state and FIG. 3D shows a detail of a section of the metallic mesh.

Figure 4:
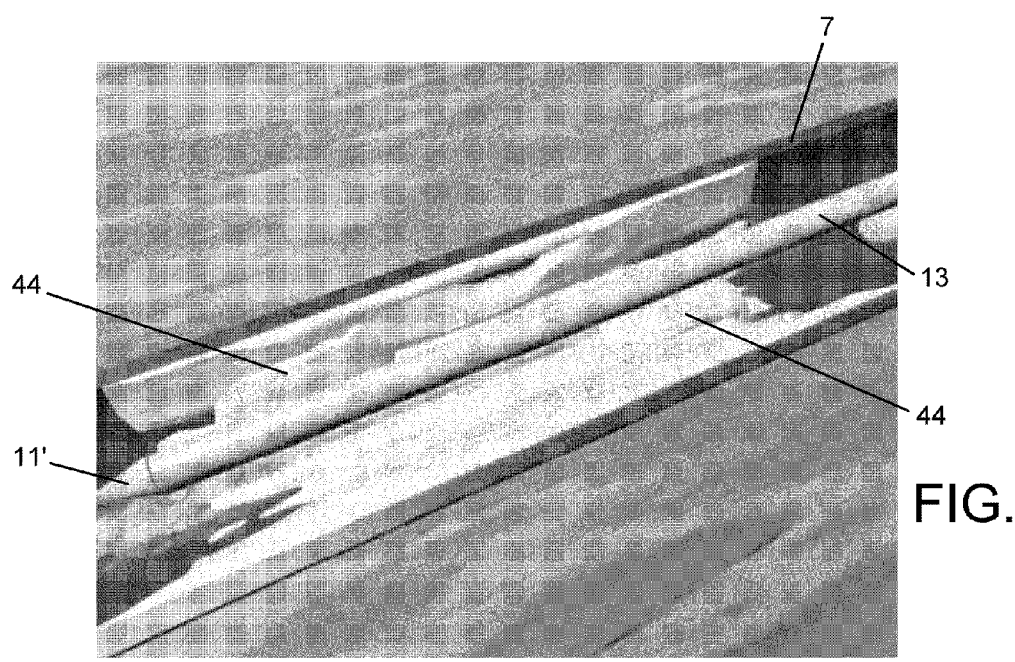
FIG. 4 is a schematic representation of a distal portion of a delivery device that has been advanced to a treatment site expanded in the blood vessel.

FIGS. 4-4D show that one or more plaque tacks 10 can be positioned in a patient's vasculature at a treatment site by a delivery device 11 with an outer sheath 13 and thereafter expanded. Enhancements of the delivery device 11 are discussed below in SECTION IV. The tack 10 can be expanded in any suitable way, such as by being configured to self-expand or to be balloon expanded. In the illustrated embodiment, a plurality of self-expanding tacks 10 (or variants, such as tack 10' or tack 10") is disposed inside the sheath 13. The delivery device 11 includes an elongate body 11A that is disposed at least partially within the sheath 13. The delivery device 11 also includes a dilating structure 11B that atraumatically displaces tissue and helps to guide the delivery device 11 through the vasculature. The body 11A can be configured with a lumen 11C extending therethrough for receipt and slideable advancement of a guidewire 40 therein. In the illustrated embodiment, the sheath 13 and the dilating structure 11B meet to provide a smooth outer surface to the delivery device 11, e.g. having the same outside diameter where they meet. The body 11A can be configured with a plurality of annular recesses 11D in which tacks 10, 10', 10" can be disposed. The annular recesses 11D can be defined between one or more shoulders 11E that prevent proximal or distal slippage of the tacks along the elongate body 11A. The recesses 11D could be eliminated by providing another structure for axially fixing the tacks 10, 10', 10" along the elongate body 10A.

Figure 4A:
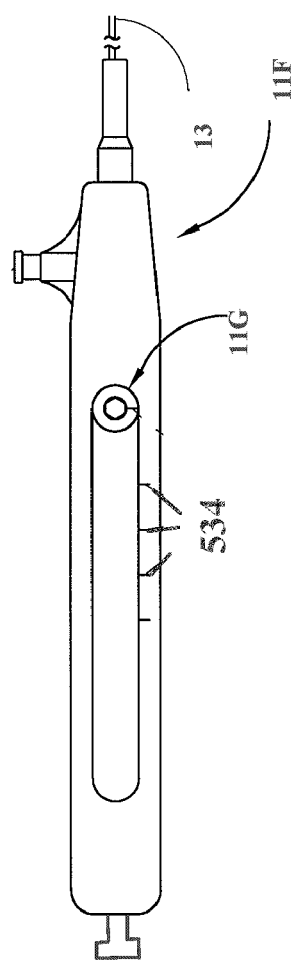
FIG. 4A illustrates the proximal end of one embodiment of a delivery device.

FIGS. 4A and 4D show a proximal end of the device 11 and a manner of deploying the tacks 10, 10', 10". In particular, the proximal end of the device 11 includes a handle 11F and an actuator 11G. The actuator 11G is coupled with a proximal end of the sheath 13 such that proximal and distal movements of the actuator 11G cause proximal and distal movement of the sheath 13. FIG. 4A illustrates a distal positioning of the actuator 11G which corresponds to a forward position of the sheath 13 relative to the elongate body 11A and the recesses 11D. In this position the recesses 11D and the tacks 10, 10', 10" are covered by the sheath. Movement of the actuator 11G proximally relative to the handle 11F causes the sheath 13 to move proximally, e.g., to the position of FIG. 4D. In this position, the distal most two tacks 10, 10', 10" are uncovered and are permitted to self-expand in the manner discussed herein.

Returning now to FIGS. 3A-B, the projections 10b on the surface of the tack 10 can act as anchors or elevating elements to embed into or press against the plaque. An array of anchors or elevating elements can be used for linking the annular band of the tack with the plaque mass or blood vessel wall. The projections 10b can be made of a sufficiently rigid material to sustain a locking or engaging relationship with the blood vessel tissue and/or to pierce or engage the plaque and maintain the locking or engaging relationship therewith. The projections 10b may project at an angle of 90 degrees to the tangent of the annular band, or an acute angle may also be used.

The plaque tack may be made of a material such as a corrosion-resistant metal, polymer, composite or other durable, flexible material. A preferred material is a metal having "shape memory" (such as Nitinol). In some embodiments, a tack may have an axial length of about 0.1 to 6 mm, an expanded diameter of about 1 to 10 mm, and an anchor height from 0.01 to 5 mm. In general, the annular band of the plaque tack has a length in the axial direction of the vessel walls that is about equal to or less than its diameter, in order to minimize the amount of foreign structure to be emplaced in the blood vessel. The annular band can have a ratio of axial length to diameter as low as 1/100.

B. Plaque Tack with Open Cell Construction

Figure 5A:
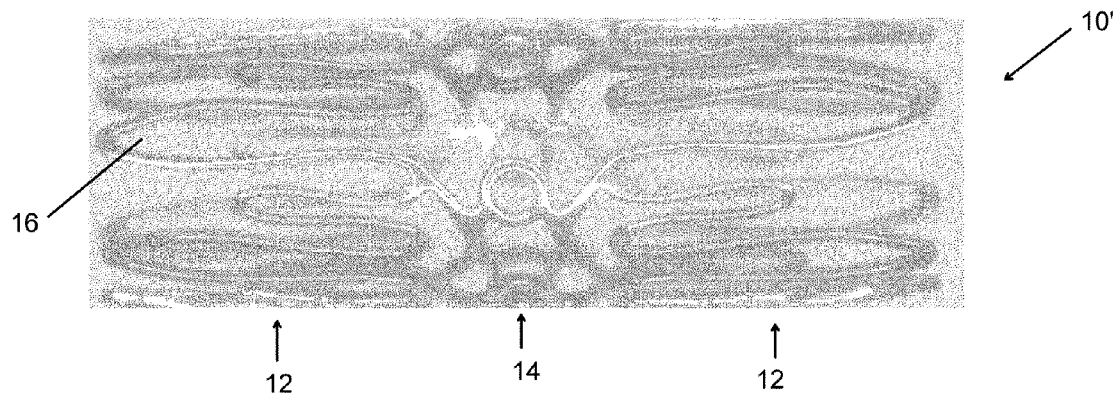
FIGS. 5A and 5B show another embodiment of a plaque tack in a collapsed state and in an expanded state, respectively.
Figure 5B:
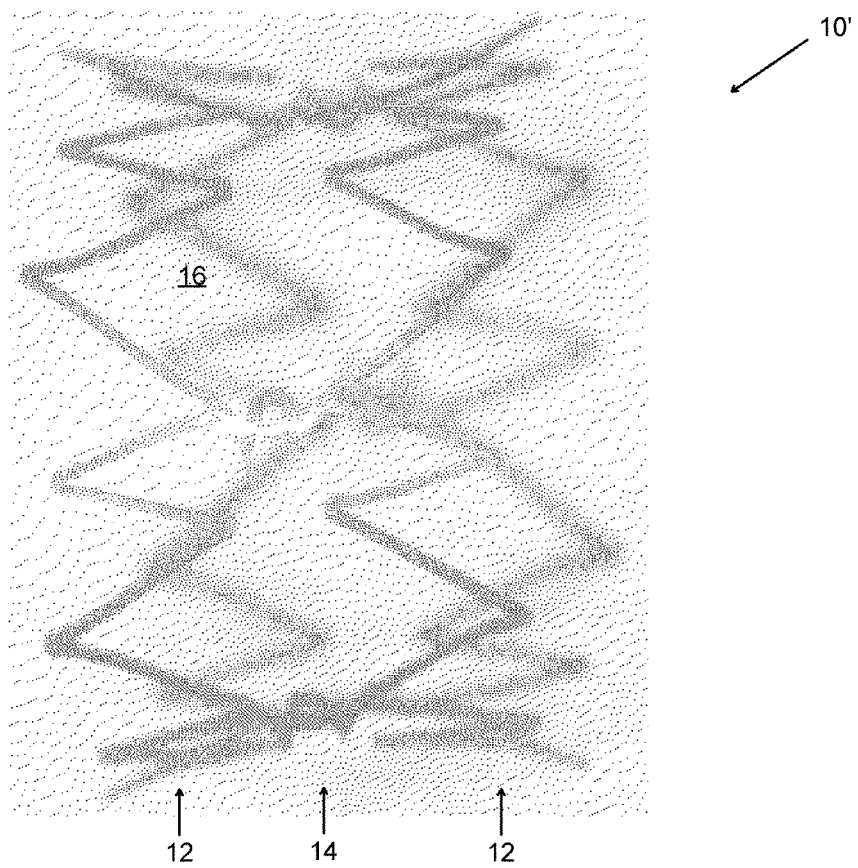
Figure 5C:
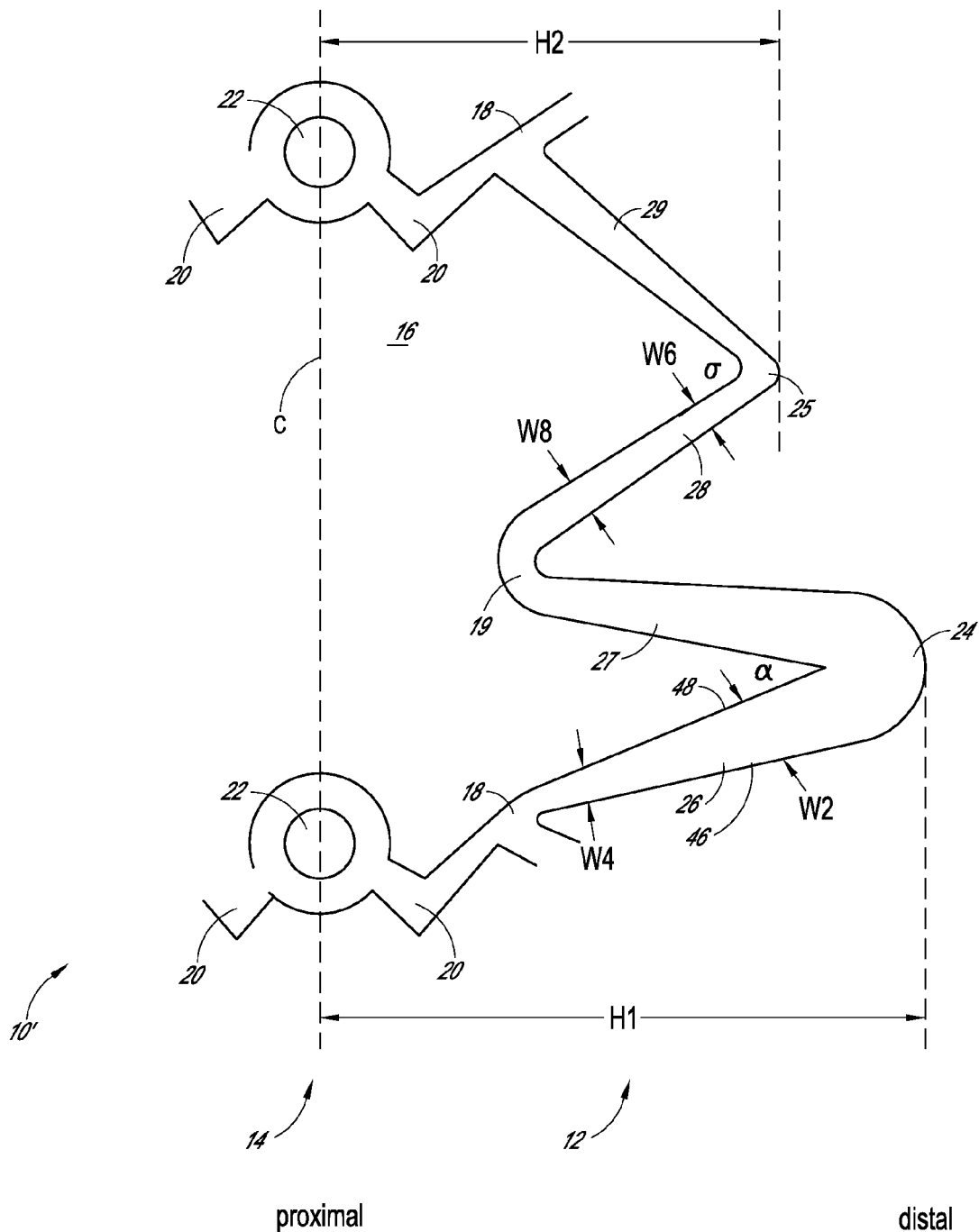
FIG. 5C shows a detail view of a section of the plaque tack of FIG. 5A-B.

FIGS. 5A-5C illustrate that in certain embodiments, a plaque tack 10' can be configured with an open cell structure. The plaque tack 10' can include one or more circumferential members that have undulating, e.g. sinusoidal, configurations and that are spaced apart in the axial direction. The circumferential members can be coupled together at one or more circumferentially spaced locations by axially extending members, sometimes referred to herein as bridge members. These embodiments are expandable over a wide range of diameters and, as discussed below, can be deployed in a variety of different vessels.

The plaque tack 10' can have features similar to those described above with respect to the plaque tack 10. For example, the plaque tack 10' may also be laser cut or etched out of a metal tube form. Similarly, the plaque tack 10' may be made of a material such as a corrosion-resistant metal (e.g., certain coated or uncoated stainless steel or cobalt-chromium alloys), polymer, composite or other durable, flexible material. A preferred material is a metal having "shape memory" (such as Nitinol).

FIGS. 5A-B show the overall structure of the plaque tack 10' with an open cell arrangement. The plaque tack 10' is shown having two circumferential members 12, which can be rings formed by a plurality of zig-zag struts, joined by bridges 14 that extend between the rings 12. The rings and bridges define a column of bounded cells 16 along an outer surface of the tack. The outer surface extends about an outer periphery, e.g., an outer circumference of the tack 10'. The boundary of each of the cells 16 is made up of a number of members or struts. As shown, the second ring is a mirror image of the first ring, though the first and second rings may be circumferential members with different configurations. Also, the bridges 14 can be symmetrical across a transverse plane extending through the axial mid-point thereof, though other configurations are also possible. The rings 12 can be considered coaxial, where that term is defined broadly to include two spaced apart rings, or structures, having centers of rotation or mass that are disposed along a common axis, e.g., the central longitudinal axis of the tack 10'.

FIG. 5C is a schematic flat depiction of a portion of a tack 10' illustrating a portion of the cell 16 and a portion of a boundary thereof. The portion illustrated to the right of the midline C is one half of the cell 16 in one embodiment. The other half can be a mirror image, as shown in FIGS. 5A-B, an inverted mirror image, or some other configuration. The portion of the ring 12 that is part of an individual cell 16 can define a portion that is repeated in a pattern along the ring. In some embodiments, the ring 12 can have portions that are repeated in a pattern that extends across cells, such as across 1.5 cells, 2 cells, 3, cells, etc. The pattern of the rings 12 combined with other features of the tack 10' can enable it to be circumferentially compressible. The difference between the compressed and expanded states can be seen by comparing the compressed view shown in FIG. 5A and the expanded view shown in FIG. 5B.

The cells 16 of the tack 10' can be bounded by portions of two rings 12, which can be mirror images of each other. Thus, some embodiments can be fully described by reference to only one side of the tack 10' and of the cell 16. The ring 12, a portion of which is illustrated in FIG. 5C, has an undulating sinusoidal pattern. The undulating pattern can have one or more amplitudes, such as the dual amplitude configuration shown.

The rings 12 can have a plurality of struts or structural members 26, 27, 28, 29. The plurality of struts can repeat about the circumference of the ring 12. The struts can be many different shapes and sizes. The struts can extend in various different configurations. In some embodiments, the plurality of struts 26, 27, 28, 29 extend between inward 18, 19 and outward apices 24, 25.

In some embodiments, the outward apices 24, 25 extend axially different distances as measured from a central zone or midline C of the tack 10'. In particular, the apex 24 can be considered a high apex and the apex 25 can be considered a low apex in this regard. The inward apices 18, 19 may be axially aligned, e.g., being positioned at the same axial distance from the midline C. Thus, the outward apex 24 is disposed farther away from the bridge and inward apices than the outward apex 25. In some embodiments, the axial length of the tack 10' is measured from the top of the outward apex 24 on one side of the cell 16 to the corresponding top of the outward apex 24 on the other side of the cell. Put another way, the first outward apex 24 extends a first axial distance from the midline C of the tack 10' and the second outward apex 25 extends a second axial distance from the central zone C of the tack 10', the first distance being greater than the second distance. Each side of the cell 16 as shown has one high outward apex 24 and one low outward apex 25.

The bridge 14 can be connected to the one or more of the inward apices 18, 19. The bridge 14 can join the two rings 12 together. The bridge 14 can have many different shapes and configurations. Some embodiments of the tack 10' have a proximal ring and a distal ring with the bridge disposed between and connecting them. As mentioned above, the bridge 14 can be located at the central zone or midline C of the tack 10'. In FIG. 5C, the word "proximal" refers to a location on the tack 10' that would be closest to vascular access site than the portion labeled "distal". However, the tack 10' can also be thought of as having a medial portion that corresponds to the midline C and lateral portions extending in both directions therefrom. As such, the location labeled "proximal" is also a medial location and the location labeled "distal" is also a lateral position. All of these terms may be used herein.

As shown, the bridge 14 is connected to each ring at the inward apex 18. In some embodiments, a bridge is connected to every inward apex, forming a closed cell construction. In other embodiments, the bridge 14 is connected to every other inward apex, every third inward apex, or spaced farther apart by as needed, forming a variety of open cell configurations. The number of bridges 14 can be chosen depending upon the application. For example, six or fewer bridges 14 may be used between the two rings 12 when desired for limiting neointimal hyperplasia.

One technique for enhancing the plaque holding capability of the bridges 14 is to align plaque holding structures (such as the barb 9, projections 10b, or the anchors discussed below) with a force application location or direction of the ring 12. In some embodiments, at least a portion of the bridge 14 can be aligned, with one of the struts of the ring 12. For example, where the bridge 14 connects to the ring 12, whether at an inward apex or at a strut, that connecting portion of the bridge can extend therefrom in a manner that is aligned, partially or substantially aligned with a strut. FIG. 5C shows that the bridge 14 is connected to the inward apex 18 and that the connecting portion of the bridge is substantially aligned with the strut 26. In one technique, a plaque holding structure of the bridge 14 is disposed on a projection of a longitudinal axis $L_A$ of the strut 26. As discussed below, the tack 10' has a plurality of anchors 20. The axis $L_A$ intersects a portion of an anchor 20 to maximize a torque effect from the expanded strut 26 to the anchor 20. In the arrangement of FIG. 5C, an anchor on an opposite side of the centerline C is disposed on the projection of the axis $L_A$ and the projection of a longitudinal axis $L_A$ of a mirror image strut 26 intersects the anchor 20 of the strut on the same side of the centerline C as the strut 26 shown in FIG. 5C. In another technique, the projection of the strut 26 and its mirror image strut can be aligned with the centerline C, which is rigidly coupled with the anchors 20. The bridge 14 also is aligned with a high amplitude sinusoidal section of the tack 10'.

A series of unique design features can be integrated into the tack 10' for various purposes as will be discussed in more detail in the sections below. For example, the tack 10' can include one or more of anchors, markers and focal elevating elements, among other features. As discussed above, FIG. 5C shows that the plaque tack 10' can include a plurality of (e.g., two) anchors 20. The tack 10' also can include a position marker 22 on each bridge 14. The position markers 22 can be fluoroscopically opaque and in one arrangement are generally flat. As used in this context, flat markers are arranged to have a planar outer face that is tangential to a cylinder that extends through an outer surface of the tack 10' or that is concentric with the outer surface but disposed radially inside the outer surface. The anchors 20 can similarly be configured to be tangential to a cylinder that extends through an outer surface of the tack 10'.

As another example, a series of unique design features can be integrated into the tack 10' for dynamic distribution of stresses within the tack 10'. These design features can enable the uniform control of the tack 10' during compression, expansion, delivery, and catheter release. The design features can also individually and/or collectively manage the stresses throughout the bulk of the tack, along the struts, and at the interface of the tack and the blood vessel lumen. Better control of the distribution of stresses within the tack has the benefit of reducing cellular response and tack fracture by limiting strut fatigue and the associated micro-rubbing at the tack-blood vessel interface. Micro-rubbing includes a variety of small scale adverse interactions between implants and patient tissue, such as abrasion or friction that occurs on a cellular or intercellular level between the tack and the blood vessel lumen.

A reduction in cellular response is believed to be achieved partly through a reduction of surface area contact between the tack and the blood vessel lumen and partly by maximizing alignment of the contact points or structures with the blood vessel cells' natural orientation. Thus, the tack is able to move with the blood vessel while decreasing the micro-rubbing. Other devices, such as stents, contact the blood vessel cells in ways that may extend across, e.g., transversely to, multiple cells increasing micro rubbing at the stent-blood vessel interface.

1. Single Column Cell Design

One characteristic of the embodiment the tack 10' of FIGS. 5A-C is that it includes a single column open cell design contained between two zig-zag rings. This arrangement provides minimal (if any) scaffolding of a vessel. In one sense, a ratio of the vessel contact area to the total treatment zone of the plaque tack 10' is small. In this context, vessel contact area is the sum of the area of outer portions of the tack 10' that may come into contact with the vessel wall. More particularly, the vessel contact area may be calculated as a summation for all of the struts of the length of each strut times the average transverse dimension (width) of the radially outer surface of each strut. If the struts of the zig-zag rings are laser cut, the width of the radially outer surface of the strut may be less than that of the radially inner surface. The vessel contact area may also include the radially outer surface of the bridges 14. The total treatment zone of the plaque tack 10' can be defined with respect to the fully expanded configuration in a best fit cylinder. A best fit cylinder is one that has an inner circumference that equal to the unconstrained circumference of the plaque tack 10'. The total treatment zone has an area that is defined between the proximal and distal ends (or the lateral edges) of the plaque tack 10'. The total treatment zone can be calculated as the length between the proximal and distal ends (or lateral edges) in the best fit cylinder times the inner circumference of the best fit cylinder. In the illustrated embodiment, the length for purposes of determining the total footprint can be the distance at the same circumferential position between high outward apices of the rings 12.

In various embodiments, the ratio of the vessel contact area to total treatment zone is less than 50%. In some embodiments, the ratio of the vessel contact area to total treatment zone is even less, e.g., 40% or less. The ratio of the vessel contact area to total treatment zone can be as small as 20% or less. In specific examples, the ratio of the vessel contact area to total treatment zone is 5% or even 2% or less. As discussed below, focal elevating elements can augment this advantageous feature, even further lowering the ratio of the vessel contact area to total treatment zone by providing separation between the vessel wall and at least a portion the circumferential members 12.

In certain methods, a vessel can be treated by implanting a plurality of structures, e.g., plaque tack 10'. The structures have a total contact area with the vessel wall. The total contact area may be the sum of the vessel contact area of the individual structures. In the method, a total treatment zone area can be defined as the surface area between the proximal end of the most proximal structure and the distal end of the distal most structure. In one method, the total contact area is no more than about 55% of the total treatment zone area. More typically, the total contact area is between about 10% and about 30% of the total treatment zone area. In specific examples, the total contact area is no more than 5-10% of the total treatment zone area.

The tack 10' can also be understood to provide a relatively high open area within its lateral edges compared to stents. Distinct from traditional stents, the track 10' need not include sufficient metal to provide a scaffolding function, to hold a vessel open. To accomplish many of the contemplated treatments, the tack 10' can be configured to limit its contact to only a single point or a plurality of discrete points, for example at one or more axial locations. The discrete points can be widely spaced apart, such as by being points on a circumference that are separated by spaces or, when applied, vascular tissue.

In some embodiments, the open area bounded by lateral edges of the tack 10' dominates the total footprint, as defined above. The open area of the tack 10' can be defined as the sum of the areas of the cells 16 when the tack 10' is in the fully expanded configuration, as defined above. The open area should be calculated at the outer circumference of the tack 10', for example the area extending between the internal lateral edges of each of the struts. In this context, internal lateral edges are those that form at least a part of the boundary of the cells 16. In various embodiments, the sum of the radially outwardly facing surface of the struts of the tack 10' can be no more than about 25% of the open area of the tack 10'. More typically, the sum of the radially outwardly facing surface of the struts of the tack 10' is between about 10% to about 20% of the open area of the tack 10'. In other examples, the sum of the radially outwardly facing surface of the struts of the tack 10' is less than about 2% of the open area of the tack 10'.

A single column design includes arrangements in a plurality of tack cells are oriented circumferentially about a central axis of the tack 10'. Tack cells can come in many configurations, but generally include spaces enclosed by struts and are disposed in the wall surface of the tack. Open cell designs include arrangements in which at least some of a plurality of internally disposed struts of proximal and distal circumferential members are not connected by bridges or axial connectors. FIG. 5C shows that the inward apex 19 is unconnected to a corresponding inward apex on a mirror image ring 12. Thus, a portion of the cell 16 disposed above the inward apex 19 in FIG. 5C is open to another portion of the cell 16 disposed below the inward apex 19. Open cell designs have increased flexibility and expandability compared to closed cell designs, in which each internally disposed struts of a proximal circumferential member is connected to a corresponding internally disposed struts of an adjacent circumferential member. The cell 16 would be divided into two closed cells by connecting the inward apex 19 to a corresponding inward apex on the mirror image ring 12. As discussed above, closed cell plaque tacks can be suitable for certain indications and can include other features described herein. As shown, the single column open cell design extends along the midline C of the bridge (and also, in this embodiment, along the circumference of the tack 10').

In one embodiment the cell 16 is identical to a plurality of additional cells 16 that would be disposed circumferentially about the central axis of the tack 10'. The number of cells can vary depending on factors such as the size of the vessel(s) for which the tack 10' is configured, the preferred arrangements of the rings 12, the number of bridges 14 to be provided and other factors.

As discussed above, the tack 10' can include proximal and distal rings 12 connected by bridges 14. The proximal ring 12 can be disposed at a proximal end of the tack 10'. The distal ring can be disposed at a distal end of the tack 10'. In some embodiments, the distal ring is the distal most aspect of the tack 10' and the proximal circumferential member is the proximal most aspect of the tack 10'. The bridges 14 can divide an outer surface of the tack 10' into cells 16 bounded by the bridges 14 and a portion of each of the proximal and distal rings 12. In the embodiment of FIGS. 5A-5C, the single column design is provided by providing bridges at only one axial position and only a pair of circumferential members or rings 12. FIG. 5C includes the terms "distal" and "proximal" for reference purposes related to this and other examples, thus the ring 12 shown is the distal ring. In other embodiments, the ring 12 shown can be the proximal ring.

As discussed above, the cells 16 can have one of many different shapes and configurations. FIG. 5B shows that, the cells 16 are aligned as a repeating pattern forming a single column open cell design along the circumference of the tack 10'.

Conventional stent designs are generally relatively long (e.g., 4 cm and even up to 20 cm when used in peripheral vasculature) from their distal to proximal ends. Where arranged with circumferentially disposed cells, conventional stents have a large number of columns of cells. These designs are burdened with repeating points of weakness and can generate stresses that become difficult to manage. As the device is put under stress and strain, these conventional stents must find regions of greater pliability within the strut matrix. These strut regions absorb the load throughout the system and under periods of repeated external forces begin to fail, such as through metallurgical friction loading.

The single column configuration of the tack 10' is not subject to repeated weak point loading due to movement of remote stent portions because the tack does not have to be axially elongated to provide effective tacking treatment. Other benefits that derive from the shortness include reduced friction at the interface with the catheter sheath during delivery and with the blood vessel wall. As discussed above, the stress at the blood vessel wall interface is reduced due to the lack of cell-to-cell dragging or pulling which in turn reduces the potential that the tack will pull or drag adjacent cells increasing cellular inflammation or histological response along the lumen wall. A single column or other axial short configuration also reduces the stress along each strut because the overall length of single column or other axial short structures or configurations are less affected by the anatomical motion (e.g., bending, twisting, and rotating). This results, at least in part, from the anatomy shifting around short structures while longer structures do not allow the anatomy to shift and thus longer structures absorb more forces resulting from this anatomical motion.

Any motion between the surfaces of the tack and the blood vessel can cause rubbing and friction. If the motion is very small it can be described as micro-rubbing, as discussed above. Even micro-rubbing produces a negative effect on both the tack 10' and the biological cells of the blood vessel. For example, friction occurs when a portion of an implanted object moves while another portion is stationary or moving by a smaller amount. Differential amounts of moving over time weakens the material leading to fracture by processes such as work hardening. The biological cells become irritated by the friction and can respond by producing an inflammation response. Inflammation can drive a variety of undesired histological responses including neointimal hyperplasia and restenosis.

2. Controlled Angle of Struts

FIG. 5C shows that the tack 10' has two circumferential members or rings 12 which each have a plurality of internal angles, including α, and σ. A first angle σ is defined at the first outward apex 24 between the struts 26, 27 and a second angle α is defined at the second outward apex 25 between the struts 28, 29. In some embodiments, the first angle α can be greater than the second angle σ. For example, the first angle α can be between 43° and 53°, or between 45° and 51°. The second angle σ can be between 31° and 41°, or between 33° and 39°. In some embodiments, the first angle α can be about 48°, and the second angle σ can be about 36°.

In a preferred embodiment, the tack 10' has an expanded outer diameter of 7.5 mm and the first angle α can be 47.65° and the second angle σ can be 35.56°. In such an embodiment, the plaque tack 10' can be formed from a tube stock with an initial outer diameter 4 mm. The tube stock can be expanded to 7.5 mm and then heat treated in that shape. In some embodiments, the plaque tack 10' can be made of a shape memory material and the heat treatment step can be to engrain that particular shape into the "memory" of the material. The plaque tack 10' can then be crimped or compressed and flash frozen in the compressed state to then be loaded onto a delivery device.

A beneficial feature of the tack 10' is that the angle of the struts as they meet at each apex can be controlled in at least one of an expanded and a contracted state. For example, the internal angles α, σ of the outward apices 24, 25 can be controlled to be within ±5% of a selected nominal value. This control can be achieved for example, in the expanded state during the heat treatment during the manufacture of the plaque tack 10'.

It has been found that control of the angles can beneficially offer relief from imperfections in the manufacturing process. In some cases, the control of other dimensions can be relaxed if these angles are sufficiently well controlled. By controlling these angles, production run quality can be improved. Such control has been found to enable repeatable, uniform, and balanced compressibility of the tack 10' during the crimping cycle of manufacturing. These factors increase production run repeatability and offer ease of volume manufacturing which results in a reduction in overall cost of the part.

In addition, control of the apex angles allows the plaque tack 10' to better distribute stresses along the circumferential members or rings 12. The control of apex angles can be used to control or distribute stresses within the ring 12, e.g., uniformly along the length of the struts or non-uniformly to a region that can more robustly respond to stress loading. By distributing stress along the strut, the problematic localized stresses on the tack 10', such as at vulnerable spots can be avoided during the expansion and crimping processes of manufacturing.

3. Inverse Tapering Struts

In some embodiments, such as that shown in FIGS. 5A-C, the width of one or more of the struts 26, 27, 28, 29 of the tack 10' can be different at different locations, e.g., can vary along the struts. For example, the struts can be tapered along their length. The taper can be the same or different along each strut or along each type of strut. For example, each circumferential member or ring 12 can be made up of a pattern of repeating struts, with each type of strut having a particular taper.

FIG. 5C shows that the ring 12 has a first strut coupled with a bridge 14 that is tapered such that a portion of the strut closer to the midline C (sometimes referred to herein as a medial portion or location) is narrower than a portion of the strut spaced farther away from the midline C (sometimes referred to herein as a lateral portion). A second strut is connected to the first strut at lateral ends of the first and second struts. The second strut can have the same or a different taper. For example, the second strut can also have a medial portion narrower than a lateral portion of the second strut. In addition, the second strut can be narrower overall than the first strut. A third strut can be connected to the second strut at medial ends of the second and third struts. The third strut can have a medial portion that is wider than a lateral portion thereof. A fourth strut can be connected to the third strut at lateral ends of the third and fourth struts. The fourth strut can have a medial portion that is wider than a lateral portion thereof. The fourth strut can have the same or a different taper from the third strut. For example, the fourth strut can wider overall than the third strut.

FIG. 5C schematically illustrates the differences in the widths of the struts in one embodiment. In some embodiments, the long struts 26 and the long strut 27 have the same width at the same axial position and the short struts 28 and the short strut 29 have the same width at the same axial position. The struts 26 and the strut 27 can have the same shape. The strut 28 and the strut 29 have the same shape in some embodiments. The shape of the struts 26, 27 can be different form the shape of the struts 28, 29. In some embodiments, the long strut 26 and the long strut 27 have different widths at the same axial position and the short strut 28 and the short strut 29 also have different widths at the same axial position.

In a preferred embodiment, the long struts 26, 27 are disposed at a first circumferential location of the tack 10' adjacent to one of the markers 22. In particular, the strut 26 has a medial end connected to or forming a portion of one of the inward apices 18 and a lateral end disposed away from the inward apex 18. The lateral end is coupled to the strut 27 at or adjacent to the outward apex 24. The strut 26 has a width W4 adjacent to the medial end and a width W2 adjacent to the lateral end. In this embodiment, the width of the strut 26 increases along the length thereof from the width W4 to the width W2. The increase in width along the strut 26 preferably is continuous along this length.

Also, the sides of the struts 26 can be sloped relative to a longitudinal axis $L_A$ of the strut 26. For example, a first side 48 disposed between the longitudinal axis of the strut 26 and the strut 27 can be disposed at an angle to (e.g., non-parallel to) the longitudinal axis of the strut 26. In another embodiment, a second side 46 of the strut 26 can be disposed at an angle to (e.g., non-parallel to) the longitudinal axis of the strut 26. In one embodiment, both the first and second sides 46, 48 of the strut can be disposed at angles to the longitudinal axis of the strut 26.

The strut 27 preferably also has different widths at different points along its length. In particular, the strut 27 can be wider in a generally lateral direction adjacent to the outward apex 24 than it is adjacent to the inward apex 19. As discussed above in connection with the strut 26, the strut 27 can have side surfaces that are angled relative to the longitudinal axis of the strut 27. The strut 27 can be tapered between its ends, e.g., having a continuously decreasing width along its length from wider adjacent to the outward apex 24 to narrower adjacent to the inward apex 19.

The strut 28 extends from the strut 27 or inward apex 19. The strut 28 can have a medial end that is wider than a lateral end of the strut 28 and can have different widths at different points along its length. The side surfaces can also be angled relative to the longitudinal axis of the strut 28.

Finally, a strut 29 can be connected to the strut 28 or outward apex 25 at a lateral end of the strut 29. The strut 29 can have a medial end that is wider than the lateral end thereof. The strut 29 can have a taper that is the same or different from the strut 28. For example, the strut 29 can be wider overall than the third strut.

In one embodiment, the strut 26 can have a width $W_2$ of about 0.12 mm at the lateral end near the outward apex 24 and a width $W_4$ of about 0.095 mm at the medial end near the inward apex 18 and the strut 28 can have a width $W_6$ of about 0.082 mm near the outward apex 25 and a width $W_8$ of about 0.092 mm near the inward apex 19. More generally, the change in thickness between W4/W2 expressed as a percentage can be between about 70% and about 90% more typically between about 75% and about 85%, and in certain embodiments about 80%. The tapering can also be inverted, e.g., with the struts tapered from the ends (e.g., lateral edges) toward the medial portion.

Figure 5D:
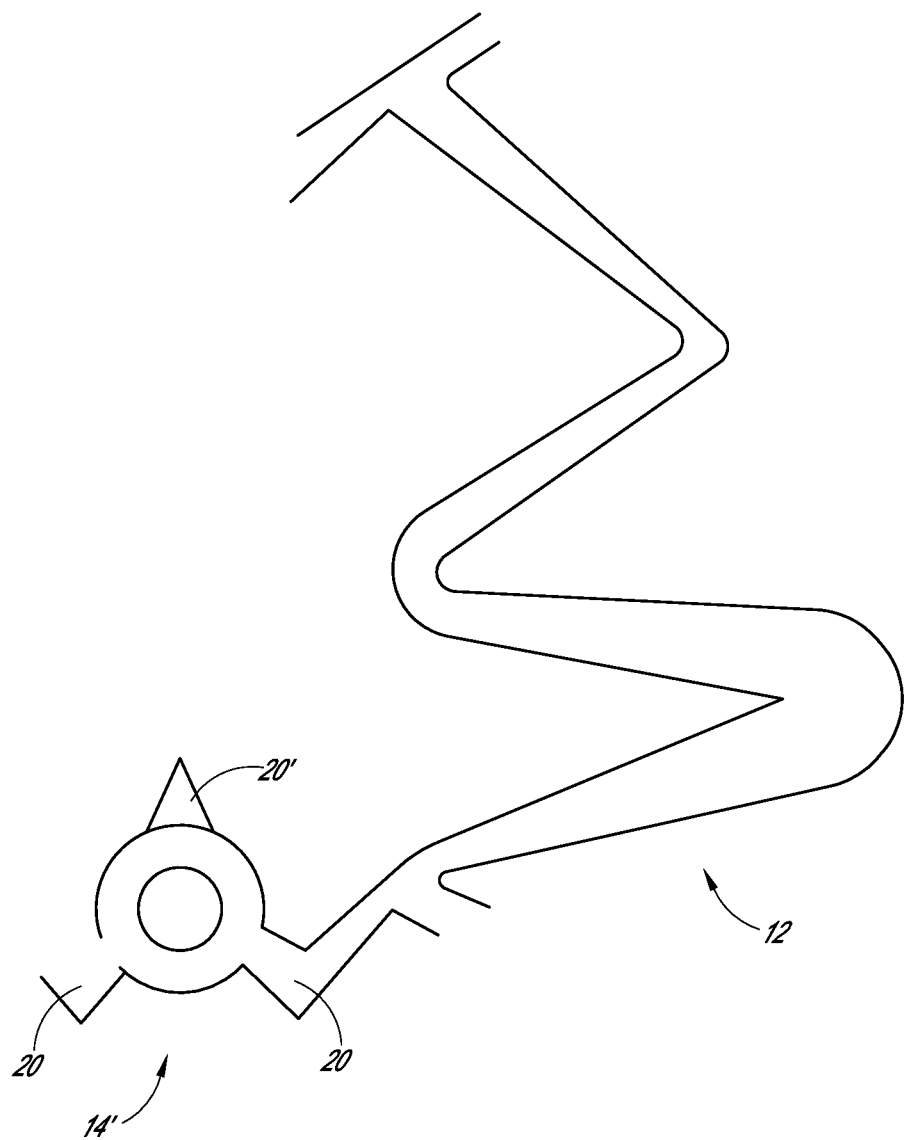
FIG. 5D shows a variation on the embodiment of FIGS. 5A-5C having an anchor disposed on a midline of the tack.
Figure 5E:
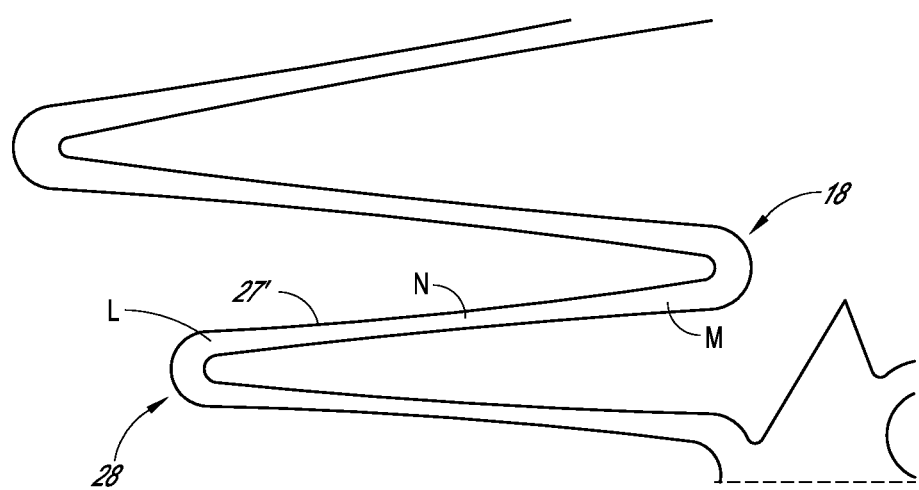
FIG. 5E shows a variation with struts that taper from wider at a lateral edge of a tack to narrower at a mid-section of the strut and/or from narrow at a mid-section of a strut to wider adjacent to a medial location of the tack.

FIG. 5E illustrates another variation in which the width of one or more of the struts of the tack can be different at different locations, e.g., can vary along the struts. For example, a strut 27' can be provided that is similar to the strut 27 except that the strut 27' is narrowest in a mid-section N. The strut 27' can have a lateral wide portion L adjacent to the outward apex 28 and a medial wide portion M adjacent to the inward apex 18. The width of the strut 27' reduces along the length thereof from the lateral wide portion L toward the medial portion M. In one embodiment, the strut 27' is continuously narrower along the length from the lateral end of the strut 27' toward the midline of the strut. The strut 27' can be narrowed such that the ratio of width at the midline to width at the lateral end of the strut 27', expressed as a percentage, is between about 20% and about 85%. In some embodiments, this percentage is between about 35% and about 75%. The tapering can be such that this percentage is between about 55% and about 70%. From the medial wide portion, the strut 27' can be narrowed along the length thereof. In one embodiment, the strut 27' is continuously narrower along the length from the medial end of the strut 27' toward the midline of the strut. The strut 27' can be narrowed such that the ratio of width at the midline to width at the medial end of the strut 27', expressed as a percentage, is between about 20% and about 85%. In some embodiments, this percentage is between about 35% and about 75%. The tapering can be such that this percentage is between about 55% and about 70%. The embodiment of FIG. 5E provides a greater range for compression and expansion in smaller diameter configurations. Smaller diameter configurations can be used in smaller body lumens, e.g., blood vessels. For example, a tack with this configuration can be formed out of 2.3 mm diameter tubing, whereas the embodiments of FIG. 5C are optimally formed out of 4.5 mm diameter tubing. The configuration of FIG. 5E can be used to make tacks that are suitable for a 4 French delivery device. Tacks configured as in FIG. 5E can have an unconstrained expanded size of between about 4.5 mm and about 6.5 mm. In some embodiments, devices including the configuration of FIG. 5E can have an unconstrained expanded size of between about 5 mm and about 6 mm, e.g., between about 5.5 and about 6.0 mm. One embodiment expands to about 5.7 mm when unconstrained.

A unique inverse taper or variation in width along the strut is achieved by inverting the orientation of the taper between the short struts 28, 29 and the long struts 26, 27. The longer struts 26, 27 go from a narrow width near the inward apices 18, 19 to a broader width near the high outward apex 24. Conversely, the shorter struts 28, 29 are the opposite with a broader width near the inward apices 18, 19 to a narrower width near the low outward apex 25.

Through strategic selection of the width of the struts, as discussed above, the plaque tack can distribute the stresses observed during compression and after deployment. This feature can also contribute to the control of the stress by distributing the region of stress more uniformly along the length of the strut. In some embodiments, it may be desirable to distribute the stress non-uniformly to regions more able to handle the stress.

4. Dual Amplitude Struts

As been discussed above, the ring 12 illustrated in FIGS. 5A-5C has an undulating sinusoidal pattern. The axial extent of the ring 12 can vary about the circumference of the ring 12, for example providing a plurality of amplitudes as measured by the distance from an inward apex to an adjacent outward apex. The undulating pattern can have one or more amplitudes, such as the dual amplitude configuration shown. In the dual amplitude configuration the plurality of struts 26, 27, 28, 29 extend between inward 18, 19 and outward apices 24, 25.

In some embodiments, the outward apices 24, 25 alternate between a high outward apex 24 and a low outward apex 25. In this context "high" corresponds to a larger distance H1 as measured from a central zone or midline C of the tack 10' and "low" corresponds to a smaller distance H2 as measured from the midline C (FIG. 5C).

The varying amplitude of the long and short sinusoidal struts described above can provide additional control of the plaque tack's functionality. In particular, it can enhance compression of the tack 10' to provide a greater change in circumference from the fully expanded configuration to a compressed configuration when crimped during manufacturing. Greater compressibility facilitates delivery in smaller vessels and a greater range of indication that can be treated because it enables a smaller crossing profile delivery system.

The height $H_1$, $H_2$ of the apices is measured from the center line C to the top of the respective outward apices 24, 25. The dual amplitude sinusoidal patterned plaque tack 10', such as that shown in FIGS. 5A-C, enables broad ranging conformable dimensions that can easily be scalable to different outer diameter designs. The open cell single column design allows broad range compression and expansion. This is partly due to the length of strut available for effective expansion. The ease of compression is associated with the position of the apices disposed $H_1$ and $H_2$ from the center of the tack, which permits these apices to compress at a different locations instead of at the same lateral location. If $H_1$ and $H_2$ of the apices are aligned (e.g., at the same axial location) they would press against each other during compression limiting the compression range.

The ranges of compression for the plaque tack 10' have been measured to 0.25 times nominal tube size in combination with ranges of expansion up to 2 times nominal tube size, although these are not the anticipated limits of the device. Combining these ranges the full range of compression has been measured at 0.125 times the heat treated outer diameter. As discussed above in SECTION II.B.2, in some embodiments the nominal tube size is 4.5 mm and the tube is expanded to 7.5 mm in the manufacturing process. According to some embodiments, the distance from the midline C of the device to the apex of the longer struts $H_1$ is approx. 3.0 mm, while the distance $H_2$ to the apex of the shorter struts is approx. 2.6 mm.

In addition to the enhanced compressibility range, the energy stored in the shorter amplitude struts offers additional control of the plaque tack 10' during the release phase of delivery within the blood vessel. As the catheter sheath is retracted, the longer struts are uncovered first followed by the shorter struts (FIG. 5C). This mismatch provides greater retention forces to maintain the plaque tack 10' in the delivery catheter and thus provides greater control of the plaque tack during delivery.

5. Centrally Disposed Anchoring and Elevating Structure

FIGS. 5A-5C illustrate that the plaque tack 10' can include centrally disposed anchors 20. While the anchors 20 are primarily for securing loose plaque, as discussed above, their placement and configuration enhance the control of the deployment and the performance of the tack 10' once placed inside the blood vessel.

As discussed above, the plaque tack 10' can be a self-expanding circumferential structure and the anchors 20 can be disposed on an outer portion of the tack. The anchors 20 can be coupled with any portion of the tack 10' but preferably are disposed adjacent to the midline C of the bridges 14 as discussed above. In one embodiment, the tack 10' includes two anchors disposed on either side of the midline C as illustrated in FIG. 5C. In another embodiment, a single anchor can be provided on the midline C. In a further embodiment, at least three anchors 20 can be provided, such as one on the midline and two on either side thereof as illustrated in FIG. 5C. The bridge 14 can have two anchors on one side and one anchor on the other side connecting the two other anchors, as shown in FIG. 5D. In FIG. 5D, an anchor 20' is located at the center of the tack 10' along its axial direction. This embodiment provides at least one anchor 20' that is located on both sides of the midline C. Also, the anchor 20' can be located on an opposite side of the marker 22 from the anchors 20. As such, plaque can be anchored from a plurality of directions, e.g., a plurality of circumferential directions. In a further embodiment, the anchors 20 are not present and a single anchor 20' located on the midline C is provided. The embodiment illustrated in FIGS. 5A-C could also be modified to include one or more anchors on either side of the marker 22, where anchors are currently only shown on one side.

In one aspect, the plaque interaction of the tack 10' is primarily provided by the anchors 20 and to a lesser extent the bridges 14. In some embodiments, the anchors can have a preferred penetration length into the plaque of 0.01 mm to 5 mm. In certain variations, the penetration length is within a range of about 0.03 mm to about 1 mm. In other variations, the penetration length is within a range of about 0.05 mm to about 0.5 mm. The bridges 14, which can be disposed at alternating inward apices, as discussed above, can be configured to reside on a tangential plane of a cylinder when the tack 10' is fully expanded and not being deformed by an outward structure. The tangent configuration causes the anchors 20 to project outward toward from the cylindrical surface of the tack 10'. In this outward projecting position, the anchors are adapted to engage plaque or other vascular deposits causing the vessel to vary from its unobstructed fixed state, e.g. to be out-of-round.

The tangential projection of the anchors and bridges also advantageously enhances the control of the tack 10' upon deployment. A technique for deploying the tack 10' involves positioning the tack in a hollow catheter body. When positioned in the catheter body, the tack 10' is compressed to a compressed state. The rings 12 are highly conformal due to their construction, discussed above. As a result, the rings fully appose to the inner luminal surface of the hollow catheter body. In contrast, the bridges 14 and anchors 20 are more rigid and therefore are less conformal and as a result bite into the inner luminal surface of the catheter body. This creates a retention force within the catheter and limits unintended movement of some or all of the tack 10' toward a catheter deployment zone.

In some embodiments, the retention force of the barbs 20 is maintained or increased after partial deployment of the tack 10'. In particular, a region of relatively high flexibility can be provided at the junction of the bridges 14 and the rings 12. While high flexibility sections of stents can be areas of concern, such is not the case in the plaque tack 10' for reasons discussed below. The flexible region can have any material property or structure to enhance its flexibility at least compared to that of the bridges 14 such that upon movement of the ring 12 on the leading edge of deployment, the tangential configuration and tendency of the anchors 20 to bite into the hollow elongate catheter body is not diminished. Such is the case even though the leading edge ring 12 may expand to at least one-half of its fully expanded size.

As shown, the bridge 14 is connected to each ring at the inward apex 18 where at least a portion of the bridge 14 can be aligned, partially or substantially aligned with one of the struts that make up the ring 12 as has been described. For example, as shown, the bridge 14 is aligned with a high amplitude sinusoidal section of the pattern. The region of relatively high flexibility can be disposed between the inward apex 18 and the bridge 14.

In certain embodiments, expansion of the ring 12 may even cause the anchors 20 to rotate outward to increase the retention force in the catheter body. For example, expansion of the strut 26 may cause an inward deflection of the inward apex 18. While ring 12 is expanding a slight rotation of anchors 20 may occur which may cause a torqued outward deflection of the leading anchor and a corresponding torqued outward deflection of the trailing anchor. With reference to FIG. 5C, if the depicted ring 12 is first expanded upon moving out of the hollow catheter body, the anchor 20 to the right of the midline C may be deflected inwardly toward the central axis of the catheter body but the anchor to the left 20 will be deflected outward to increase the retention force thereof. Thus, the plaque tack 10' may be retained in the catheter during such partial expansion. Due to this feature the plaque tack 10' can be uniformly placed, as discussed further below in Section II.B.8.

The out-of-cylinder nature of the bridges 14 and anchors 20 also provide benefits to the deployed state. In particular, in some embodiments in an expanded state, the plaque anchors 20 are disposed radially outwardly of a cylindrical surface formed by the rings 12. The degree of out-of-cylinder can depend on the application, but in general may be sufficient to space at least a portion of the cylindrical surface from the inner walls of the vasculature when deployed. As such, the anchors 20 or the anchors combined with the rings 12 can be configured as focal elevating elements, which are discussed below in SECTION III.

As the plaque tack 10' expands within a blood vessel, the struts will engage the vessel wall and/or plaque. It is anticipated that in most situations, at least some of the struts will be deformed in response to irregularities of shape within the blood vessel. At the same time, the bridges 14 are less deformable and thus will resist such deformation retaining a circular configuration. The outward forces that are applied by the strut members are transferred into those areas that are in contact with the blood vessel wall. In some cases, when the tack 10' conforms to an irregularly shaped blood vessel lumen, the rigid central anchors become the region for blood vessel contact. The cumulative outward force of the struts in the rings 12 are applied through the bridges 14 to the anchors. Adjacent struts share their load with the contact region pressing the blood vessel into an enlarged configuration, such as a conformed circle.

Such a configuration can provide benefits such as helping the plaque tack 10' to remain in place after delivery and allowing the plaque tack 10' to respond dynamically to the movement and pulsing of the blood vessel itself. In addition, this configuration can have the benefit of reducing cellular response and device fracture by limiting strut fatigue and associated micro friction loading at the tack-blood vessel interface.

In some embodiments, the bridge 14 can include one or more anchor. In some embodiments, the bridge can be formed entirely of anchors.

After deployment of the plaque tack 10', the surgeon has the option of placing an angioplasty balloon at the site of the tack and inflating the balloon to press the anchor or anchors 20 into the plaque and/or wall of the blood vessel.

6. Flat Midline Markers

As discussed above, the plaque tack 10' has one or more markers 22. In one embodiment, a series of radiopaque markers 22 can be located on the tack 10'. In some embodiments, the radiopaque markers 22 are at the midline C of the device. The radiopaque markers 22 can be disposed between the two circumferentially oriented sinusoidal members or rings 12.

In some embodiments, the radiopaque markers 22 (e.g., platinum or tantalum) can be disposed adjacent to the plaque anchors 20. The radiopaque markers 22 can have one of many different shapes or configurations. In some embodiments, the radiopaque markers 22 have a planar or flat structure. As shown in FIG. 5C, each marker 22 is coupled with, such as by being press-fit or riveted into, a circular eyelet producing a flat leveled surface with the eyelet. The markers 22 offer clear visibility of the tack 10' in the catheter delivery system and provide guidance to the clinician for accurate placement during the procedure.

According to certain delivery methods, due to the co-placement of the anchors 20 and the markers 22 at the bridges 14 between the sinusoidal rings 12, the markers 22 can offer a visible clue to the clinician of the point when the release of the device will take place. For example, once the markers 22 meet a marker strip located at the tip of a delivery catheter sheath the full device can be deployed.

Figure 1:
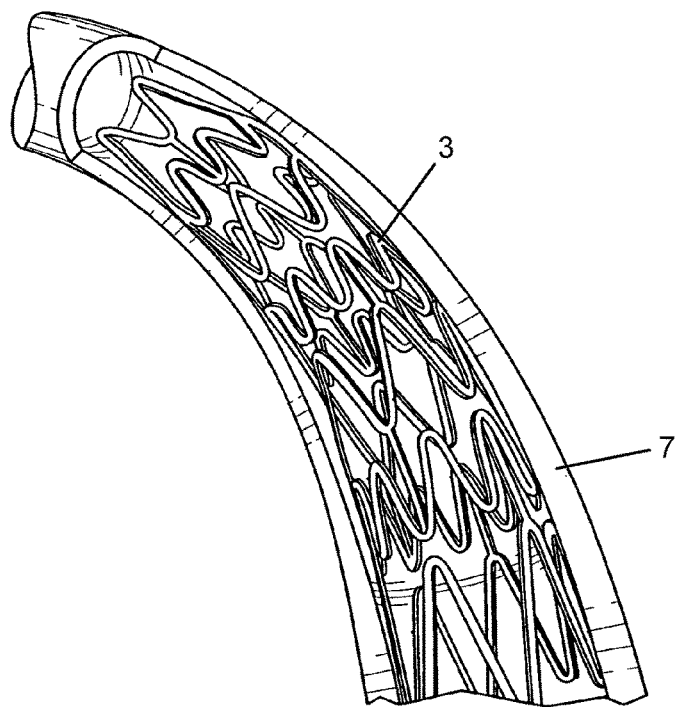
FIG. 1 illustrates the use of a stent installed after angioplasty as conventionally practiced in the prior art.

Referring now to FIG. 5C1, a schematic representation of a tack 10' is shown. As illustrated, the anchor 20 has an increased material thickness verses the rest of the tack. This results in the anchor 20 also having an increased radiopacity as compared to the rest of the tack, effectively converting the anchor into a marker.

7. Simultaneous Device Placement in the Vessel

The plaque tack 10' can be configured for simultaneous placement within a blood vessel. Simultaneous placement of the plaque tack 10' can be defined as the entire plaque tack 10' being released from the delivery catheter prior to any of the distal apices of the plaque tack 10' contacting the blood vessel lumen where it is to be placed. This event can occur when the anchors 20 are completely uncovered by the catheter sheath allowing the entire plaque tack 10' to expand against the lumen wall of blood vessel. The struts 26, 27, 28, 29 can be free floating, e.g., spaced from the vessel wall or applying negligible force to the wall, such that they do not contact the lumen wall prior to simultaneous placement. For example, the anchors 20 may have the effect of spacing a portion or substantially all of the struts 26, 27, 28, 29 from the vessel wall. Other forms of focal elevating elements are discussed below that can be used to space the tack 10' from the lumen wall.

Simultaneous placement offers the clinician the ability to control placement up until the markers 22 and/or anchors 20 are uncovered which can generate a full expansion event (struts adjacent to or contacting the lumen wall). In some embodiments, the full expansion event does not occur until the anchors 20 are uncovered due mainly to internal forces of the tack 10' urging the anchors 20 to engage the delivery sheath described above.

Another benefit of simultaneous placement is the reduction of any inadvertent dragging or pushing of struts against or along the lumen surface during the placement of the plaque tack 10'. Due to the complexity and variation of disease, location of placement, and dissections morphology, the ability of the outer surface of the plaque tack 10' to contact the lumen wall all at the same time is dependant on the deployment circumstances. However, the ability of the plaque tack 10' to contact the lumen wall completely upon release from the catheter sheath within fractions of a second has been observed.

8. Low Slope Force Curve

Figure 6A:
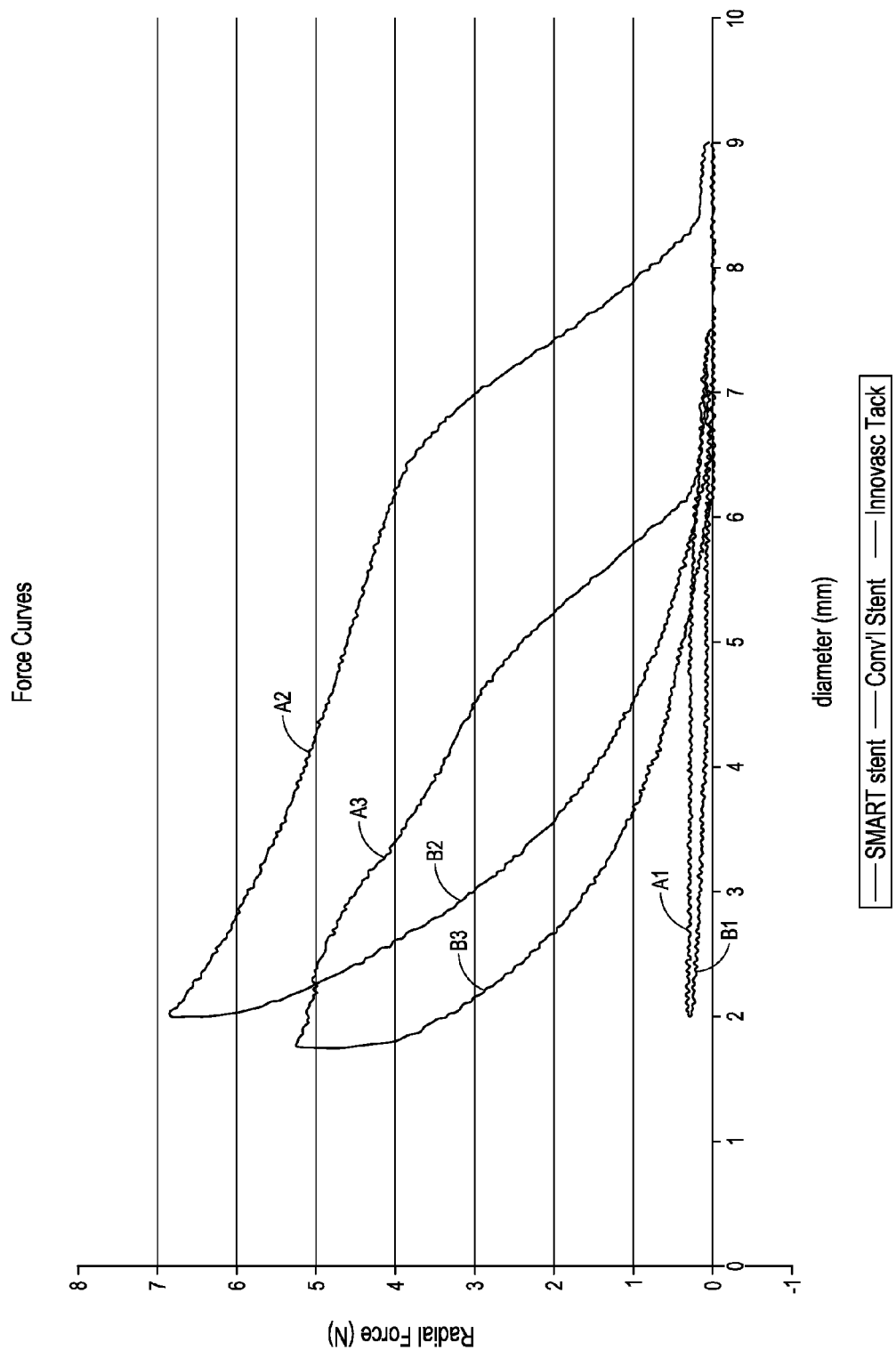
FIG. 6A is a chart comparing the expansion forces of a plaque tack to a stent.

Another unique aspect of the plaque tack 10' is that it can be configured with a force curve with an extended area having a low slope. A force curve, such as that illustrated in FIG. 6A, shows the amount of expansive force exerted by a self expanding plaque tack 10' or stent when moving from a compressed state to an expanded state. The expansion force of a device can be a factor in choosing the correct device to be placed in a particular blood vessel.

Still referring to FIG. 6A, the force curves of a SMART stent (i.e., a S.M.A.R.T.® Control transhepatic biliary stent by Cordis Corporation), another conventional stent, and a plaque tack having the wall pattern illustrated in FIG. 5A. The chart shows the radial force in Newtons (N) on the y-axis and the outer diameter of the device in millimeters (mm) on the x-axis. As the device is expanded or moved from the compressed state to the expanded state, the outer diameter increases. Because the devices are self expanding, they have a set amount of stored potential energy. When released, the potential energy is converted into kinetic energy as the internal forces try to restore the device to its expanded shape. The kinetic energy can then have an impact on the blood vessel when the device is implanted. Also, if the plaque tack 10' is not fully expanded a generally constant force will be applied to the vessel wall that corresponds to remaining potential energy stored in the tack 10'.

FIG. 6A shows a first dark line A1 showing the compression of a 7.5 mm plaque tack 10' from approximately 7.5 mm to approximately 2 mm of compressed diameter. After a gradual slope region between about 7.5 mm and about 6 mm, the slope of the force for each incremental reduction in diameter is greatly reduced, providing a narrow band of force required to fully compress the tack 10' from about 6 mm to about 2.0 mm. This portion of the force curve is very flat, meaning that the applied compression force does not greatly increase as the tack 10' approaches its fully compressed state. The force curve of the plaque tacks 10' upon expansion is illustrated by a dark lines B1 extending from 2.0 mm of compressed diameter to about 7.5 mm of expanded diameter. This portion of the curve can be thought of as the working portion, in which the force on the Y-axis is the force that the plaque tack 10' would apply to a vessel wall upon expansion. For example, if the plaque tack 10' were deployed in a vessel lumen having a bore of about 5.0 mm, the outward force of the tack 10' on the wall would be well under 1.0 Newton (N). Over a range of about 2 mm, the range of outward force is less than about 0.05 N+/− about 30%.

FIG. 6A shows in a dimmer line A2 the crimp performance of a SMART stent in a similar test. As discussed above in connection with other prior art stents, the SMART stent is a longer structure than the plaque tack 10'. In particular, the S.M.A.R.T.® stent tested was 40 mm long with a 8 mm unconstrained outer diameter, whereas the tack that was tested was 6 mm long with a 7.5 mm unconstrained outer diameter. However, it is believed that the comparison between the plaque tack 10' and the SMART stent illustrates a difference that would still manifest with a comparable length version of the SMART stent. As shown on the graph, the line B2 has a much higher crimp force in a range from just over 8 mm to about 6.5 mm. At about 6.5 mm, the slope of the crimp force decreases and the crimp force increases at a much slower rate. The outward force at the fully crimped state is much higher. Although the fully crimped state of the SMART stent corresponds to a smaller diameter, the crimp force for a comparable diameter is much higher on the SMART stent. Line B2 illustrates the working zone of the SMART stent that was tested. Line B2 shows the outward force over the range of expansion from about 2 mm to about 6 mm. As can be seen, the slope of line B2 is much greater at all points along its range between 2 mm and 6 mm. The practical effect of this higher slope is that the SMART stent is much more sensitive to changes in the bore size of the vessel into which the expanded plaque tack 10' is deployed.

As can be seen in FIG. 6A, in some embodiments, a low slope of the force curve can be essentially flat over about a 3 mm outer diameter expansion range. In other embodiments, a low slope of the force curve can be over a 2.5 mm outer diameter expansion range with a change in force of change less than 1 N. Factors in the ability of the tack to have a broad range where the radial forces change less than 1 N include the midline anchors, dual amplitude struts, and the varying strut thicknesses, discussed above.

FIG. 6A illustrates another conventional stent having a compression curve A3 and an expansion curve B3. The SMART stent is a widely used stent pattern. The curves A3, B3 represent another conventional stent design. Although the curves A3, B3 have lower peak compression force at the left-hand side of the curve, the slope is still dramatically higher over the range of use than is the tack illustrated by curve A1, B1.

The tack is radially self expandable through a range of at least about 2 mm, generally at least about 3 mm and typically through a range of at least about 4 mm or 5 mm, while exhibiting a radial expansion force of no more than about 5 N at any point throughout the range. In some embodiments, the maximum radial expansion force throughout the expansion range is no more than about 4 N and preferably is no more than about 3 N. In one embodiment, the tack is expandable over a range of at least about 3 mm (e.g., from about 3 mm to at least about 6 mm) and the radial expansion force is less than about 3 throughout that range. Generally the change in expansion force will be no more than about 3 N and preferably no more than about 2 N throughout the expansion range. In one embodiment, the expansion force drops from no more than about 2 N at 3 mm diameter to no more than about 1 N at 6 mm diameter. Typically the difference between the radial force of compression and the radial expansion force at any given diameter throughout the expansion range is no more than about 4 N, generally no more than about 3 N, preferably no more than about 2 N and in one embodiment is no more than about 1 N. In one implementation, the tack is expandable throughout a range which includes 3 mm through about 6.5 mm and the difference between the compression force and expansion force at each point along the compression/expansion range differs by no more than about 2 N and preferably by no more than about 1 N.

In general, the outward force of the plaque tack 10' is preferred to be as low as possible, while providing sufficient force to hold the plaque against the lumen wall through a wide range of luminal diameters. When force is elevated, e.g., by two to three times the sufficient holding force, adverse side effects can occur. These can include irritating the cells of the vessel wall that are in contact with the device, which can lead to re-stenosis. Although a very low force device is preferred for the typical treatment, higher force devices may be useful where loose plaque is found at calcified lesions.

One advantage to having a slow change in force as the device is expanding is the ability to predict the energy that the blood vessel experiences independent of the lumen diameter. Another value would be the reduction of necessary inventory for hospitals. For instance, it has been found that two part sizes of the tack 10' shown in FIGS. 5A-C can be used for plaque tacking treatments in blood vessels located throughout the leg, from hip to ankle. This is believed to be due in great part to the tack 10' having a slope of less than −0.3 N/mm.

C. Plaque Tack Design Parameters

One purpose of the plaque tack described herein, as distinct from traditional stenting, is to reduce the amount of implanted foreign material to a minimum while still performing focal treatment of the blood vessel condition so as to cause a minimum of blood vessel wall reaction and adverse post-treatment restenosis. The plaque tack is designed to have substantially less metal coverage and/or contact with the blood vessel surface, thereby inciting less acute and chronic inflammation (See FIG. 6B). Reduced contact area of implanted material against the blood vessel wall is correlated with a lower incidence of intimal hyperplasia and better long-term patency. Substantially reduced length along the axial distance of the blood vessel permits a more targeted treatment, correlates with less foreign body coverage of the blood vessel surface, avoids covering portions of the surface that are not in need of coverage, and correlates with both early and late improved patency of blood vessel reconstructions.

The plaque tack can be deployed only where needed to tack down plaque that has been disrupted by balloon angioplasty or other mechanisms. Rather than cover an entire area of treatment, the plaque tack can be placed locally and selectively, for example, not extending into normal or less diseased artery segments (See FIG. 6B). This permits the blood vessel to retain its natural flexibility because there is minimal to no scaffolding when a small profile tack is used locally or even when multiple tacks are spaced apart over the area of treatment. Still further reduction in the pressure profile can be achieved by using "points-of-contact" to achieve higher pressure at focal points and lifting the neighboring strut section away from the blood vessel wall to reduce the overall load of the outward pressure elsewhere on the tack strut structure.

One parameter for design of a plaque tack is having a tack axial length to expanded diameter (L/D) ratio of no more than about 2.0, often no more than about 1.5 and in some implementations no more than about 1. In one embodiment, the tack has about an L/D ratio of 0.8. That is, the length of the tack along the axis of the blood vessel is about equal to or less than the expanded diameter of the tack. The preferred plaque tack is thus shaped like an annular ring or band, whereas the typical stent is shaped like an elongated tube. The small-profile tack can thus be used locally for targeted treatment of disrupted regions of the blood vessel surface with a minimum of foreign material coverage or contact. Tests show that a plaque tack with an axial length/diameter ratio≤1 causes almost no biological reaction or subsequent blood vessel narrowing in comparison to a traditional stent where the axial length is greater than the diameter, and usually much greater. Tests indicate that device L/D≤11 results in a reduction in scaffolding much less than that of the typical stent and causes less arterial wall reaction. For application at sites of small dissection after balloon angioplasty, a plaque tack of minimal footprint may be used such as a single, thin ring-type tack with an L/D ratio in the range of 1/10 to 1/100.

Studies on stenting have shown that the axial length of a stent is correlated with a tendency for occlusion in multiple vascular territories. The more stent axial length that has been placed, the higher likelihood that the reconstruction will fail. The axial length of a stent is also directly linked to the frequency and tendency of the stent to break when placed in the superficial femoral artery. The medical literature indicates that the superficial femoral artery performs like a rubber band, and it is likely that changes to the natural elongation and contraction of the superficial femoral artery play a significant role in the failure mode of superficial femoral artery stents. In contrast, the small-profile plaque tack can be implanted only in local areas requiring their use, thereby enabling the blood vessel to retain its natural flexibility to move and bend even after the surface has undergone tacking. Multiple tacks may be implanted separated by regions free of metallic support, thereby leaving the artery free to bend more naturally.

Outward radial pressure exerted on the blood vessel wall can also be substantially reduced by the small-profile tack design, even when multiple tacks are used in a spaced-apart configuration. To minimize this outward force while still providing the required retention of dissections against the arterial wall, a series of anchor barbs or focal elevating elements can be utilized. The presence of these features applying focal pressure to the wall of the artery allows the rest of the tack to apply minimum outward force to the artery wall. The points which apply the pressure can be very focal, and this is where the most force is applied. The focal nature of the application of the pressure exerted by the tack also minimizes the structural effects of the device. Uniformly distributed anchors or focal elevating elements can provide a distribution of radial energy maximizing the tendency to form a circular lumen.

Another important parameter for design of a plaque tack is the ratio of Vessel Coverage Area (C) to Total Vessel Surface area (TVS). In one definition, the value C is the length of the prosthesis (e.g., stent or tack) times the average circumference of the vessel in which it is placed and the value TVS can be the length of the lesion or area requiring treatment times the same nominal circumference. This can also be simplified to a ratio of total length of the prosthesis when expanded to the nominal circumference divided by the length of the lesion in the vessel. These concepts can be applied to one tack device or when several spaced-apart tack devices are placed across the length of a blood vessel treatment area. Where multiple stents or tacks are used, a simplified ratio could be total non-overlapping length divided by lesion length or could be the sum of the length of the prostheses divided by the sum of the length(s) of the lesion(s). For a plaque tack, the C/TVS ratio is in the range of about 60% or less, whereas for a stent it can be 100% or more (if applied to overlap the treatment site).

For a focal lesion, the conventional treated vessel length is X+10 mm to 20 mm where X is the length of the lesion and the added length is adjoining on normal or less diseased artery proximal or distal to the lesion. In traditional stenting the entire treated vessel length would be covered with a stent. For example, in the case of a 2 cm lesion, the treated vessel length would be 3 to 4 cm (usually a single stent of this length would be selected), so that C/TVS is 150%-200%. In contrast, with tack placement about ½ of X would be covered, and none of the adjoining normal or less diseased artery would be treated. For example, in a 2 cm lesion, approximately 1 cm would be covered, so that the C/TVS ratio is about 60% or less. An advantageous aspect of this innovative approach is placement of bands only in regions of dissections requiring vascular tacking.

As described previously, in some embodiments, a tack device 10' is formed with rings or mesh bands 12 connected by longitudinal bridge members 14 (FIG. 5A). In the figure, the tack 10' is shown compressed for delivery in a blood vessel. When expanded, the diameter of the tack device can be about equal to the axial length of the tack device.

Figure 6B:
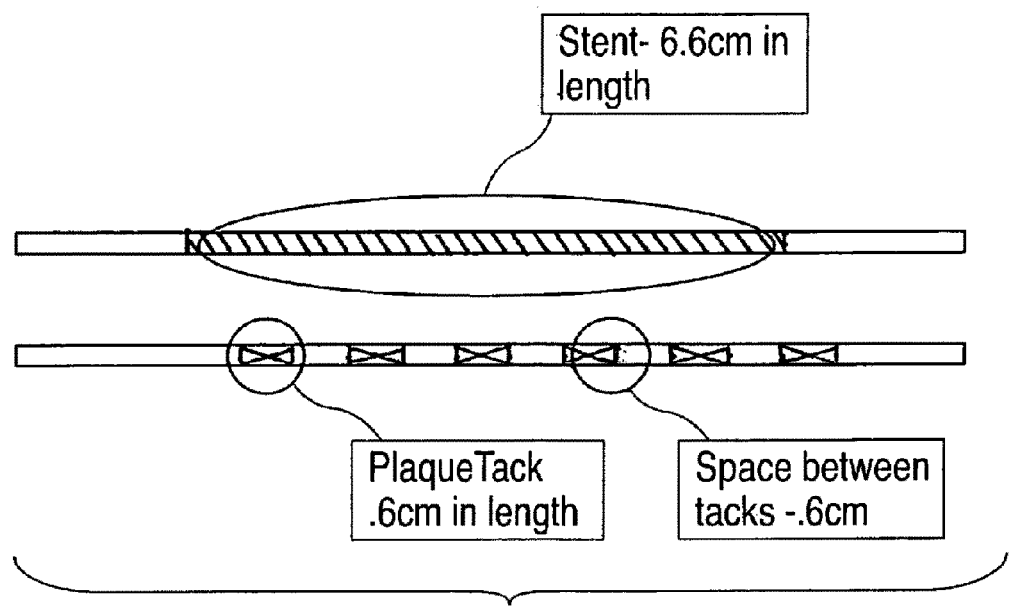
FIG. 6B illustrates the use of multiple plaque tacks which are spaced apart over the length of a treatment site as compared to a typical stent.
Figure 7A:
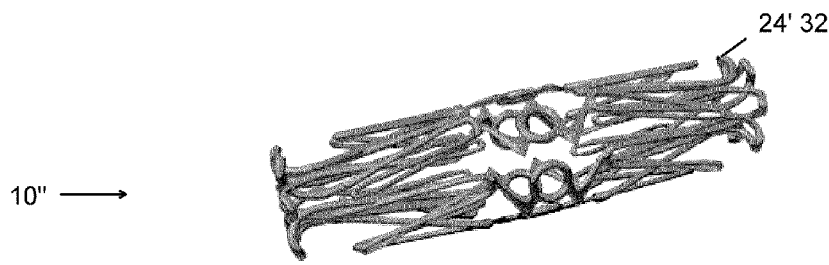
FIG. 7A shows another embodiment of a plaque tack in a fully compressed state.
Figure 7B:
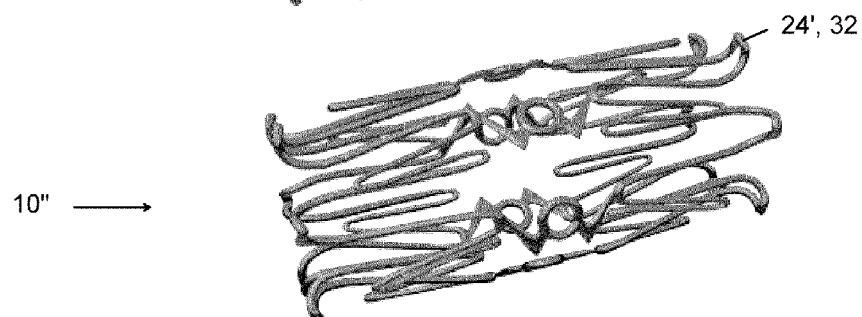
FIG. 7D shows the plaque tack in a fully expanded state and FIGS. 7B and 7C show the plaque tack in states of expansion between the fully compressed and expanded states.
Figure 7C:
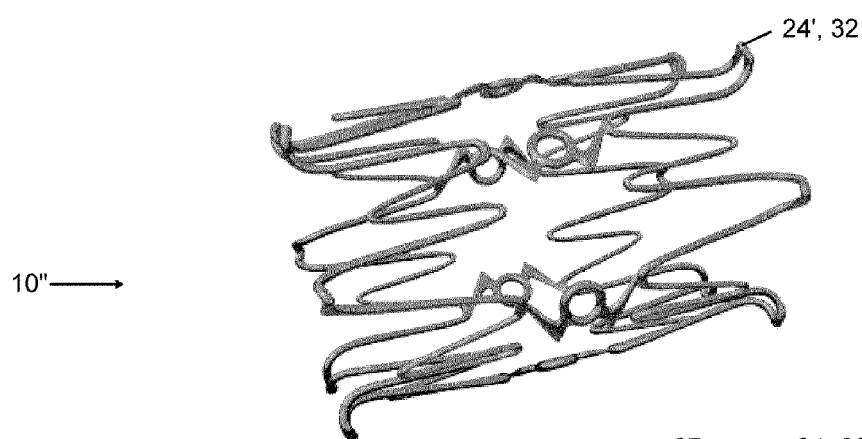
Figure 7D:
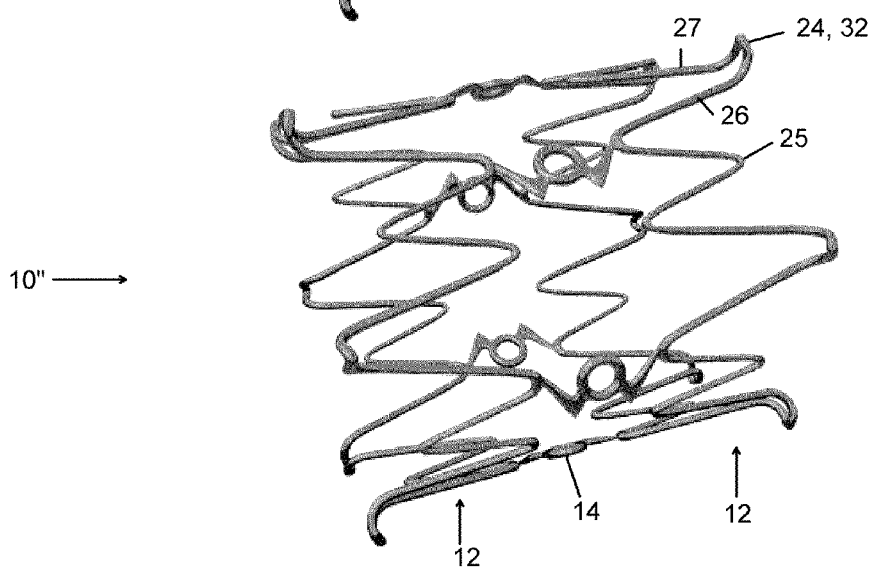

FIG. 6B illustrates the use of multiple tack devices which are spaced apart over a length of blood vessel at a treatment site as compared to a typical stent. Preferably, the spacing between tack devices is at least the axial length of the tack device. Note that the spacing between adjacent tack devices leaves untreated vessel area. A typical stent is shown in the upper part of the figure compared to the use of 6 spaced-apart tack devices at the bottom part of the figure. In this non-limiting example, the overall length of treatment area is 6.6 cm (the same length of the stent) while each band is shown as 6 mm long separated by 6 mm spaces. Therefore, the Vessel Coverage Area for the stent is the same as Total Vessel Surface area (=6.6 cm×0.6π, or 12.44 cm$^2$) which gives a C/TVS ratio of 100%. For the series of spaced-apart tack devices, C is equal to 6×0.6 cm×0.6π, or 6.78 cm$^2$, while TVS is 12.44 cm$^2$, therefore the C/TVS ratio is equal to 54.5%.

When two or more stents need to be employed over an extended length of treatment site, it has been a conventional practice to overlap adjoining stents to prevent kinking between stents. Due to the increased metal lattice, the region of overlap becomes highly rigid and noncompliant. This noncompliant doubly rigid region further limits the natural arterial flexibility and increases the tendency for restenosis. Stent fractures occur more frequently in the superficial femoral artery where this bending has a high frequency and are common when multiple stents are deployed and overlap. Stent fractures are associated with a higher risk of in-stent restenosis and re-occlusion. In contrast, the plaque tacks are designed to be applied in local areas and not to be overlapped. Optimal spacing is a minimum of 1 tack axial length apart for tacks. This permits the artery to maintain its flexibility, and only a half or less of the treated length of the artery will be covered with metal. It should be noted that in the case where restenosis occurs after tack placement the overlapping of the entire treated length with a stent still allows the stent to retain its patency. This is due to the repeated pattern of regions where no tacks are placed offering regions of relief and the artery to flex.

The literature in the industry has noted that important factors in stent design may be the ratio of Relative Metal Surface Area (RMS) and the number of longitudinal segments in the device structure, for example, as presented by Mosseri M, Rozenman Y, Mereuta A, Hasin Y, Gotsman M., "New Indicator for Stent Covering Area", in *Catheterization and Cardiovascular Diagnosis,* 1998, v. 445, pp. 188-192. More particularly, for a given metal surface area, a higher number of longitudinal segments (each of which is thinner) can reduce the size of the gap between adjacent segments, reducing the tendency for prolapse. As adapted from the RMS measure, an equation for Effective Metallic Interface (EMI) may be used to compare the embodiment of the tack device with longitudinal bridging members to a typical stent, as follows:

$$EMI = \frac{(1+n^2)C}{\sum_{s=1}^{x}(lw)_S}$$

Where x is the number of sections of metal, l is an individual metal section length, w is an individual metal section width, C is the vessel coverage area underneath the device (lumen surface), and n is the number of bridge members longitudinally connected between circumferentially oriented segments. The summation found in the denominator can be interpreted as the total metal surface area. The embodiment of the tack device with longitudinal bridging members has an EMI≤10, whereas the EMI of a typical stent would be several times greater. This low EMI is due to the nature of the tack design having a small foot-print and minimal longitudinal bridges while a stent typically has a large foot-print and would be a multiple several times that.

Figure 9:
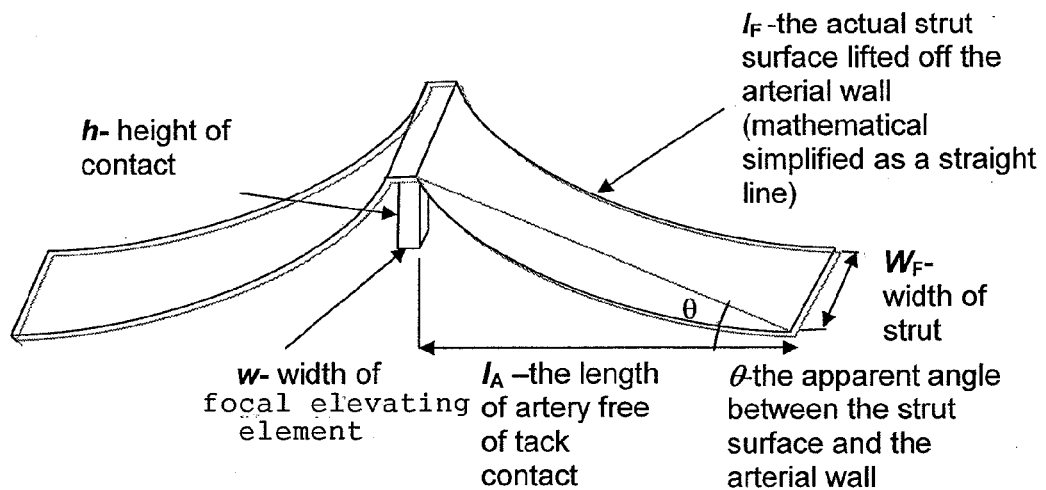
FIG. 9 is a schematic diagram illustrating the variables for computing the elevated tack surface due to the use of focal elevating elements in a plaque tack device.

To further reduce the EMI through the inclusion of lift-off-bump features (such as anchors, barbs, or focal elevating elements), an improved $EMI_F$ can be obtained for the Tack Effective Metal Interface as provided with floating elements (see FIG. 9). $EMI_F$ can be defined as:

$$EMI_F = \frac{C(1+(n-n_F)^2)}{\sum_{s=1}^{x}(lw - l_F w_F)_S}$$

Where all variables are the same as those in the EMI equation with the addition of $l_F$ is an individual metal section length that is not in contact with the artery (floating off the artery), and $w_F$ is the width of the same section. If no floating sections exist then $n_F=0$ and $l_F w_F=0$ and therefore $EMI_F=EMI$.

The inclusion of metal sections that are floating (floating length $l_F$, floating width $W_F$, and number of floating bridges $n_F$,) reduces the EMI further which is captured mathematically as a summation with negative variables in the $EMI_F$ equation.

The presence on the plaque tack of lift-off-bump features (such as anchors, barbs, or focal elevating elements) minimizes the pressure of the overall structure upon the blood vessel wall by transferring regional outward forces to focal pressure points, thereby applying a higher pressure at the focal points. The presence of the lift-off-bump features applying focal pressure to the artery wall allows the rest of the tack to apply minimum outward force to the artery wall. Wherever the lift-off-bump features are placed, the outward radial energy is maximized at that region, producing a slight outward bowing of the arterial wall. The outward bowing can be used for arterial shaping or molding, for example, 5 or more uniformly distributed focal points can be used to form a circular lumen. Circular lumens offer additional benefit from the standpoint of the vessel wall interaction, independent of the vascular injury.

In any of the embodiments herein described, the plaque tack device may be made from Nitinol, silicon composite (with or without an inert coating), polyglycolic acid, or some other superelastic material, as well as stainless steel, tantalum, a cobalt chromium alloy, bioabsorbable or bioresorbable materials (including bioabsorbable/bioresobable metals) or a polymer. The strip of material can be created from ribbon, round or rectangular wire or a sheet of material processed through photolithographic processing, laser or water cutting, chemical etching or mechanical removal of the final shape, or the use of bottom up fabrication, for instance chemical vapor deposition processes, or the use of injection modeling, hot embossing, or the use of electro or electroless-plating. It may be fabricated from metal, plastic, ceramic, or composite material.

The plaque tack device is designed to be inherently self-aligning, i.e., its mechanical installation can accommodate small misalignments. By reducing stress in the strut members while gripping the arterial wall in the center of the design, the tack self aligns with the arterial longitudinal axis. Design features that offer stress relief and provide uniform distribution of the unfolding struts include narrow spacing of the anchors, non-uniformly thick struts, and anchors heads that are angled to reduce device from springing forward during delivery. As discussed above, circumferentially oriented anchors located at each bridge member offer gripping force with the catheter tip and embedding features when lying on the artery wall. These design features serve to facilitate placing the tacks in specific locations within diseased blood vessels.

III. Improvement of Focal Elevating Elements

FIGS. 7A-D show a plaque tack 10" that is similar to that of FIGS. 5A-C except as discussed below. In particular, the plaque tack 10" includes a feature that reduces the amount or character of interactions between the plaque tack 10" and the vasculature by elevating a portion of the plaque tack 10" off of the vessel wall when deployed.

Figure 8:
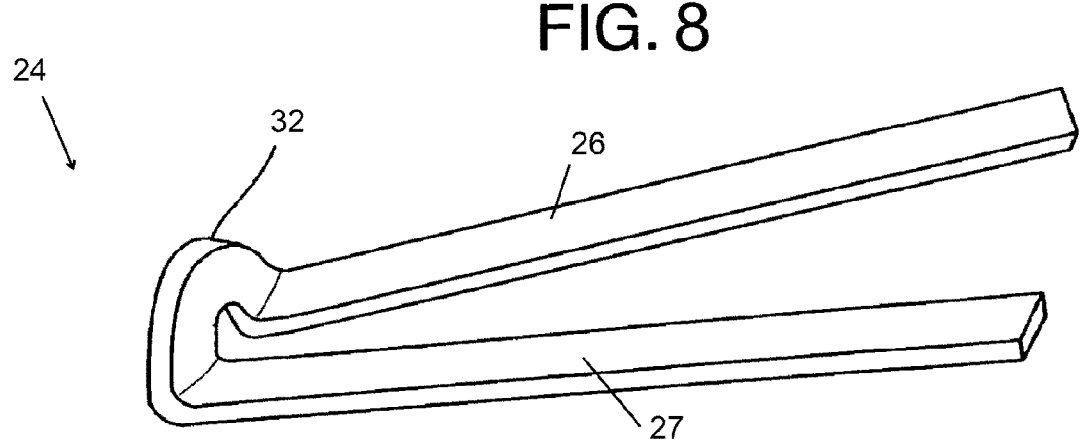
FIG. 8 is a schematic view of the focal elevating element of a plaque tack in FIGS. 7A-D.

In particular, the high outward apex 24' formed by the struts 26 and 27 is bent or turned upwards, or radially outwards, to form a focal elevating element (FEE) 32. FIG. 8 shows a schematic view of the FEE 32. In this embodiment, the high outward apex 24' is bent to form an angle with the struts 26 and 27. In this way the FEE 32 can help minimize the amount of the tack 10" that is in contact with the plaque and/or vessel wall while also localizing the forces at few points to more securely place the plaque tack 10". These as well as additional benefits will be described in more detail below.

A plaque tack devices may be provided with focal elevating elements on the annular periphery of the device. The focal elevating elements are distinguished from the anchors and barbs generally having greater plaque or arterial wall penetration to anchor or stabilize the tack in the blood vessel.

The focal elevating elements may or may not penetrate but still offer regional strut elevation and are preferably placed at apices of struts or periodically along (e.g., perpendicular to) strut lengths. For both anchors and focal elevating elements the size of the interface between the tack and the arterial wall is preferably equal to or shorter than the strut width in at least one direction. The focal elevating elements can be similar to anchors but either do not penetrate or penetrate the tissue only slightly, thereby minimizing the amount of material surface area in contact with the plaque, and offer a set of relief sections for the outward pressure of the tack device adjacent to the focal elevating elements, thereby minimizing the friction generated at the blood vessel wall.

The focal elevating elements can be formed and configured on the annular periphery of the tack device in a similar manner as described for the previous tack device embodiments and can include the raised contact sections in addition to anchors or sharp points. The contact sections can provide improved tacking characteristics in that they increase the contact forces at the contact sections by compressing the plaque at the contact regions and decrease the outward force at the sections neighboring the focal elevating element. This offers regional pressure relief in some sections and increase contact pressure at the bumps or sharp points collectively offering a reduction in trauma and cellular response of the blood vessel wall.

Because the tack device is held in place by its own pressure exerted on the blood vessel surface, it is susceptible to friction, including slight movement between the device and the vessel surface. Every time the organ moves (e.g., the leg during ambulation), the artery moves. It can be inferred that when the artery moves the working device sitting within the artery also moves but not necessarily every point of contact moves in synch with each other. Whenever there is even a small mismatch in movement between the artery and the device the artery and device rub against each other promoting cellular reaction and device failure. It has been deduced from experimental that this rubbing may irritate the endothelium causing an inflammatory response. In some embodiments, strategically placed focal elevating elements (FEEs) are implemented to reduce the overall regional friction load (thought to be a source of inflammation, cellular proliferation, and the healing response that leads to restenosis) of the area being held open.

As an example, a blood vessel such as the popliteal that is cyclically shortened and elongated is believed to have a cellular or tissue structures that elongate and compress in a direction parallel to the axis of the vessel. The natural behavior of this cellular or tissue structure involves a significant amount of local movement along this axial direction. If an implant to be placed in such a vessel is designed to contact the vessel wall in a direction transverse to this axial direction, the natural behavior of these tissues or cells will be greatly disrupted. For example, the tissue will be constrained and the natural movement will be greatly reduced. Also, rubbing can occur along the edges of the transversely contacting structure, resulting in friction and/or abrasion of the tissue and corresponding inflammation. FEEs, in contrast, reduce the disruption of the natural behavior of the tissue or cells. If incorporated into a tack device or other prosthesis, FEEs can focus the contact at zones that are spaced apart along a direction transverse to the predominant direction of motion (e.g., the axial direction in the case of the popliteal or similar vessel). Between these zones of focused contact corresponding to the FEEs, the interaction of the compressing and elongating tissue or cells with the structure of the implant is greatly reduced. In this in-between zone, the motion between the compressing and elongating tissue or cells can approach that of the tissue or cells before the implantation of the prosthesis. Raised sections produced by the FEEs limit the histological response of the tissue and also the fatigue of the device by limiting the contact between the device and the tissue.

Independent of the overall amount of contact and number of FEEs, the tack devices smooth the lumen wall, and allow more natural vessel movement. Where FEEs offer the greatest value is in there ability to reduce the amount of interaction between tissue or cells that move, elongate or compress, which can produce rubbing or friction to such tissue or cells. It is this highly localized movement or "micromovement" that increases the cellular response of the blood vessel surface to the foreign device.

The focal elevating elements are designed to reduce effective metal interface (EMI) by minimizing the overall material contact with the blood vessel surface. The focal elevating element (FEE) is preferably configured as a narrow, lifted feature with enough height to lift adjacent strut sections of the tack device off from contact with the arterial wall in order to reduce the surface area of foreign material in contact with the arterial wall. Reducing the contact burden is of particular value when the strut members are connecting circumferential rings or circumferentially oriented strut bands. Strut sections oriented against the natural grain of the cellular orientation that are in contact with the blood vessel walls can produce microfriction when they move or rub against the blood vessel walls. By reducing the foreign material contact area against the blood vessel wall, the tendency for production of microfriction contact is reduced.

Referring to FIG. 9, a schematic diagram illustrates some of the design assumptions for the use of focal elevating elements on a plaque tack device. In the figure, h refers to the height of the focal elevating element that is extended out of the blood vessel (note: the penetration depth of the focal elevating element that is anchored into the artery or plaque body is not included in this calculation), w refers to the width of the focal elevating element (at its base), and $l_F$ refers to the adjacent strut surface lifted off the arterial wall (mathematically simplified as a straight line). The struts adjacent to the focal elevating element may be fabricated with shape memory materials or designed as a compression wave providing compensation for lumen diameter variations. The strut forces adjacent to the focal elevating elements produce an outward bowing of the struts produced by the forces of the struts wanting to expand until they are in contact with the blood vessel wall. $l_A$ refers to the length of arterial wall that is kept out of contact with any adjacent strut structure by the focal elevating element.

One or more of the features labeled in FIG. 9 can be varied to provide advantageous FEE performance. For example, h can vary depending on the size of the delivery catheter for instance a 4 Fr provides a h of up to 150 um. In certain embodiments, a tack with FEEs configured for delivery in a 4 Fr catheter can have h of about 100 um or less. An example embodiment that can be deployed with a 4 Fr delivery system has one more FEEs with h of about 75 um. Larger tacks with FEEs, e.g., configured for delivery in a 6 Fr catheter can have an h of up to about 300 um and in some cases 225 um or less. An example embodiment that can be deployed with a 6 Fr delivery system has one more FEEs with h of about 200 um. Still larger tacks with FEEs, e.g., configured for delivery via a 8 Fr catheter, could have an h of up to 950 um while in certain embodiments FEEs of up to 500 um could be provided. An example embodiment that can be deployed with an 8 Fr delivery system has one more FEEs with h of about 400 um.

Any of the foregoing dimensions of h may be combined with a variety of dimensions of W of the FEE. The W dimension would typically be the width of the strut but could be as little of 50% the strut width and may be between about 50% and about 100% the width of the struts at the location of the FEE. $I_f$ and $I_a$ are a function of W, the radial force of the system, the topography of the lumen, and the delivery device, e.g., varied if a balloon is used to press the device into the artery. If we just look at W (non elastic system) then $I_a$ may be about equal to the length of the strut. As outward force (both from the elastic nature of the metal and the balloon assist) increases then $I_a$ can be reduced, approaching 0. However, in various embodiments, $I_a$ is at least about 20 um.

The focal elevating elements may be formed as cylindrical, rectangular, linear, spherical, conical, tear dropped, pyramidal, or inclined elements on the annular periphery of the tack device. They can be formed by bending or stamping a section of the tack structure, by an additive process (such as by welding or annealing on a peripheral surface), by a subtractive process (such as by grinding or etching away surrounding material so that the bump element is higher than the surrounding surface), or by modifying small sections of the peripheral surface to be higher than the surrounding surface before or after sheet or tube cutting. For example, one method of modification of small sections of a mesh tack structure is by knotting, twisting, bending or weaving small sections of the wire mesh to produce raised elements from the mesh surface which are the interface with the artery wall of the tack devices.

Properly oriented and symmetrically positioned focal elevating elements can provide foci for expansion force. As the device exerts outward forces and the artery exerts inward forces, the focal elevating elements can be positioned at strategically located positions reducing the outward pressure of strut sections neighboring the focal elevating elements.

Both anchors and focal elevating elements can offer strategic advantages that include: the reduction in pressure burden across the tack struts by reducing the contact area and translating the outward forces to the anchors and focal elevating elements, minimizing surface contact which offers a reduction in the tendency of frictional loading driven by micro movement between the arterial wall and the tack strut, and the stabilization of anchoring the tack where the anchor or focal elevating element penetrates the vessel wall a fraction of the features height.

Figure 10:
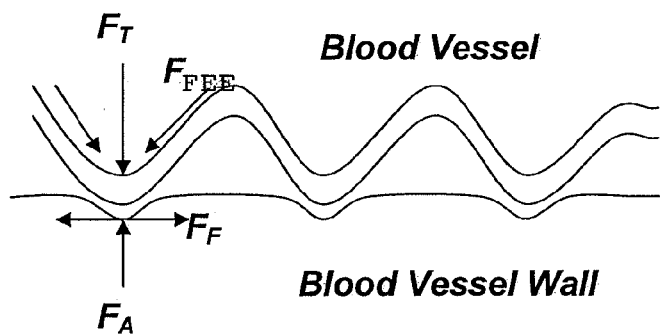
FIG. 10 illustrates use of a plaque tack with focal elevating elements for holding a plaque against a blood vessel wall.

Because the tack device is held in place by its own outward force pressure exerted on the plaque and blood vessel surface, it may be susceptible to friction, i.e., slight movement between the device and the vessel surface. FIG. 10 illustrates the forces at play between the tack's focal elevating elements and the arterial wall. $F_T$ is the circumferential force exerted by the tack device against the arterial walls force, $F_A$. $F_{FEE}$ is an additive circumferential force at the focal elevating element generated by the design and material choice and $F_F$ is the frictional force of the artery generated when the artery changes its orientation or shape due to body forces. Every time a body party moves, the blood vessels move slightly as well. The focal elevating elements can be strategically positioned to reduce local friction loading which may cause inflammation, cellular proliferation, or bodily response that leads to restenosis.

The number and locations of focal elevating elements can affect the overall Relative Metal Surface Area (RMS) which was explained previously. The focal elevating elements may be positioned along the lengths of the tack device surfaces such that a minimal amount of metal surface area is in contact with the artery wall. Focal elevating elements placed at bridges between circumferential strut rings or at the apices of strut sections of the tack device can offer a majority of arterial injury relief. When focal elevating elements are placed only at apices and bridges, the RMS of the strut members making up the concentric ring changes a little while the RMS of the bridges is reduced more significantly, due to the narrow length, offering relief of relative motion of the circumferentially oriented strut rings.

Figure 11:
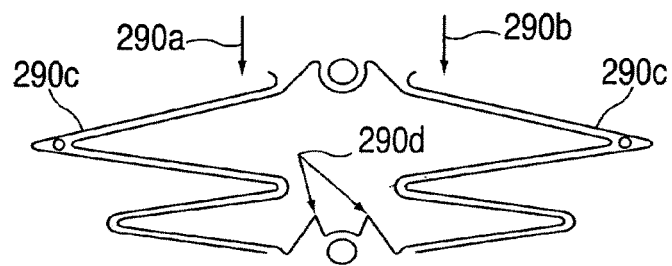
FIGS. 11 and 12 illustrate a variant use of focal elevating elements on a plaque tack.
Figure 12:
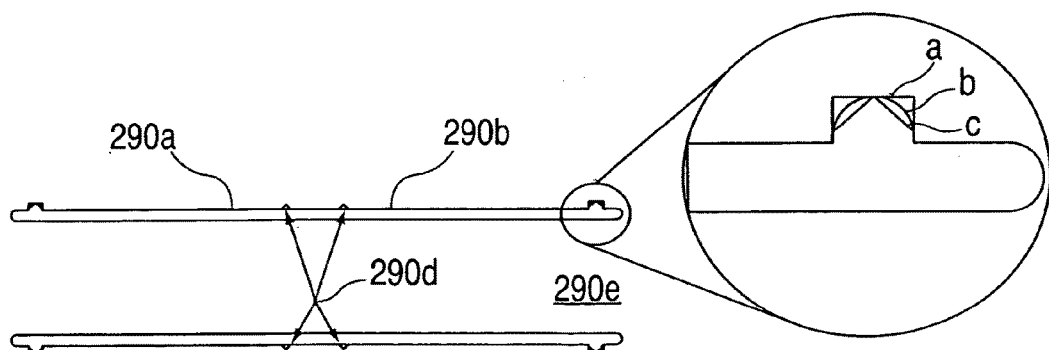

FIGS. 11 and 12 illustrate the use of focal elevating elements on a tack device of the type described above with respect to FIGS. 5A-C having two or more concentric ring sections joined by bridges in between. FIG. 11 shows a cell of two adjacent ring sections 290a and 290b with strut sections 290c and which are joined in the middle by bridges 290d. FIG. 12 shows the ring sections expanded under expansion force and opposing sets of focal elevating elements 290e deployed on opposite ends of the two adjacent ring sections 290a and 290b. An inset to the figure shows the round elevating element having a height raised from the strut surface.

Figure 13:
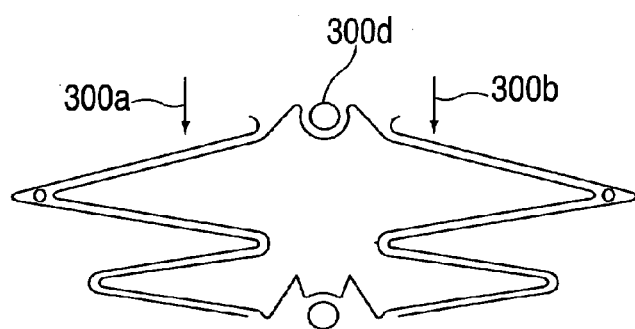
FIGS. 13 and 14 illustrate another variant of focal elevating elements on a plaque tack.
Figure 14:
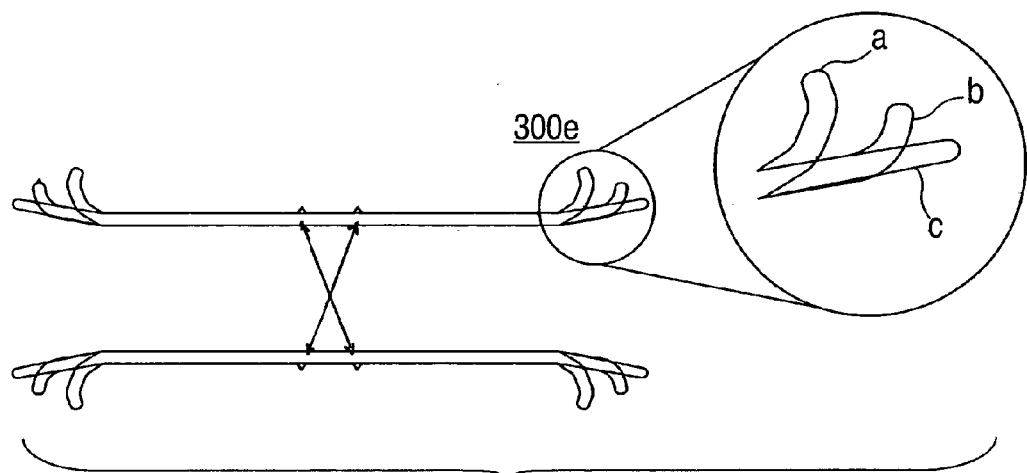

FIGS. 13 and 14 illustrate a cell of another variant of focal elevating elements formed on a tack device having two or more concentric ring sections 300a, 300b joined by bridges 300d in between. In this cell variant, the focal elevating elements 300e are formed by bending the sections of the strut (illustrated as the strut apex) out of the circumferential plane into varying degrees of tilt such as position "a", or position "b", up to a 90 degree vertical orientation shown in position "c" to form the elevating element.

Figure 15:
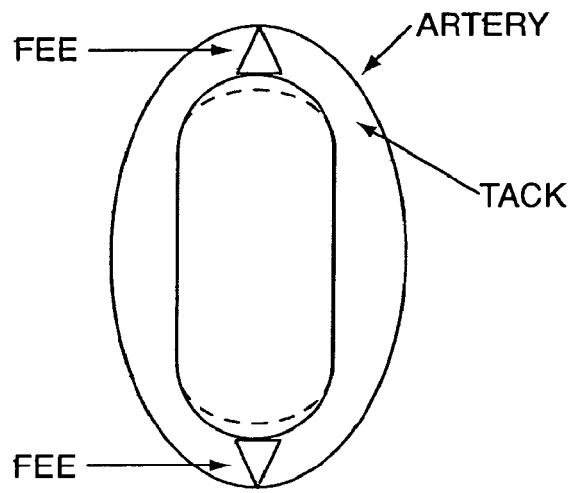
FIG. 15 illustrates the use of focal elevating elements to reshape artery walls into a desired cross-sectional shape.

Inherent in the use of shape memory alloys for the tack devices is the ability to conform to the shape of the blood vessel walls. Because the focal elevating elements can exert an expansion pressure on the blood vessel walls with a minimal risk of injury, they can be designed to reshape the blood vessel walls to a desired shape. FIG. 15 illustrates the focal elevating elements (FEE) positioned in diametrically opposite positions and formed with an extended height to reshape the artery walls into an ellipse cross-sectional shape which may better match the arterial cross section (such as an arterial branch) or expand the lumen to be more open in plaque-free areas.

Figure 16:
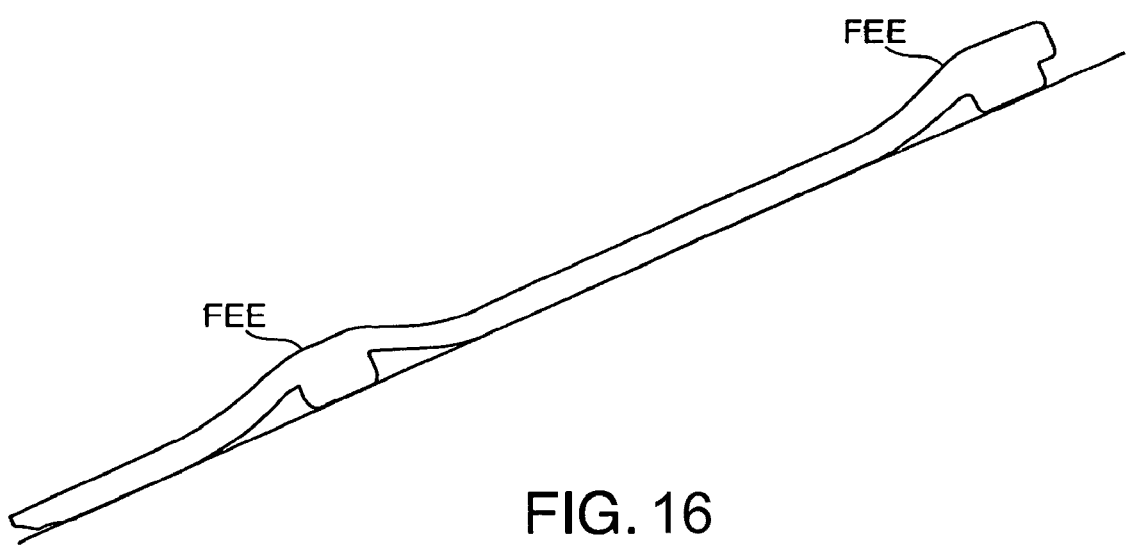
FIGS. 16-22 illustrate variations in forming and positioning focal elevating elements on the struts of a plaque tack.

FIG. 16 shows a side view of FEEs spaced along a strut length having a small area lifted off the arterial due to the height of the FEE lifting a short distance of the neighboring strut length. Outward forces generated by the design or material used allow for only a small section on either side of the FEE to be lifted off the blood vessel wall.

Figure 17:
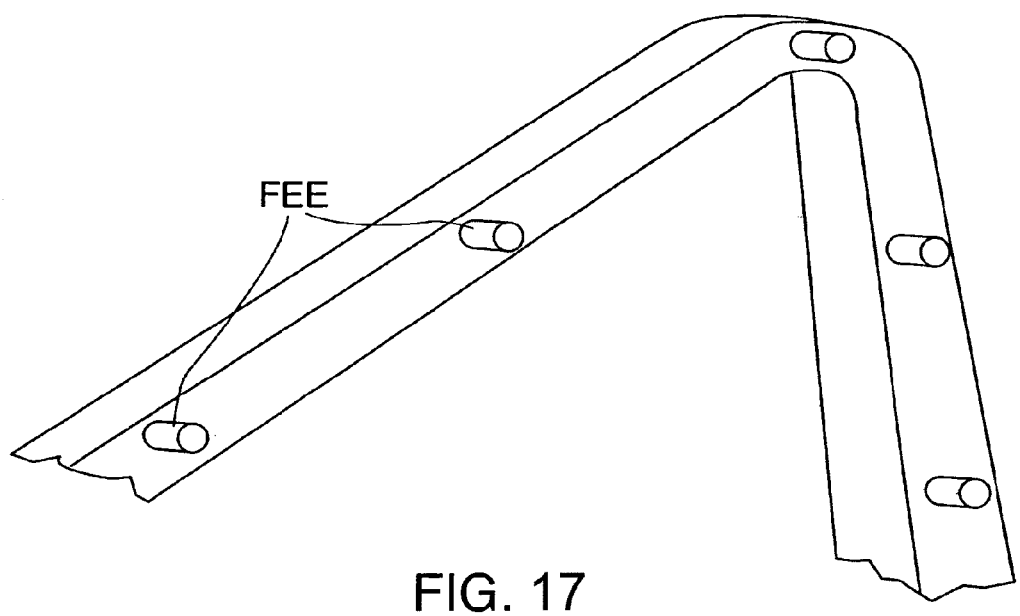
Figure 18:
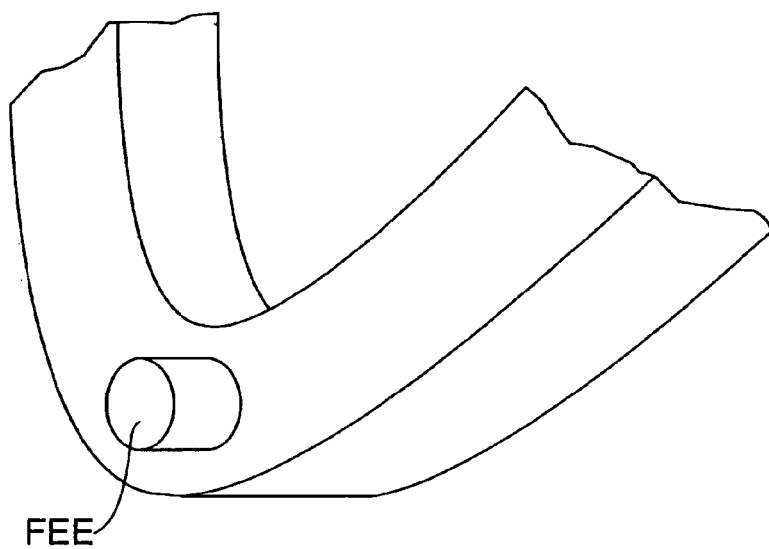
Figure 19:
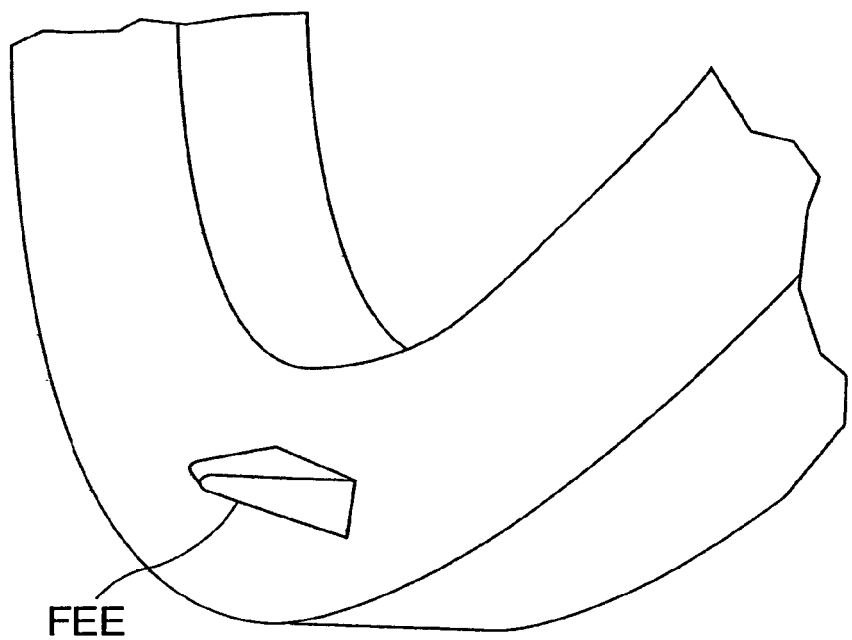
Figure 20:
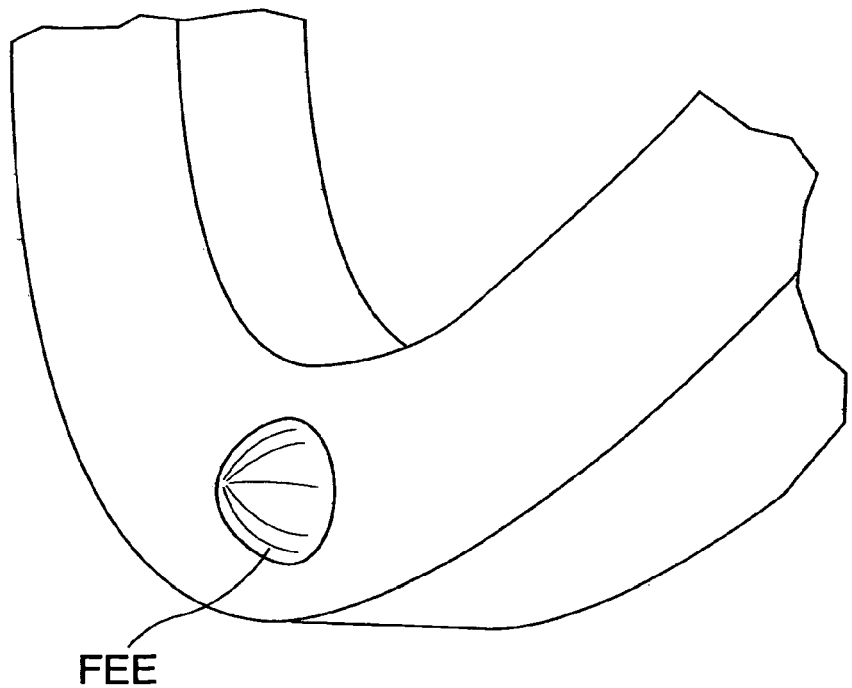
Figure 21:
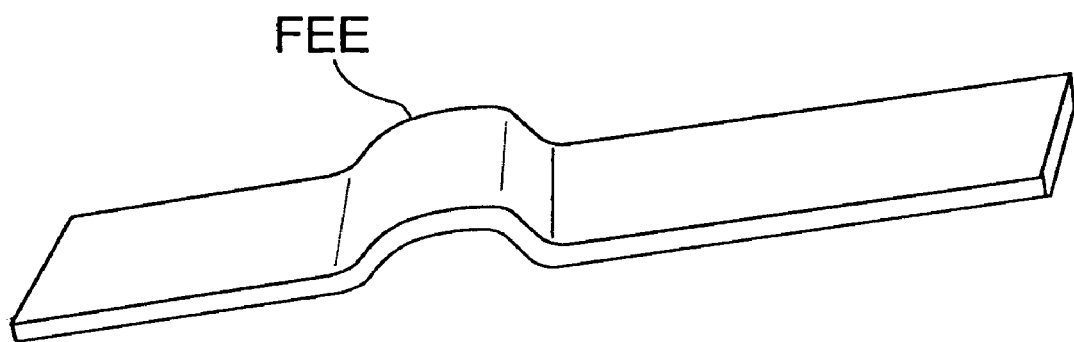
Figure 22:
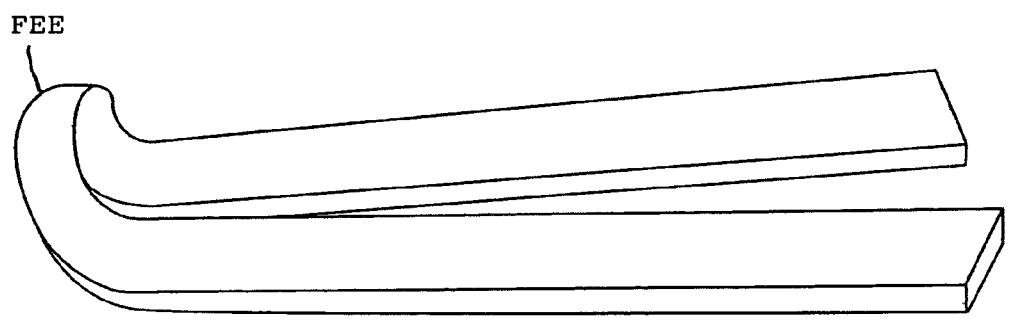

FIG. 17 illustrates a perspective view of a series of FEEs spaced along length of a strut section of a tack device. FIG. 18 illustrates a detailed view of a cylindrically shaped FEE placed at the apex of a strut section of the tack device. FIG. 19 illustrates a perspective view of a FEE formed as a pyramid shaped element at the apex of a strut section. FIG. 20 illustrates a perspective view of a FEE formed as a dome element at the apex of a strut section. FIG. 21 illustrates a perspective view of a FEE formed by bending the apex of a strut section upward. FIG. 22 illustrates a perspective view of a FEE formed by twisting a strut section (made from wire).

IV. Method and Devices for Delivering Plaque Tacks and Forming Intravascular Constructs In Situ A variety of delivery methodologies and devices that can be used to deploy plaque tacks, some of which are described below. For example, a plaque tack can be delivered into the blood vessel with an endovascular insertion. The delivery devices for the different embodiments of plaque tacks can be different or the same and can have features specifically designed to deliver the specific tack. The plaque tack and installation procedure may be designed in a number of ways that share a common methodology of utilizing an expansion force of the delivery mechanism (such as balloon expansion) and/or the expansion force of a compressible annular band to enable the tack to be moved into position in the blood vessel, then released, unfolded or unplied to an expanded state within the blood vessel.

Referring back to FIGS. 4-4D, a delivery device or catheter 11 with an outer sheath 13 is shown in a pre-delivery state. Multiple plaque tacks 10 can be compressed to be loaded onto the surface of the delivery device 11. The outer sheath 13 can then be advanced to cover the plaque tacks 10 in preparation for delivery. In some embodiments, the plaque tacks 10 are flash frozen in their compressed state to facilitate loading onto the delivery device. The tacks can extend in an array 10× over a given length of the delivery device.

It can be seen that the plaque tack 10 can be positioned in a patient's vasculature at a treatment site by the delivery device 11. The outer sheath 13 can be withdrawn or retracted to expose and release the plaque tack 10. The tack 10 can then be expanded in any suitable way, such as by being configured to self-expand or to be balloon expanded, as discussed herein.

Figure 23:
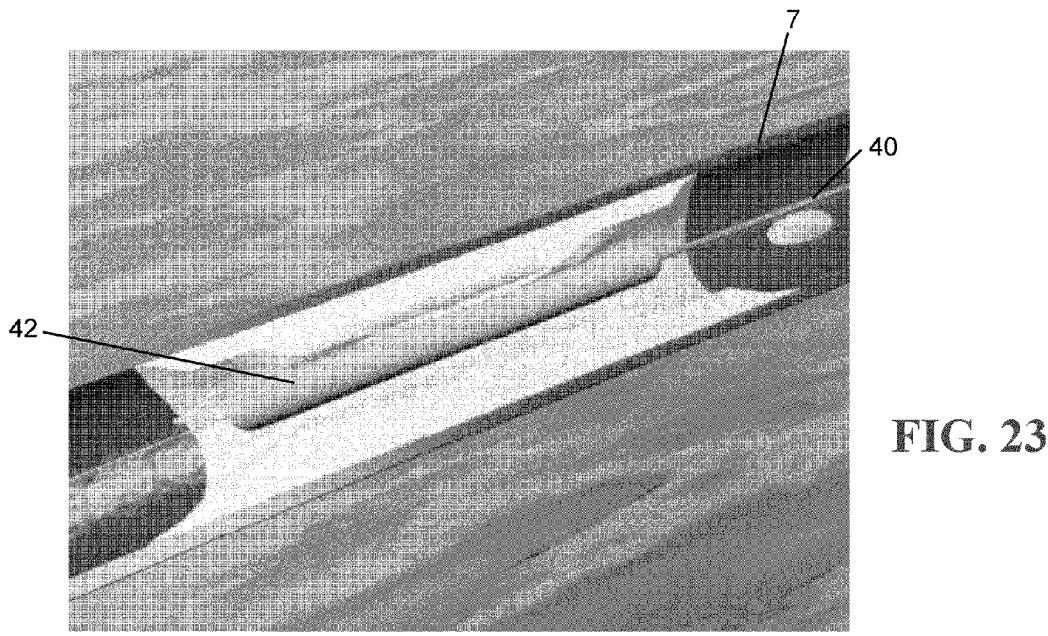
FIGS. 23-29 illustrate a method of delivery of a plaque tack into a blood vessel.
Figure 24:
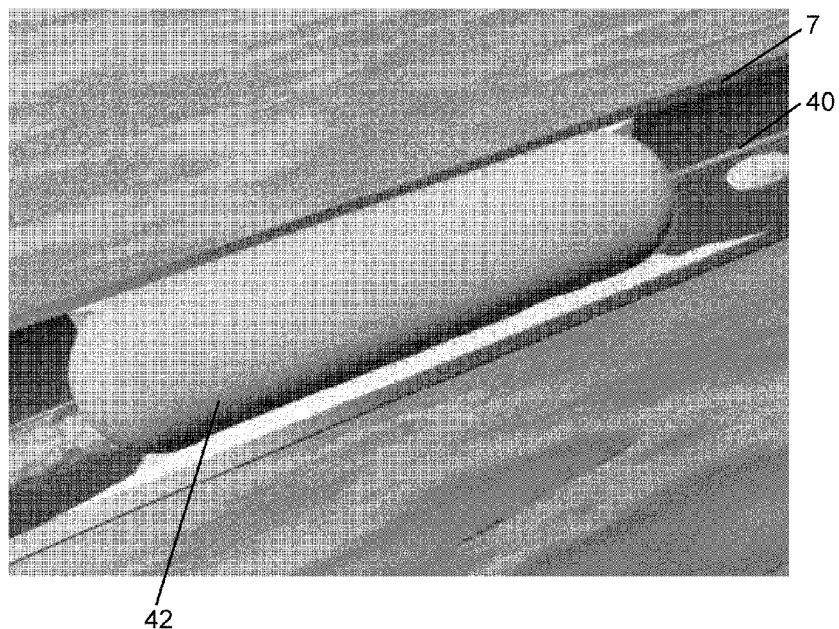

Turning now to FIGS. 23-31B, a method of delivery of one or more tack 10" will be described. As has been mentioned, an angioplasty procedure or other type of procedure can be performed in a blood vessel 7. The angioplasty may be performed on a diseased or obstructed portion of the blood vessel 7. As shown in FIG. 23, a guidewire 40 followed by an angioplasty balloon catheter carrying balloon 42 are advanced into a blood vessel 7 in a location containing an obstruction formed by plaque. The balloon 42 is inflated at the desired location to compress the plaque and widen the vessel 7 (FIG. 24). The balloon 42 can then be deflated and removed.

Figure 25:
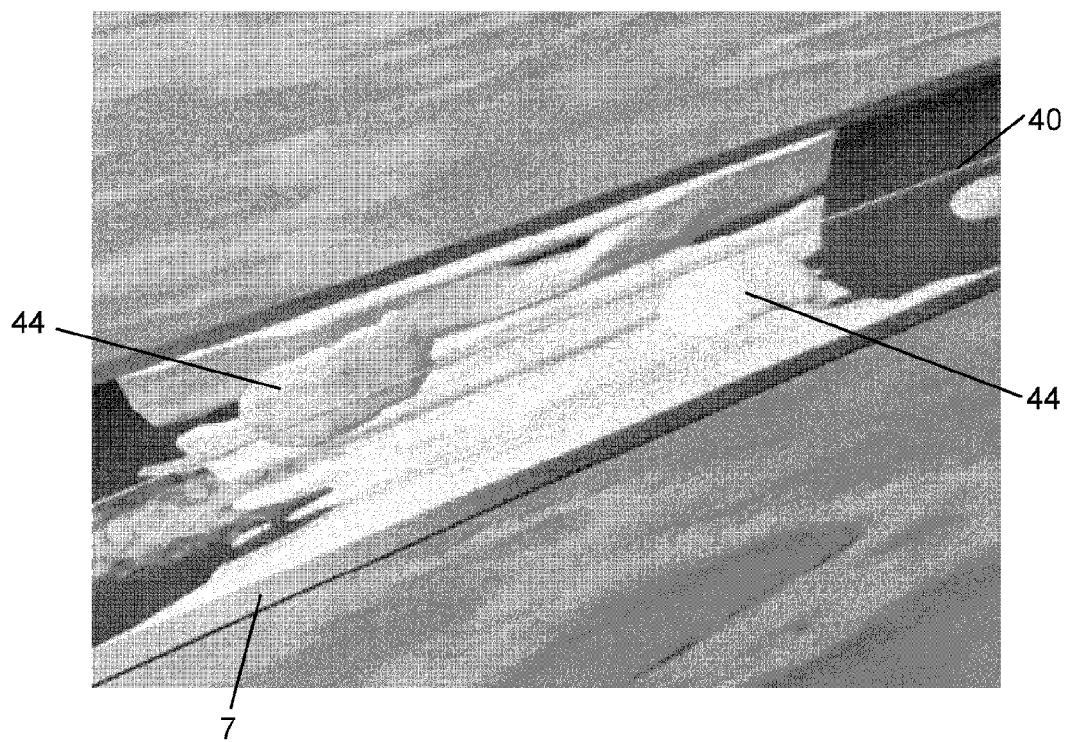

While widening the vessel 7, a dissection 44 of the plaque may be caused by the angioplasty (FIG. 25). A plaque tack or staple 10" can then be used to secure the plaque dissection 44 to the lumen wall 7.

Figure 26:
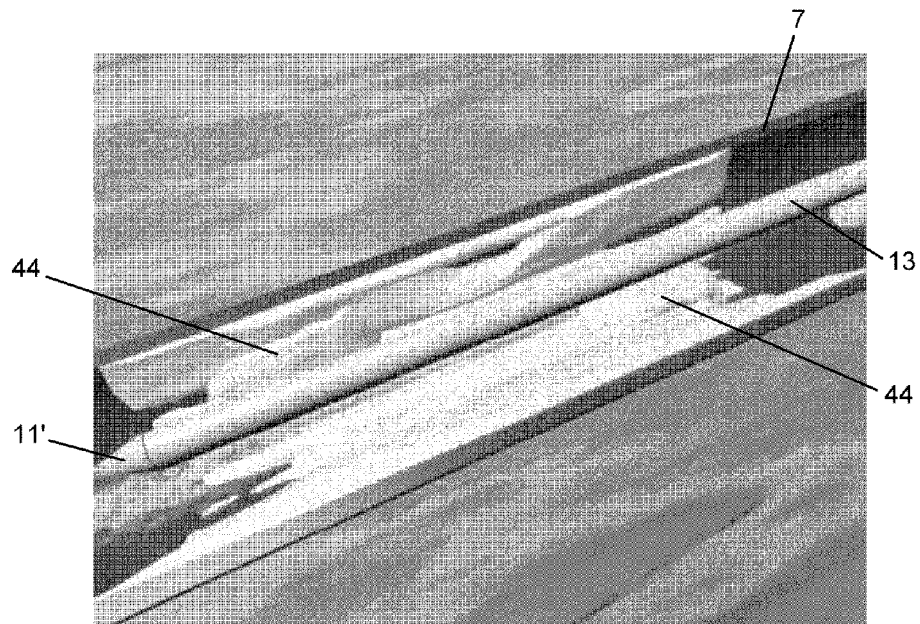
Figure 27:
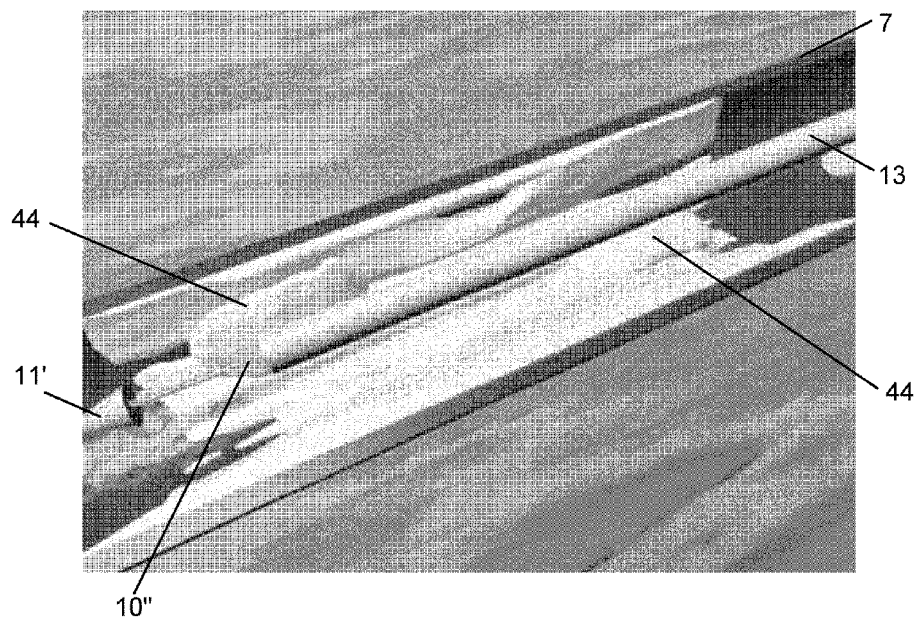

A delivery catheter 11' preloaded with one or more tacks 10" can be advanced along the guidewire 40 to the treatment site (FIG. 26). An outer sheath 13' can be withdrawn, exposing a portion of the plaque tack 10". As has been discussed, the outer sheath 13' can be withdrawn until a set point and then the position of the catheter within the vessel can be adjusted, if necessary, to ensure precise placement of the plaque tack 10" (FIG. 27). The set point can be for example, right before uncovering any of the tacks, uncovering a portion or all of a ring, uncovering a ring and an anchor, etc.

Figure 28:
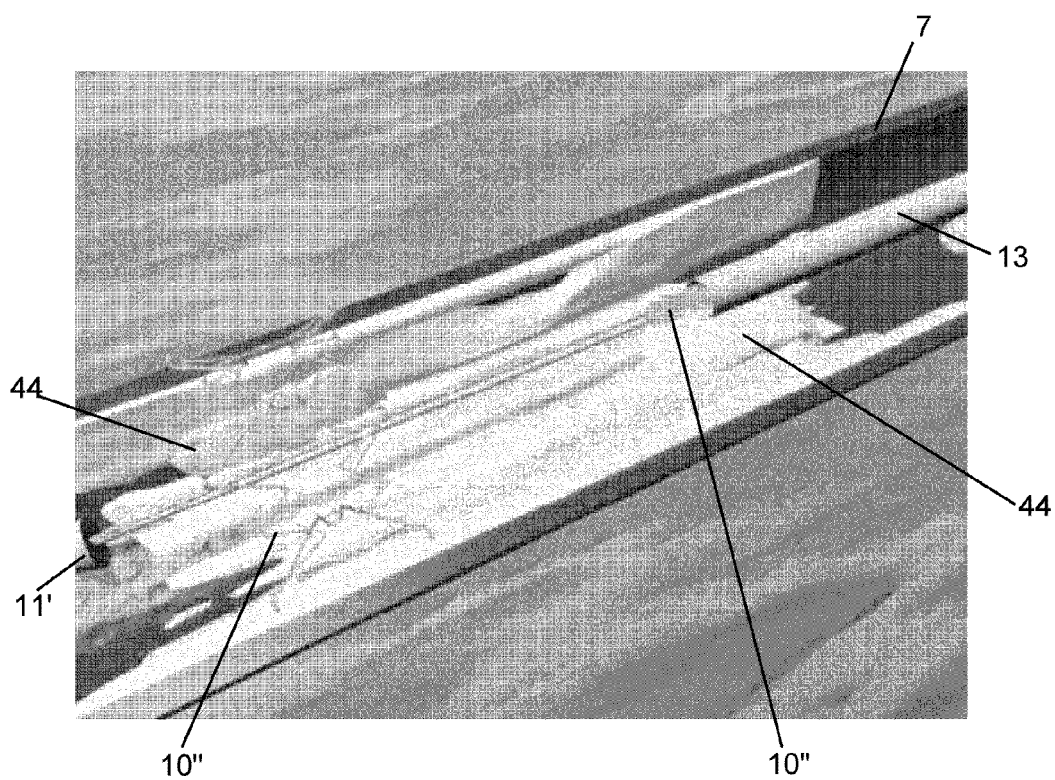

The tack 10" can then be released in the desired location in the lumen. As discussed previously, simultaneous placement can result upon release of some embodiments of the plaque tack 10". Additional plaque tacks 10" can then be placed as desired (FIG. 28). Upon placement of the second tack 10", an intravascular construct is formed in situ. 11. The in situ placement can be in any suitable vessel, such as in any peripheral artery. The construct need not be limited to just two tacks 10". In fact, a plurality of at least three intravascular tacks 10" (or any of the other tacks herein) can be provided in an intravascular construct formed in situ. In one embodiment each of the plurality of tacks has a length of no more than about 8 mm, e.g., about 6 mm in an uncompressed state. In one configuration, at least one of, e.g., each of, the tacks are spaced apart from an adjacent tack by at least about 4 mm. Although certain embodiments have a length of 8 mm or less, other embodiments can be longer, e.g., up to about 15 mm long. Also, neighboring tacks 10' be positioned as close as 2 mm apart, particularly in vessels that are less prone to bending or other movements. In one embodiment, each of the tacks has a relatively low radial force, e.g., having a radial expansion force of no more than about 4 N, and in some cases about 1 N or less. In some embodiments, tacks can be configured with as little as 0.25 N radial force. In the various delivery devices described herein, the spacing between implanted tacks can be controlled to maintain a set or a minimum distance between each tack. As can be seen, the delivery devices and/or tacks can include features that help maintain the desired distance between tacks. Maintaining proper inter-tack spacing can help ensure that the tacks are distributed over a desired length without contacting each other or bunching up in a certain region of the treated vessel. This can help to prevent kinking of the vessel in which they are disposed.

While a three tack construct formed in situ may be suitable for certain indications, an intravascular construct having at least 5 intravascular tacks may be advantageous for treating loose plaque, vessel flaps, dissections or other maladies that are significantly more elongated (non focal). For example, while most dissections are focal (e.g., axially short), a series of dissections may be considered and treated as a more elongated malady.

In some cases, even shorter axial length tack can be used to treat even more spaced apart locations. For example, a plurality of tacks each having a length of no more than about 7 mm can be placed in a vessel to treat a tackable malady. At least some of, e.g., each of, the tacks can be spaced apart from an adjacent tack by at least about 5 mm. In some cases, it may be preferred to provide gaps between adjacent tacks that can range from about 6 mm to about 10 mm.

Figure 29:
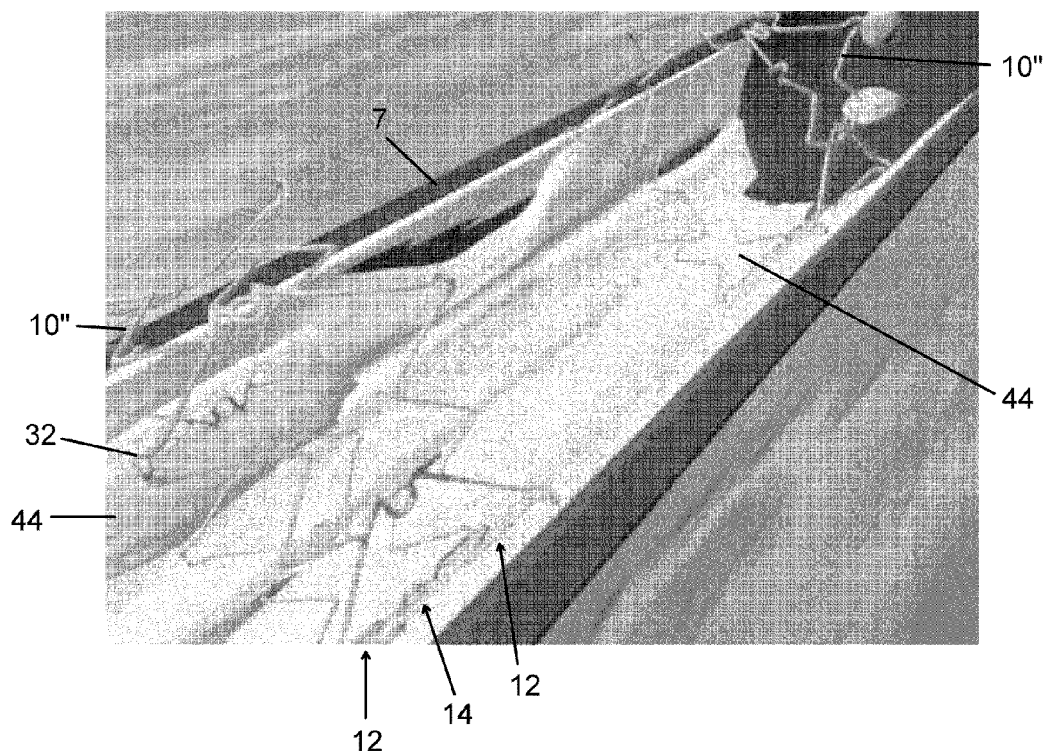

Optionally, once the plaque tacks 10" are in place, the angioplasty balloon can be returned to the treatment site and inflated to expand the plaque tacks 10" to the desired state of expansion. FIG. 29 shows the plaque tacks 10" in their final implanted state.

Figure 30A:
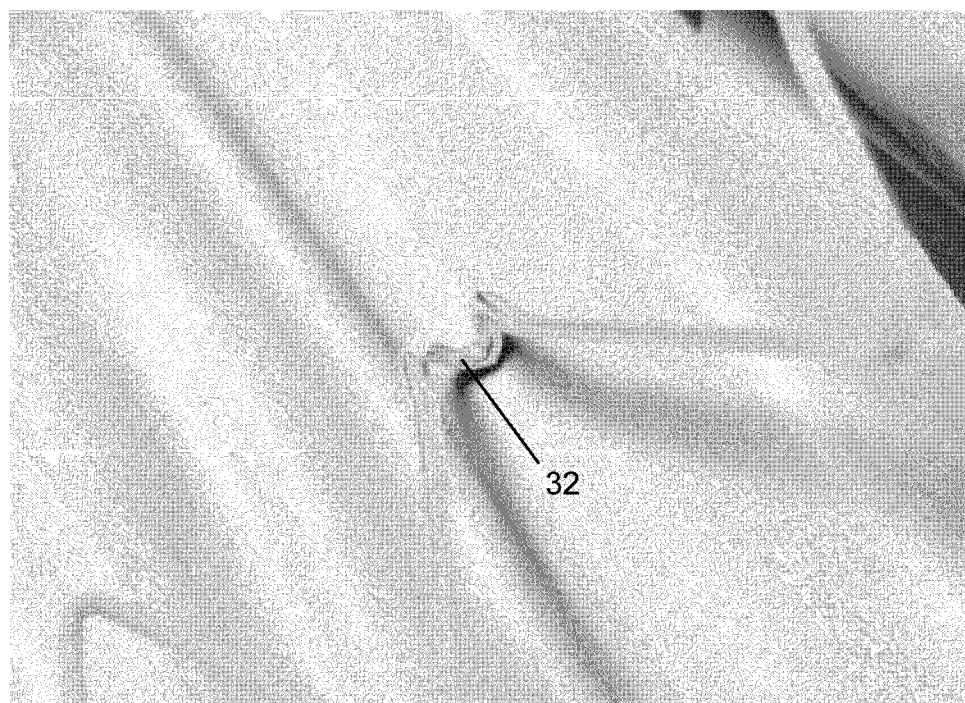
FIGS. 30A-B show a focal elevating element engaging plaque.
Figure 30B:
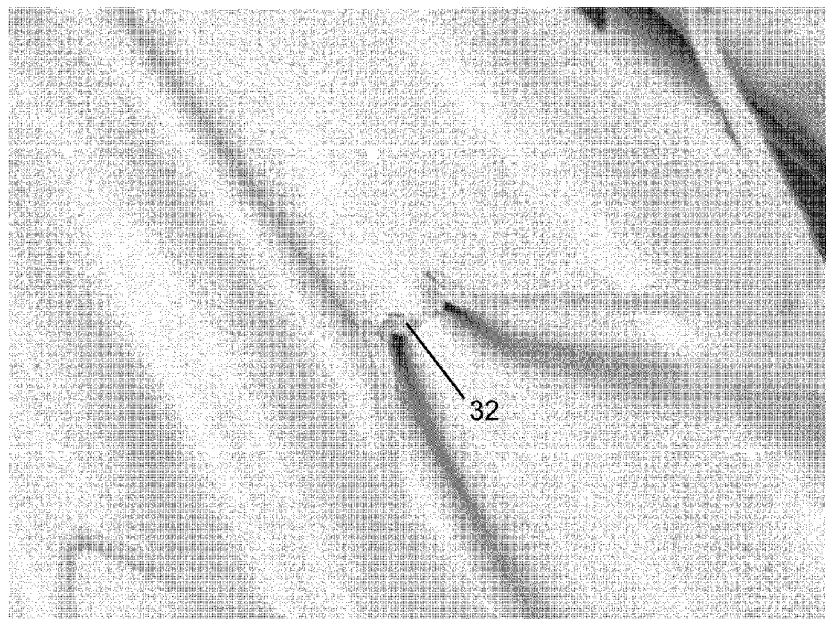
Figure 31A:
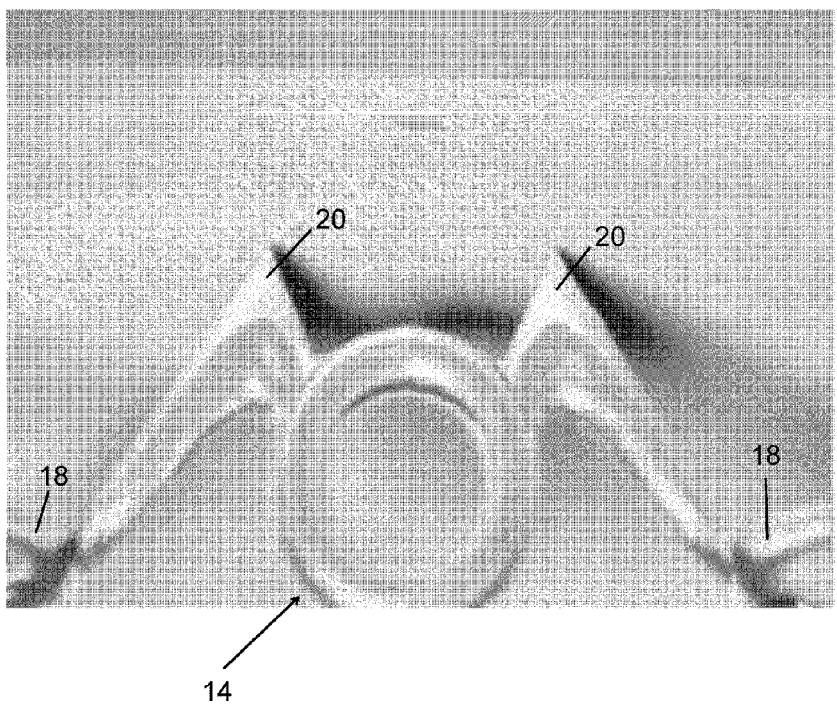
FIGS. 31A-B show anchors engaging plaque.
Figure 31B:
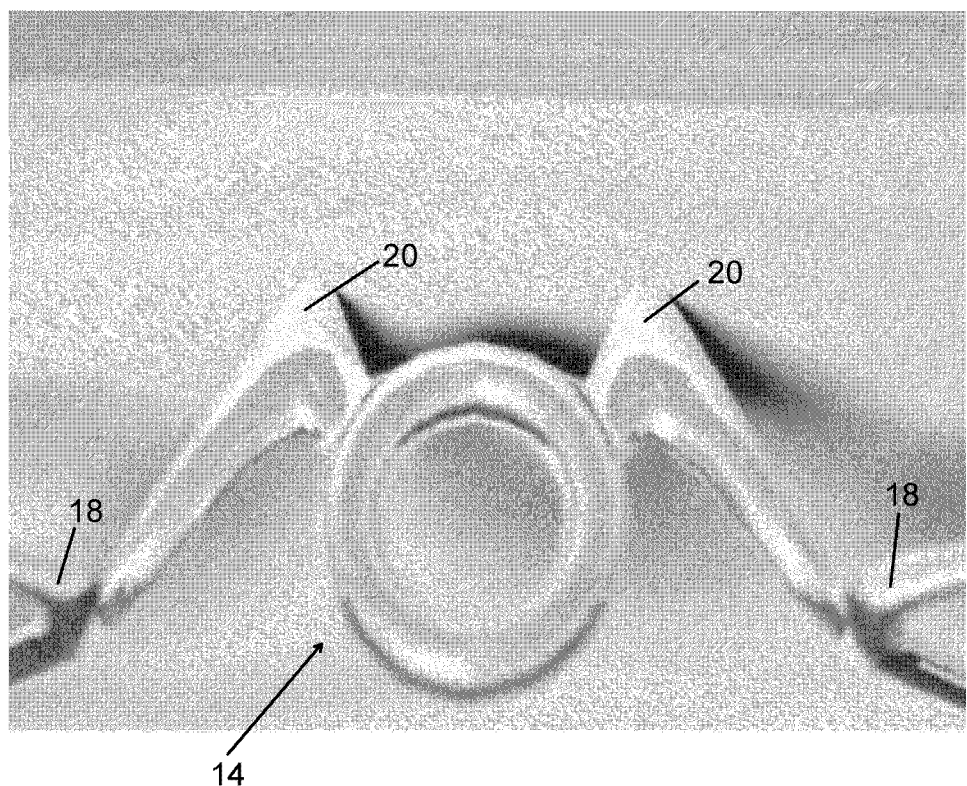

Referring to FIGS. 29, 30A, and 30B, it can be seen how the focal elevating elements 32 can both penetrate the plaque in the blood vessel wall and also minimize the contact area of the plaque tack 10" with the blood vessel wall. Similarly, FIGS. 29, 31A, and 31B illustrate the penetration of the anchors 20. It can also be seen that the position of the anchors 20 on the bridge 14 allow the anchors to protrude tangentially from the circular shape formed by the plaque tack 10". This beneficially allows the anchors 20 to engage the plaque or vessel wall while also minimizing the overall amount of contact by the plaque tack 10", similar to the focal elevating elements 32.

A. Further Systems and Methods for Delivering Plaque Tacks

FIGS. 32A-48D illustrate system for delivering a vascular prosthesis, e.g., any of the endovascular staples or plaque tacks discussed above. FIG. 32A shows a system 100 for controlled delivery of a self-expanding tack. Other systems discussed below can be used to further enhance deployed position of tacks and deployment of tacks that are expanded at least in part by an outward radial force.

The system 100 includes a catheter assembly 104 and a fixture 108 with which the catheter assembly 104 can be coupled. The fixture 108 can have a small configuration to be hand-held, but in some embodiments is fixed to a larger object or otherwise configured to be immobilized. The catheter assembly 104 can be received within the fixture 108 and held in place therein to limit or exclude unwanted relative motion between the fixture and at least one component of the catheter assembly 104. For example, the fixture 108 can include one or more caps 112 that can be configured to hold a portion of the catheter assembly 104. FIG. 32A shows that in one embodiment, the fixture 108 includes proximal and distal caps 112A, 112B which are discussed in greater detail below. The caps 112A, 112B can be removable to permit of the catheter assembly 104 into the fixture 108 by the clinician or can come pre-connected to the catheter assembly. The features of the fixture 108 can be combined with or augmented by those of the figures of FIGS. 46-48D, which describe additional details of deployment systems that can be disposed at the proximal end.

The catheter assembly 104 includes an elongate body 132, a sheath 136, and a plurality of intravascular tacks 140. Although one tack 140 is shown in FIGS. 32B and 33B, a plurality of additional tacks can be disposed within the catheter assembly 104, as discussed below in connection with FIG. 36A.

Figures 36, 36A:
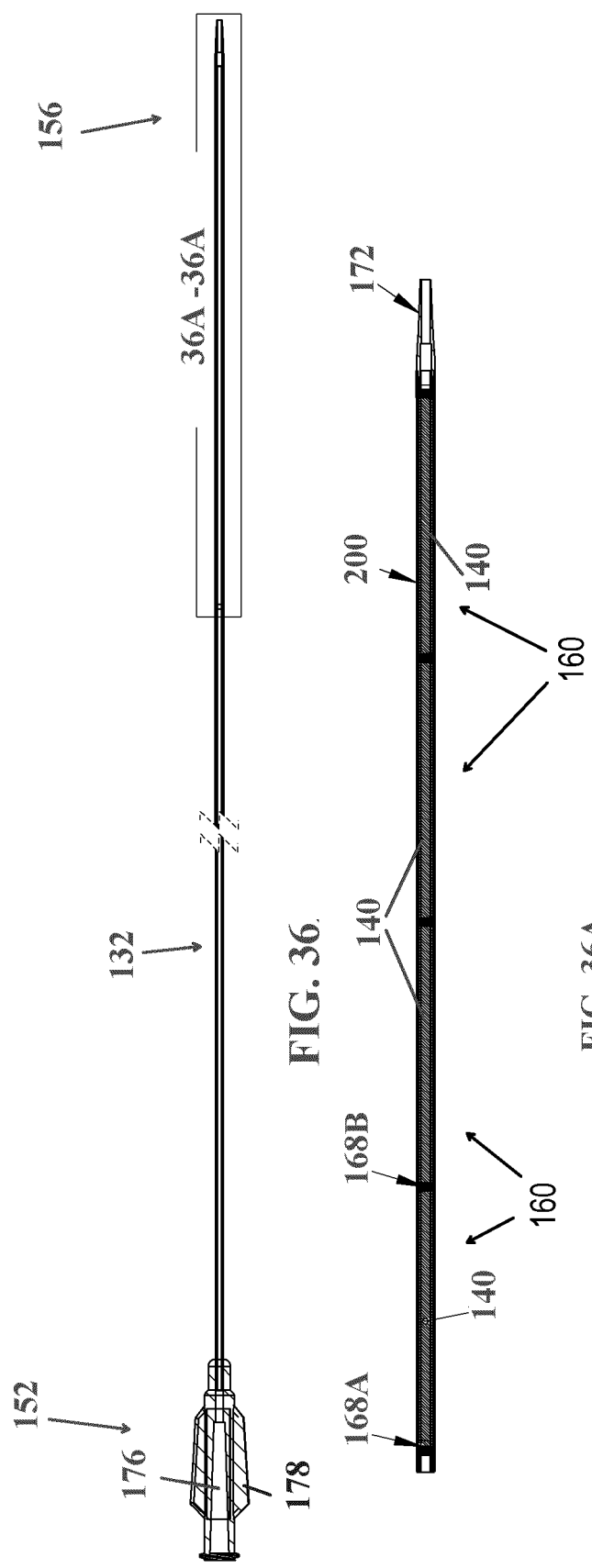
FIGS. 36-36A illustrate one embodiment of an elongate body that can have one or more plaque tacks disposed therearound within the sheath of FIG. 35.

FIGS. 36-36A show that the elongate body 132 has a proximal end 152, a distal end 156, and a plurality of delivery platforms 160 disposed adjacent the distal end. Each of the delivery platforms 160 comprises a recess 164 extending distally of an annular marker band 168 (FIG. 33B). The annular marker band 168 having a larger outer diameter as compared to the recess 164. In some embodiments, the recess 164 can be defined as the smaller diameter region next to, or between, one or two annular marker bands 168 and/or an additional feature on the elongate body 132. The platforms 160 are shown schematically in FIGS. 32A-33B and in more detail in FIG. 36A. In embodiments having a plurality of tacks 140, a plurality of corresponding delivery platforms 160 are provided. Any number of tacks and platforms can be provided, e.g., four tacks and platforms, two or more tacks and platforms, between 3 and 20 tacks and platforms, or other configurations. Each delivery platform 160 can include at least one marker band 168. For example, a proximal marker band 168A and a distal marker band 168B can be provided to make the ends of the platform 160 visible using standard visualization techniques. In the illustrated embodiment, the proximal maker band 168A of a first platform 160 is also the distal marker band of the platform located immediately distal.

The annular marker bands 168 can take any suitable form, for example including one more of tantalum, iridium, and platinum materials. In one specific arrangement (see FIG. 36A), the proximal most marker band 168A comprises tantalum, while distal marker bands 168B comprise one or more of platinum and iridium. The use of different materials for radiopacity can be based upon cost or a preference for higher visibility and/or a thinner structure. Platinum/iridium provides a greater radiopacity than tantalum, permitting the distal marker bands to be thinner or more visible than the tantalum band.

The ability to increase radiopacity to enable physician visibility under fluoroscopy can be provided for in various ways on the delivery device and the tack. One example is the inclusion of thicker zones of material (either wider circumferentially or radially thicker).

Also, the annular marker bands 168 have a radial height, which is the radial distance to the top of the band from the base of the recess 164. The radial distance can vary but preferably is just high enough to prevent the tack 140 from being caught between the elongate body 132 at the annular marker band 168 and the sheath 136. In certain embodiments, the radial distance is about equal to at least the thickness of the tacks 140 disposed in the catheter assembly 104.

In another embodiment, the delivery platforms 160 are disposed distal of a proximal marker band 168A where the marker bands are frusto-conical such that the proximal end of each marker band has a radius nearly equal to the radius of the elongate body 132 while the radius of the marker band at the distal end is a reduced radius. In some embodiments, the reduced radius can be the original radius as discussed above. In other words, the marker band slopes upward proximally toward a next-most-proximal tack. This creates a wall at the proximal end of the marker band 168A. A distal end of a tack after it is delivered sits against the wall and in this manner the marker band can assist in properly placing the tack. In addition, the sloped surface can be useful to facilitate the smooth withdrawal of the sheath from the elongate member before the tack is delivered. For example, the sloped surface can limit the ability of the tack, post deployment, to get hung up on a marker band as the sheath is being retracted. In some cases the tack may have a strut member that is not completely opposed to the wall, the sloped marker band can limit the ability of the marker band in catching this raised strut member as the sheath is withdrawn. In such an arrangement, the distal portion of the tack will be resting in the delivery platform just proximal to the slope edge of the proximal marker band in the delivery system 100 as opposed to being right up against the wall of the un-sloped marker band.

In a different embodiment, the marker bands can be frustoconical in the opposite direction in which the radius is greatest near a distal end and slopes downward proximally. In this embodiment, the marker band has a wall at the distal end. The sloped surface can be useful to facilitate the smooth withdrawal of the elongate member after the tack has been delivered. For example, the sloped surface can limit the ability of the tack, post deployment, to get hung up on a marker band as the elongate member is retracted from the vessel. In a variation, the delivery platform can be frustoconical in one or more directions.

The marker bands can be frustoconical in one or more directions. The frustoconical segment of the marker band can be formed by glue that can secure the marker band onto the elongate member. The glue can form a fillet between the marker band and the elongate member. The fillet can have a concave, substantially planar or a convex outer surface. In some embodiments the marker band can have fillets on either side with different outer surfaces. For example, the marker band can have a concave fillet on the distal end and a fillet on the proximal end that has a substantially planar outer surface or an outer surface that is less concave than the distal fillet.

In some variations, the tacks 140 are purely self-expanding. In other variations, at least one of the delivery platforms 160 comprises an expandable member to expand a tack disposed thereon. The expandable member can comprise a standard construction as for balloon angioplasty or a specialized design, as in FIG. 45. The tacks 140 can also be deployed by specialty balloons coated with drugs to minimize restenosis, inflammation, or other side effects of a treatment with a plaque tack.

The elongate body 132 includes a distal tip 172 that is tapered to provide for easy insertion and a lumen 176 extending proximally therefrom to the proximal end 152. As discussed above in connection with FIGS. 4-4D, and FIGS. 23-31, the lumen 176 can be used to guide the distal end of the catheter assembly 104 to a treatment zone. The proximal end 152 can take any suitable form, but preferably is configured to lockingly engage with the fixture 108. For example, FIG. 36 shows that the proximal end 152 can include a luer hub 178 with flanges that can be received within a similarly shaped recess formed in the fixture 108. For example, a recess at least partly matching the shape of the hub 178 can be formed between a base 110 of the fixture 104 and the cap 112A. When the elongate body is received in the fixture 104, the hub 178 is positioned between the cap 112A and the base 110 in this recess and is locked in place by a secure connection of the cap 112 to the base 110, preventing unwanted movement of the elongate body 132 relative to the sheath 136 and reducing or preventing movement relative to a fixed reference frame, such as the reference frame of the fixture 104.

The sheath 136 has a proximal end 192, a distal end 198, and an elongate body 200 extending therebetween. The sheath 136 is moveable relative to the elongate body 132 from a first position to a second position. The sheath can be formed of a hypotube, such as a metal or plastic hypotube. Flexibility and stiffness of the sheath can be controlled by many features such as the slope and frequency of a spiral cut along the length of the hypotube.

FIGS. 32A-32B illustrate a first position in which the distal end 198 of the sheath 136 is disposed distally of a distal-most distal delivery platform 160. In FIG. 32B, the distal-most platform is occupied by a tack 140. Another platform disposed immediately proximal of the occupied platform is shown without a tack for clarity but can be occupied by another tack. Further platforms and tack can be disposed further proximally. FIGS. 33A-33B illustrate a second position, in which the distal end 198 of the sheath 136 is disposed proximally of a portion of at least one delivery platform 160.

The sheath 136 also can include a bifurcation luer 204 with a main arm to receive the elongate body 132 and a side arm 206 disposed at the proximal end of the elongate body 200. The side arm 206 includes a flushing port that is used to flush out air and increase lubricity in the space between the sheath and the elongate body 132. A tuoy borst adapter 208 (or other sealing arrangement) can be provided proximal of the bifurcation luer 204 to receive the distal end of the elongate body 132 prior to application to a patient (e.g., in manufacturing). In some embodiments, a strain relieve sleeve 212 is provided between the bifurcation luer 204 and the elongate body 200 to make the connection more robust. The strain relief sleeve 212 can take any form, such as being made of polyolefin or other similar material.

In one technique of use, the distal end of the catheter assembly 104 is inserted into the patient and the proximal end is placed in the fixture 108. The sheath 136 is in a distal position, e.g. with the bifurcation luer 204 forward in the fixture 108. During the procedure, the sheath 136 is moved progressively towards a proximal position, e.g. with a proximal portion of the tuoy borst adapter 208 in contact with a distal portion of the cap 112A of the fixture 108. As the sheath 136 is moved proximally the tacks are deployed either one at a time, where the clinicians repositions the elongated body 132 after each deployment or set of deployments or all at once without repositioning the elongate body 132.

The fixture 108 advantageously assists in placement of multiple tacks 140 to a treatment zone at spaced apart locations, as illustrated in FIG. 29. For example, the fixture 108 reduces unintended relative motion between the sheath 136 and the elongate body 132. If the fixture 108 is immobilized, the fixture assists in limiting motion of the elongate body 132 due to internal friction binding on the sheath 136 as the bifurcation luer 204 is moved proximally. As a result, a more controlled deployment can result than if the clinician were to hold both the proximal ends of the elongate body 132 and sheath 136 directly. This helps to ensure a minimum gap is provided in the treatment zone between the distal end of a proximal tack and a proximal end of a distal tack. The gap can be seen in FIG. 29, which illustrated deployment of two tacks 10". The gap advantageously minimizes the chance that two tacks will cause kinking in the vessel or other maladies due to being too close. The gap or spacing between tacks can be controlled to be between about 4 mm and about 20 mm in certain embodiments. In other embodiments, the spacing between tacks can be controlled to be between about 5 mm and about 14 mm. In other embodiments, the spacing between tacks can be controlled to be between about 6 mm and about 12 mm.

Also, this arrangement enables placement of two or more tacks without requiring that the delivery platforms 160 be moved between deployment of tacks 140. Rather, the delivery platforms 160 can be positioned and held in place prior to deployment of a first tack 140. After the deployment of the first tack 140, the delivery platforms 160 can be maintained in a position and the sheath 136 can be retracted to expose and deploy a second tack 140, a third tack 140 or more.

The system 100 provides the further advantage of precise placement of multiple vascular prostheses once the catheter assembly 104 is placed inside the patient. In particular, after placement, the catheter assembly 104 need not be withdrawn and exchanged for other catheters or catheter systems to perform further treatments. In this regard, the system 100 can be used for endovascular staples or tacks as well as stents and other vascular devices that are spaced apart in different treatment zones in the patient's body.

1. Minimizing Movement with a Distal Anchor

With certain endovascular prostheses, precise placement at a treatment site or zone is important, e.g., when the prosthesis is relatively short, such as having a ratio of axial length to transverse width (e.g., diameter) of 1 or less or if placement occurs in a tortuous path (e.g., at a arterial bend). Stabilizing at a proximal end, as with the fixture 108, can provide reliable placement, but stabilizing closer to the prosthesis can provide even better accuracy in terms of axial location as well as minimizing tilting of the device within the vessel. In this context, tilting includes any non-perpendicularity of a transverse aspect of the device to the lumen in which it is deployed. For tack 10', a transverse aspect can be defined by a plane intersecting the high outward apices 24. Tilting in relatively short prostheses can reduce the stability thereof. Tilting of the tack 10' can rotate the anchors 20 out of optimal orientation to engage plaque, reducing their effectiveness, for example.

a. Minimizing Movement with Actively Expandable Distal Anchor

Figure 37B:
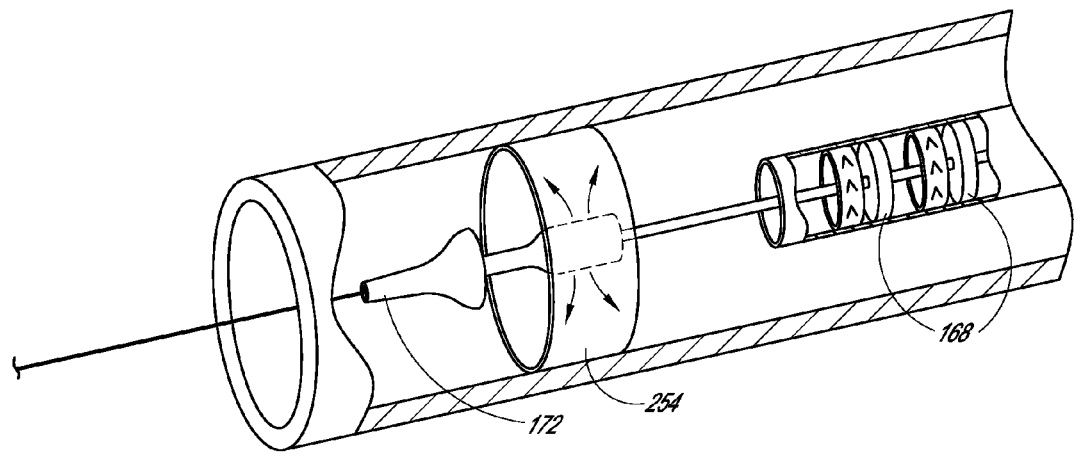
FIGS. 37A-37B illustrate a variation of the delivery system in which an actively actuated member is provided to anchor the system near the treatment zone.
Figure 37A:
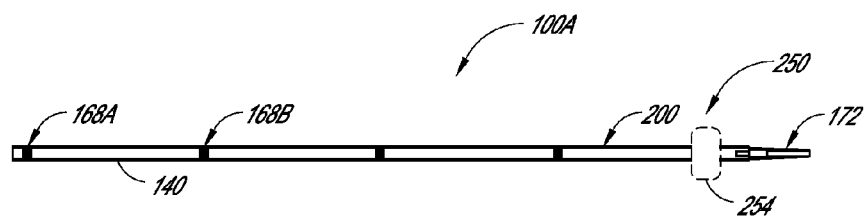

FIGS. 37A and 37B illustrate a delivery system 100A that is a variation of the delivery device 100, but having a distal portion thereof configured to stabilize the system in the vasculature to enable even more precise placement of two or more tacks. In particular, the system 100A includes a stabilization device 250 disposed on an outer surface of the system, e.g., on an outer surface of and elongate body 132A. The stabilization device 250 can be adapted to directly engage a body lumen. In some embodiments, the stabilization device 250 is adapted to engage the lumen at a plurality of locations disposed about the lumen, e.g., at discrete points or at a continuous circumferential line or area of contact. Such engagement can advantageously minimize movement of the elongate body 132A relative to the body lumen when relative movement is provided between the sheath 136 and the elongate body 132A. For example, the stabilization device 250 can maximize radial centering during movement of the sheath 136, which can advantageously control a gap between adjacent tacks deployed by the system 100A.

The stabilization device 250 can maximize radial centering during movement of the sheath 136 to locate the center of the elongate body 132 at the distal-most delivery platform 160 within about 50% of the radius of the vessel in which the platform resides, which can advantageously control tilting of each tack deployed by the system 100A. In certain embodiment, the stabilization device 250 maintains the center of the elongate body 132 at the distal-most delivery platform 160 within about 40% of the radius of the vessel in which the delivery platform resides. In other embodiment, the stabilization device 250 maintains the center of the elongate body 132 at the distal-most delivery platform 160 within about 30%, about 20%, or about 15% of the radius of the vessel in which the delivery platform resides. Radial shifting can include transverse displacement inside a body lumen or angulation within a vascular segment. For example, due to the tortuosity or curvature of a blood vessel, distal portion of the system 100A can have varying distance from the vessel wall along its distal length. When viewed from the side, the elongate body 200 of the sheath 136 forms an angle to the central longitudinal axis of the vessel. As a result, one side of the elongate body 132A is closer to the vessel wall than the other and the distance varies over the length of the tack 140. This can cause one of the proximal or distal ends of the tack 140 to engage the vessel first, causing the tack to tip in the vessel. The stabilization device 250 can bring a distal segment of the system 100A closer to coaxial with the longitudinal axis of the vessel. For example, the stabilization device can be configured to maintain the longitudinal axis of the elongate body 132A within 20 degrees of the longitudinal axis of the vessel for at least 4 delivery platforms. In some embodiments, the stabilization device 250 can be configured to maintain the longitudinal axis of the elongate body 132A within 10 degrees of the longitudinal axis of the vessel for at least 10 mm. In some embodiments, the stabilization device 250 can be configured to maintain a transverse aspect of the tack 140 to within 10 degrees of perpendicular to the longitudinal axis of the blood vessel.

The stabilization device 250 can be configured to reduce or minimize axial shifting. For example the device 250 can reduce or minimize movements of one or more of the delivery platforms 160 along the lumen of a vessel in which the platform is disposed to enhance control of deployment. The stabilization device 250 can maintain the axial position of a distal facing surface of an annular marker band 168 to within about 15%, 20%, 30%, 40%, or 50% of a delivery platform length. The delivery platform length can be measured parallel to the longitudinal axis of the elongate body 132 between a distal facing surface of a proximal marker band 168A disposed at the proximal end of the delivery platform and a proximal facing surface of a distal marker band 168B disposed at the distal end of the same delivery platform. In some applications, axial shifting is reduced or minimized at least for second and subsequent tacks deployed, e.g., to help to maintain inter-tack spacing as discussed elsewhere herein. The stabilization device 250 can also be configured to reduce or minimize any offset in the position of a first or subsequent tack that is deployed when compared to a planned implantation location. The planned implantation location is the absolute position in a vessel at which a clinician desires to place the tack, which can be based upon visualization techniques such as fluoroscopy or other surgical planning method.

The stabilization device 250 can include an inflatable balloon 254 that can take any suitable shape. For example, the balloon 254 can be cylindrical as shown in FIGS. 37A-37 or conical. One advantage of a conical shaped balloon is that the dilating function provided by the tapered tip 172 can be performed by the leading edge of the conical balloon and so these structures can be combined in some embodiments. Or, if the anatomy is not cylindrical an appropriately shaped balloon, such as a conical balloon, could be matched to the shape of the anatomy to provide better apposition.

In the illustrated embodiment, a cylindrical balloon 254 is disposed proximally of the distal tip 172. The stabilization device 250 can be disposed between the distal end of the elongate body 132A and at least one of the delivery platforms 160. The balloon 254 is configured to minimize at least one of axial or radial shifting of at least one of the delivery platforms 160 along or away from a longitudinal axis of a blood vessel in which tacks or other vascular prostheses are to be deployed.

The balloon 254 can be inflated by any suitable means, such as by flowing an inflation medium through a lumen in the elongate body 132 from the proximal end thereof to an inflation port in the balloon 254. The elongate body 132 for the system 100A can be formed as a dual lumen extrusion, where one lumen is used for the guide wire and the other lumen is used to inflate the balloon 254. The inflation lumen can be connectable at the proximal end of the elongate body 132 to a syringe or other source of positive pressure to deliver the inflation medium. The balloon 254 has a low profile configuration prior to inflation that enables it to reside on the elongate body 132 without impeding delivery of the distal portion of the system 100A. For example, the balloon 254 can be disposed within the sheath 136 (e.g., between an inner surface of the sheath 254 and the lumen 176) prior to being inflated. In another embodiment, the balloon is disposed longitudinally between the sheath 136 and the tip 172. In such embodiment, it may be advantageous for the balloon to act as the tip where the distal end is tapered to allow for navigation of the vessel while the proximal end of the balloon is the same width (e.g., radius) as the sheath 136 to provide a smooth transition between the two to prevent any step at the interface between the balloon and the distal end of the sheath 136.

The use of the balloon 254 provides the clinician the ability to initially place and inflate the balloon distally of the lesion. Then after the balloon is anchored to the wall of the vessel, the sheath 136 is withdrawn exposing one or more tacks 140 enabling the tacks to be released at pre-defined separated locations. The separate locations are pre-defined because they correspond to the pre-established separations of the tacks on the delivery system 100A.

One advantage of the balloon 254 is the additional functionality of using the balloon for post dilation of the tacks after placement. In this case after tacks are placed in the vessel the balloon 254 can be repositioned within a deployed tack 140 and reinflated engaging the tack with outward pressure from the expanding balloon to enhance placement of the tack at the vessel wall.

Figure 38:
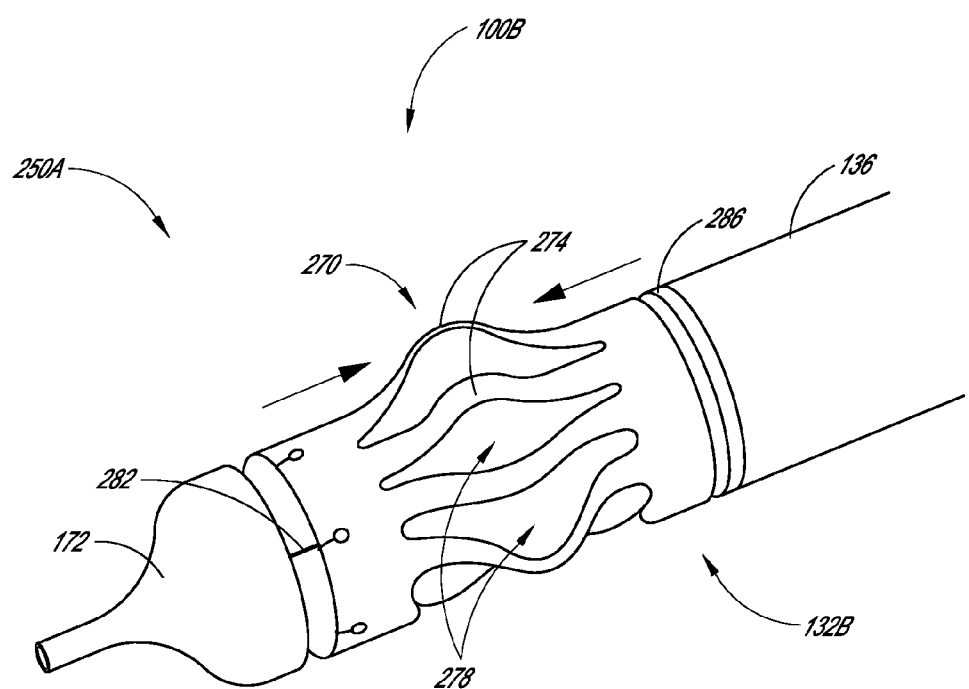
FIG. 38 illustrates a variation of the delivery system in which a linkage is provided to actively actuate a member positioned near the treatment zone.

FIG. 38 illustrates one of several embodiments where a proximal control is provided to actuate a linkage to move one or more distal components of a delivery system to cause radial expansion for anchoring engagement with a vessel wall. In particular, the system 100B includes a stabilization device 250A that is configured to be actively enlarged from a low profile configuration to an expanded configuration. The low profile configuration is one that is suitable for advancement through the vasculature. The low profile configuration also enables the sheath 136 to be advanced over the stabilization device 250A without radially expanding the sheath 136.

The stabilization device 250A includes a stabilization element 270 disposed adjacent the distal end of an elongate body 132A. The elongate body 132B has a plurality of delivery platforms 160 proximal of the stabilization element 270 and is similar to the elongate body 132 except as set forth below. In the illustrated embodiment, the stabilization element 270 includes a plurality of elongate axially oriented strips 274 that are separated by slots 278. The strips are sufficiently flexible such that they are able to expand radially when compressive forces applied to proximal and distal ends thereof. The radial expansion of the strips 274 causes outer surfaces thereof to engage the wall of the lumen at circumferentially spaced apart locations.

The stabilization device 250A also includes a linkage 282 and an actuating mechanism configured to apply a compressive force to the stabilization element 270 (indicted by the arrows in FIG. 38). The linkage 282 can be a wire having a distal end coupled with the tip 172 and a proximal end coupled with the actuating mechanism The actuating mechanism can be integrated into the deployment system 500 of FIG. 46, discussed in greater detail below, or any of the other deployment systems or devices described herein.

The linkage 282 can be eliminated by providing a balloon or other actively expandable member within the stabilization element 270 such that the user can actuate the balloon to expand the elongate axially oriented strips 274 into engagement with a vessel wall. The strips 274 advantageously define gaps therebetween through which at least some blood can flow downstream of the stabilizing element 270. This can minimize ischemia during a procedure compared to other anchor devices that are more occlusive.

An imaging device 286, such as a radiopaque band, can be positioned proximal of the stabilization element 270, e.g., between the stabilization element 270 and the distal most delivery platform 160, to indicate to the clinician that the stabilization element 270 is distal the lesion or treatment zone.

b. Minimizing Movement with Passively Expandable Distal Anchor

Passive anchor elements can be used in addition or as an alternative to actively actuated anchors to provide stabilization of a delivery system. Passive anchor elements can be disposed on an outer surface of the delivery system to minimize at least one of axial or radial shifting of at least one of the delivery platforms.

The construction of FIG. 38 can also be used in a passive deployment distal anchor arrangement. For example, the stabilization element 270 can comprise a shape-memory material. In one embodiment, the elongate axially oriented strips 274 are formed from a shape-memory material and are configured to be in a radially enlarged state in the absence of a circumferential constraint. This variation is delivered adjacent to or a location distal to a lesion or treatment zone in a constrained condition, e.g., with the sheath 136 over the elongate axially oriented strips 274. Relative motion between the sheath 136 and the elongate member 132B exposes the elongate axially oriented strips 274 and permits the strips to return to their radially expanded configuration. This embodiment advantageously eliminates the need for the linkage 282.

Figure 39:
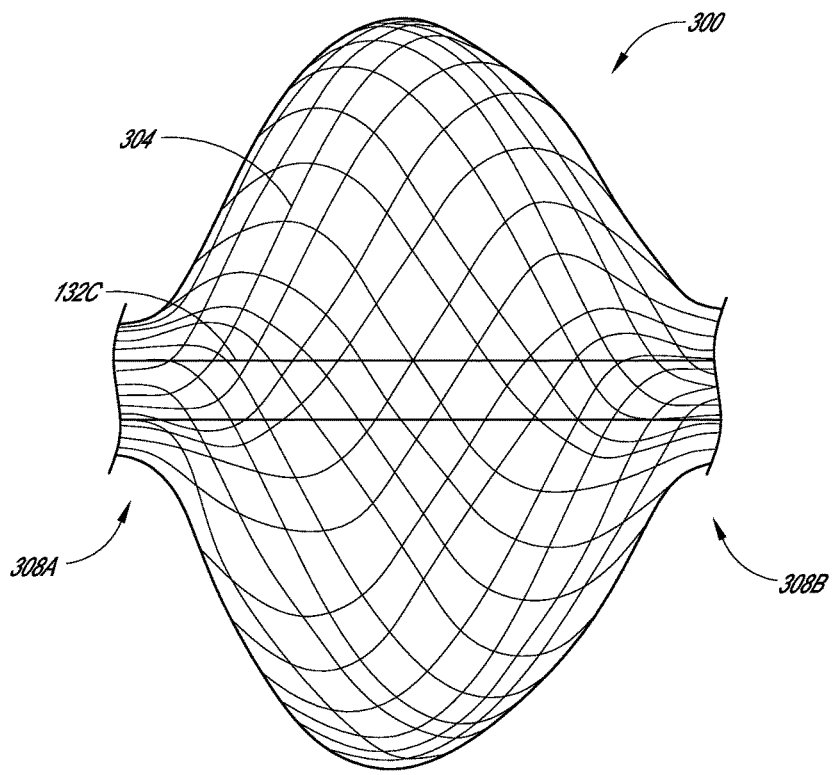
FIGS. 39-40 illustrate delivery systems with passively expanding members for stabilizing a distal delivery zone.
Figure 40:
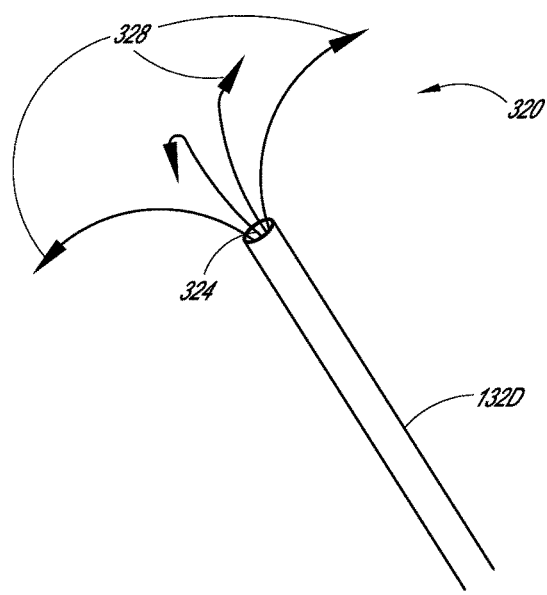

FIGS. 39-40 illustrate two passively deploying anchors that can be used in a delivery system 100C. The delivery system 100C is the same as the delivery system 100 except that with certain modifications to the elongate body 132. In particular, an elongate body 132C is provided that has a self-expanding member 300 disposed thereon. In FIG. 39, the self-expanding member 300 includes a braided structure 304 that has a proximal and distal ends 308A, 308B connected to a portion of the elongate body 132C between the distal most delivery platform 160 and the distal tip 172. The braided structure 304 can be delivered within the sheath 136 and deployed by providing relative movement between the sheath 136 and the elongate body 132C. The braided structure 304 has an expanded width in the absence of any circumferential constraint that is greater than the size of the vessel in which the system 100C is to be deployed. As a result, the passive (or self-) expansion of the braided structure 304 creates an engagement with the vessel wall. Thereafter, one or more tacks 140 can be deployed in an accurate and controlled manner.

The braided structure 304 provides the further advantage of permitting some blood flow therethrough to maintain at least some perfusion of tissues downstream of the site of anchoring. With regard to other more or fully occlusive anchors herein, lumens could be provided as an alternative way to maintain perfusion. For example, if a balloon is used to anchor a delivery system, a lumen through the balloon can be provided to perfuse downstream tissues. Perfusion may not be needed for rapid procedures.

FIG. 40 illustrates the self-expanding member 300 as including a plurality of axially extending arms 320. Each arm 320 has a proximal end 324 coupled with the elongate body 132D and a distal end 328. The elongate body 132D is shown without the tip 172, but the tip can be provided as in any of the embodiments above. Each of the arms 320 is configured to be held by the sheath 136 in a low profile configuration in which the distal end 328 of the arms 320 are adjacent to the elongate body 132D and to extend radially away from the elongate body 132D when the sheath 136 is disposed proximally of the arms 320. In the expanded position or configuration, as illustrated in FIG. 40, the distal ends of the arms are positioned to appose a body lumen. Any number of arms can be provided. The arms 320 act similar to a tri-pod to stabilize and position (e.g., centering) the elongate body 132D distal the delivery platforms 160.

Figure 41:
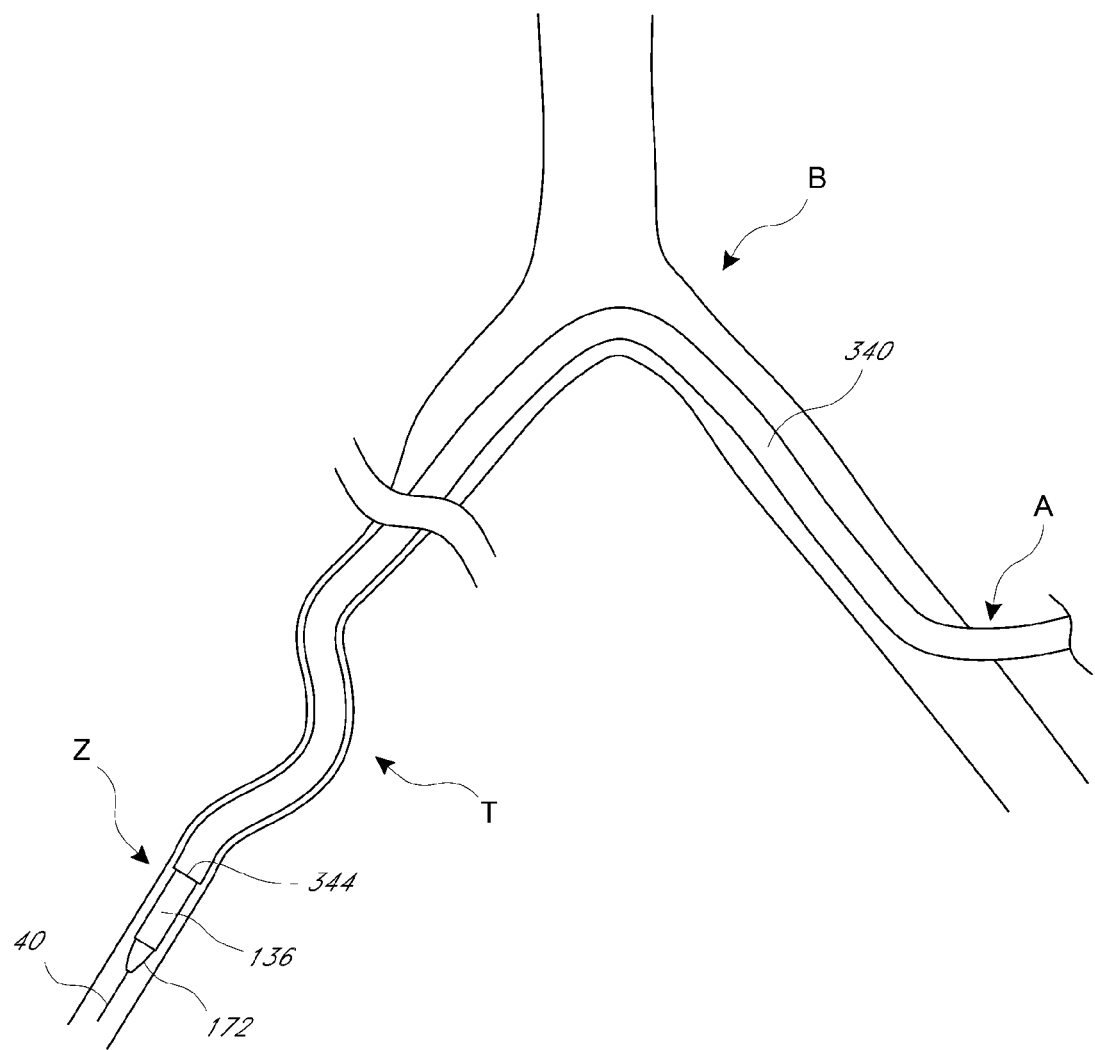
FIG. 41 illustrates a delivery system having a friction isolation sheath to stabilize a distal delivery zone.

FIG. 41 illustrates another form of passive anchoring, which involves enhancing the isolation of the delivery system 100 from friction that can result from engagement of the system with the vasculature. Such friction greatly increases when the catheter assembly 104 traverses any tortuosity in the vasculature. One technique for isolating the system 100 from friction is to provide a friction isolation sheath 340 to be disposed between the sheath 136 and the vasculature. The friction isolation sheath 340 can take any suitable form, but preferably is configured to prevent friction forces along the outer surface of the sheath 136 from causing unwanted movement of the elongate body 132 during placement of the tacks 140.

One technique for isolating the sheath 136 from friction due to tortuosity is to configure the friction isolation sheath 340 with a length sufficient to extend from a vascular access site A, such as a femoral artery, to a treatment zone. FIG. 41 illustrates that the treatment zone Z can be across the iliac bifurcation B and in or distal of the iliac artery of the leg through which vascular access was not provided. In other words, the distal end 344 of the friction isolation sheath 340 is disposed beyond the bifurcation B or other tortuosity T. Other treatment zones can be reached using the friction isolation sheath 340. The length could be sufficient to extend distally of any additional tortuosity below the iliac artery in the access or non-access leg. In other words, the distal end 344 of the friction isolation sheath 340 is disposed beyond the arch or other tortuosity. In some techniques the friction isolation sheath could be configure with enhanced lubricity on an inside surface thereof. The enhanced lubricity would reduce friction forces below a threshold to eliminate unwanted movement of the elongate body 132 due to such friction.

2. Structures and Methods for Maintaining Spacing

Tacks and other vascular devices that benefit from maintaining a pre-determined minimum spacing can be deployed with the system 100, as discussed above. For example, once stabilized, e.g., by any of the techniques described herein, minimum spacing can be provided by a variety of structures. For example, the delivery platforms 160 can assist in managing device spacing as desired. In some embodiments, the proximal marker bands 168 each project radially away from the elongate body 132 by an amount sufficient to present a distal-facing shoulder that can abut a tack 140 disposed on the delivery platform 160. The shoulder can function like a plunger providing a holding or pushing force against a proximal aspect of the tack 140. This holding or pushing force can prevent proximal migration of the tack 140 as the sheath 136 is being moved proximally relative to the elongate body 132.

Figure 42:
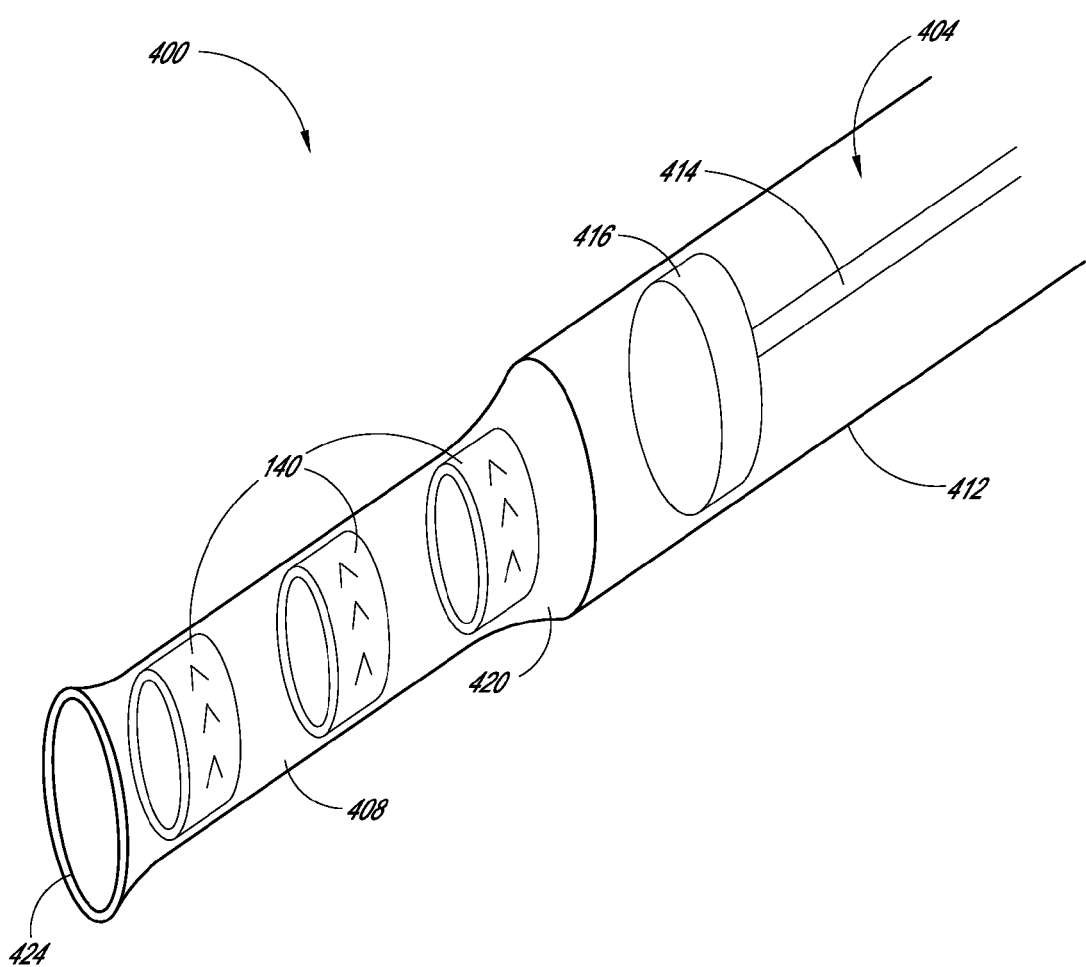
FIG. 42 illustrates a delivery system including a deployable packet for maintaining a spacing between adjacent prostheses.

FIG. 42 illustrates other embodiments in which a delivery system 400 is provided that is adapted for delivering a vascular prosthesis that includes a plurality of discrete devices. The system 400 includes an elongate body 404, an elongate packet 408, and a sheath 412. The elongate body 404 includes a distal end 414, a proximal end (not shown), and a plunger 416 disposed adjacent the distal end 414. The elongate packet 408 has a plurality of intravascular tacks 140 coupled therewith. The tacks 140 are disposed along the length of the elongate packet 408.

The sheath 412 has a proximal end (not shown) and a distal end 420 and can be positioned in a first position in which the distal end 420 of the sheath 412 is disposed distally of at least a portion of the elongate packet 408. The first position can be one in which the entirety of the packet 408 is disposed inside the sheath 412. For example, the distal end 424 of the packet 408 can be disposed inside and at or proximal of the distal end of the sheath 412. The sheath 412 can be positioned in a second position in which the distal end 420 of the sheath 412 is disposed proximally of the elongate packet 408. The second position can be achieved from the first position by proximal motion of the sheath 412 relative to the plunger 416, by distal motion of the plunger 416 relative to the sheath 412, or by simultaneous proximal motion of the sheath 420 and distal motion of the plunger 416. The plunger is moved or held stationary by applying a force to the proximal end of the elongate body 404.

The elongate packet 408 is configured to maintain a minimum spacing between adjacent tacks during deployment, e.g., during any form of movement of components of the system 400, such as those discussed above. The elongate packet 408 is also configured to permit expansion from a compressed configuration in which the elongate packet 408 is received in the sheath 412. In an expanded state, the elongate packet 408 can engage a vessel wall.

Figure 43:
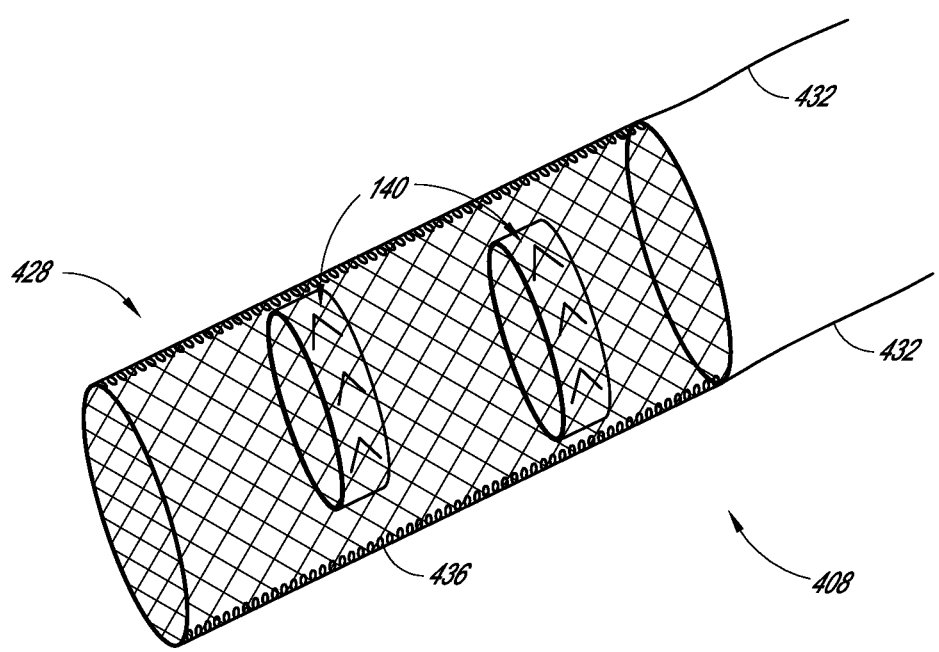
FIG. 43 illustrates one embodiment of a deployment packet adapted to maintaining a spacing between adjacent prostheses.

In various embodiments, the elongate packet 408 can be configured to release the tacks to expand toward a vessel wall after deployment. The packet 408 can be configured with an elongate sleeve 428 and a rip cord 432. The rip cord 432 preferably is coupled with the sleeve 428 such that separation of the rip cord 432 from the sleeve 428 permits the tacks 140 to expand toward a vessel wall. FIG. 43 illustrates an embodiment of the sleeve 428 that comprises a woven structure 436, which can have a high weave angle. For example, weave angles of at least about 110 degrees could be used. In this embodiment, the rip cord 432 can be configured as one or a plurality of unraveling strings. The rip cord 432 can be actuated to release the constraining force of the sleeve 428. For example, in the woven embodiments the rip cord 432 causes the sleeve to unravel so that the tacks 140 are released.

The rip cord 432 preferably would have a proximal portion coupled with an actuator at the proximal end of the corresponding delivery device. The rip cord 432 could run through a lumen (e.g., a dedicated lumen) within the delivery system and be actuatable separately from a sheath or plunger, if provided. The clinician would use such an actuator to apply a force to the rip cord 432 causing the woven structure to unravel or otherwise deploy the tacks 140.

Another embodiment can be provided in which the rip cord is eliminated. For example, the sleeve 428 can comprise a structure that weakens once immersed in blood so that shortly after deployment it passively releases the tacks 140. The sleeve 428 could comprise a bioabsorbable material or a non-reactive polymer that is left between the tacks 140 and the vasculature. The entire deployed structure, including the tacks 140 and sleeve 428 could be configured to absorb into the vasculature and to eventually disappear in the patient in certain applications. In other embodiments, the elongated packet 408 can be coated with drug elution, e.g., with the rip cord 432 bioabsorbable and the sleeve 428 remaining with the tacks to elute. As the rip cord 432 is absorbed the remaining packet 408 is pressed against the vessel wall by the expanding tacks and remains. In this alternative, the rip cord 432 can just be a region of (or one or e plurality of strands of) the woven structure 436 and not an otherwise distinct structure from the structure 436.

Figure 44:
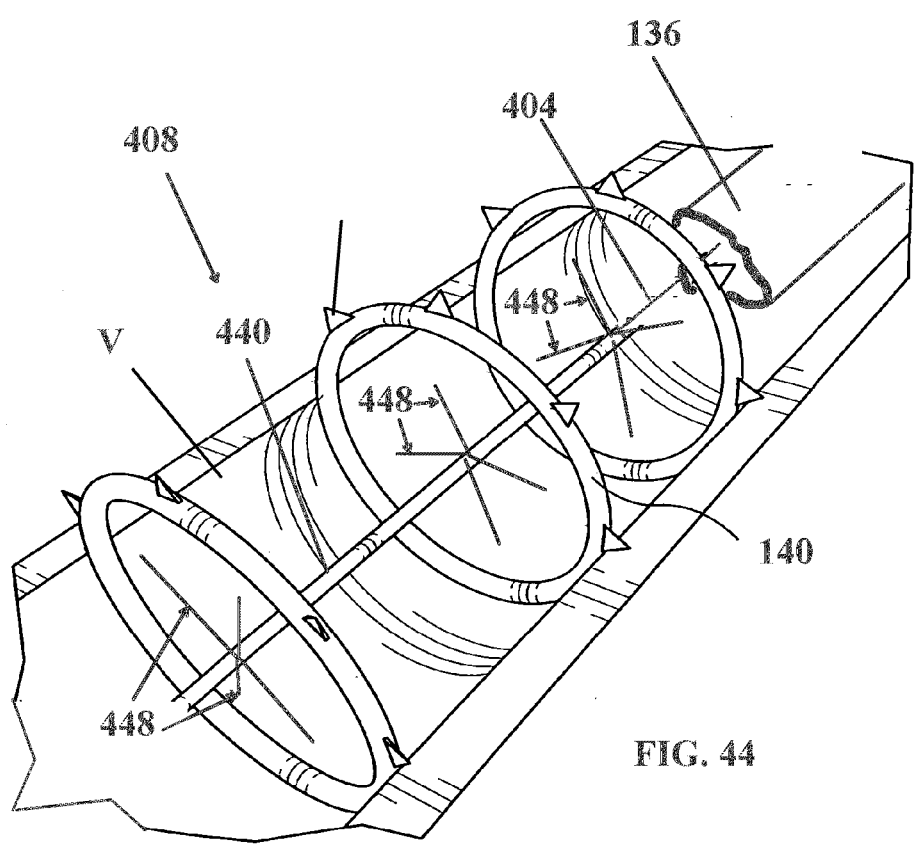
FIG. 44 illustrates a delivery system including a deployable packet for maintaining a spacing between adjacent prostheses, having a constraining element disposed inside the tacks.

In an embodiment of FIG. 44, the elongate packet 408 includes a plurality of tacks 140 and a member 440 that extends axially through a central zone of each of the tacks. The member 440 is coupled with each of the tacks 140 to restrain the tacks in a low profile configuration, in which the tack can be disposed in the sheath 136. FIG. 44 shows a plurality of tacks 140 after being separated from the elongate member 440 and after expanding into engagement with the wall of the vessel V. The elongate member 440 can be connected to the tacks 140 in any suitable fashion, such as by employing one or a plurality of radially extending member 448. The members 448 are configured to restrain expansion of the tacks 140 while the task are disposed in this sheath 136 but to break after being deployed therefrom. The breaking of the radial members 448 can be accomplished by any active mechanism, such as by cutting, untying, or actuating a rip cord, or by a passive mechanism, such as by eroding in the vasculature. After the radial member 448 separate from the tacks 140 the tacks can move away from the member 448 into a radially expanded configuration, providing a gap between the members 448 and the tacks 140.

The member 440 can then be moved out of the sheath 136 by providing relative motion between the member 404 and the sheath 136. In the illustrated embodiment, the distal end of the elongate member 404 is connected to the proximal end of the member 440 and acts as a plunger to push the packet 408 out of the sheath 136. In other embodiments, the elongate member 404 has a distal end that is small to be inserted through the tacks 140 when the tacks are in the low profile configuration. The elongate member 404 can be coupled with the distal end of the member 440 of the elongate packet 408. In this arrangement, the elongate member 404 acts on the distal end of the packet 408 rather than on the proximal end as in the embodiments of FIGS. 42-43.

In each of the embodiments of FIGS. 42-44, a pre-defined and substantially fixed axial spacing is maintained between adjacent tacks. Thus, the elongate packet provides a device spacing element capable of providing accurate separation between tacks during placement. This provides advantages such as minimizing vessel kinking, excessive metal and other issues associated with positioning tacks 140 and other vascular prostheses too close together.

3. Balloon Expansion

Figure 45:
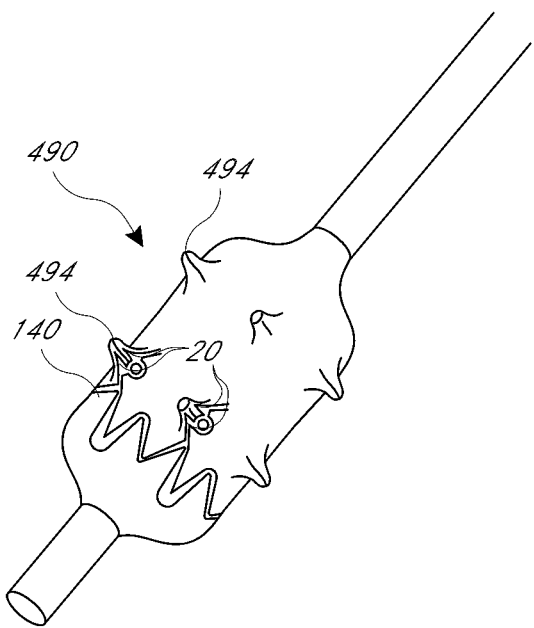
FIG. 45 illustrates a balloon that is optimized for deploying a plaque tack to induce plaque engaging rotation in a plaque anchor.

A balloon can also be used to deploy a plurality of tacks in a controlled fashion to have the correct spacing therebetween. FIG. 45 illustrates a deployment system balloon 490 having a tack 140 crimped thereon. The illustrated portion of the tack 140 is one of a plurality of repeating segments, which have mirror image counter-parts as discussed above, the other segments being omitted for clarity. The balloon 490 is for delivering and expanding the tack 140 and may be referred to as a carrier balloon. The balloon 490 can be shaped or can comprise more than one plasticity offering controlled inflation. The tack 140 and the balloon 490 are carried to the site of repair inside a sheath (not shown, but analogous to those discussed above). During deployment the balloon 490 is expanded as or after it leaves the distal end of the sheath. The expansion of the balloon 490 expands the tack 140. In one variation of this system, the balloon is used to deploy a tack 140 that can be non self-expanding or partly self-expanding. For example, the balloon 490 can be expanded to a threshold where it breaks a constraining structure disposed between the tack 140 and a sheath. The breaking of the retaining structure permits the tack 140 to expand. The balloon 490 can entirely expand the tack 140 (and using protrusions in the balloon 494, discussed more below, can raise regions of the tack for more effective anchoring), release the tack 140 to self-expand, or provide some combination of balloon and self-expansion.

Another technique for controlled placement of a tack 140 is to expand the tack under radially outwardly directed pressure, such as by expansion of a balloon. FIG. 45 illustrates the balloon 490 in an expanded state having a plaque tack 140 disposed thereon. Although a single balloon is shown, in one embodiment a balloon is incorporated into each of the delivery platforms 160 of the delivery system 100. The balloon 490 can take any suitable configuration, but preferably is configured to rotate anchors of the tack 140 into a plaque or other vascular anomaly to be held up against a vessel wall. For example, the balloon 490 can comprise a radial protrusion zone 494 disposed in an expandable section thereof. The radial protrusion zone 494 is preferably configured to rotate the anchor 20 of the tack 140 (see anchors 20 in FIG. 5C) outward of a cylindrical plane containing proximal and distal portions of the tack.

The protrusion zone 494 can have any suitable configuration, such as a plurality of discrete protrusions disposed circumferentially about the balloon 490. The protrusions can be positioned to be beneath the anchors 20 of the tacks 140, but to not extend entirely under the markers 22. The protrusions can be configured such that as the balloon 490 expands, the protrusions expand by a greater amount so that the tack 140 can be deformed from a generally cylindrical delivery shape to an arrangement where the bridges 14 rotate about an axis connecting the end points of the bridges. This rotation causes the anchors 20 to be tilted away from the center of the blood vessel and into the plaque to be tacked.

In other embodiments, the protrusion zone 494 can be a substantially continuous circumferential structure, such as a ridge that extends all the way around the balloon. Preferably in this arrangement, there is still a greater radial protrusion of the balloon in the expanded state in the location disposed radially between the anchors 20 and the longitudinal axis of the balloon.

The protrusion zone 494 is preferably at least about 0.05 mm in height. In other words, the protrusion zone 494 has a radially outermost tip or portion that is at least about 0.05 mm away from the average surface of the balloon 490 when the balloon is expanded to the diameter of the vessel in which the tack is to be placed. Or, if a plurality of protrusions is provided, a cylinder intersecting the tips of all the protrusions is preferably radially larger than the average radius of the balloon by about 0.05 mm. In other embodiments, the protrusion zone 494 is between about 0.05 mm and about 0.4 mm in height. While in other embodiments, the protrusion zone 494 is between about 0.07 mm and about 0.4 mm in height. Still further embodiments provide the protrusion zone 494 is between about 0.1 mm and about 0.2 mm in height. The balloon 490 can advantageously be paired with a tack that is not self-expanding. Standard deformable stent materials can be used, such as stainless steel. In some cases, it may be advantageous to combine a balloon expansion step with a self-expanding device. Thus, the balloon 490 can also be used in combination with self-expanding tacks. The additional height of the protrusion zone 494 can advantageously engage a feature of a tack 140 (such as an anchor 20 or a bridge 14) to prevent the tack from sliding along the axis of the balloon. In a typical balloon, a length that is not surrounded by a prosthesis will expand more than a length that is surrounded by a prosthesis, causing a "dog bone" shape when expanded. A dog bone shape balloon could induce unwanted movement of tacks mounted thereon. The protrusion zone 494 can prevent this movement by engaging the tack, as discussed above. The balloon 490 can be configured to elute a drug that is beneficial in a treatment, such as one that helps to minimize restenosis or inflammatory response.

Figure 45A:
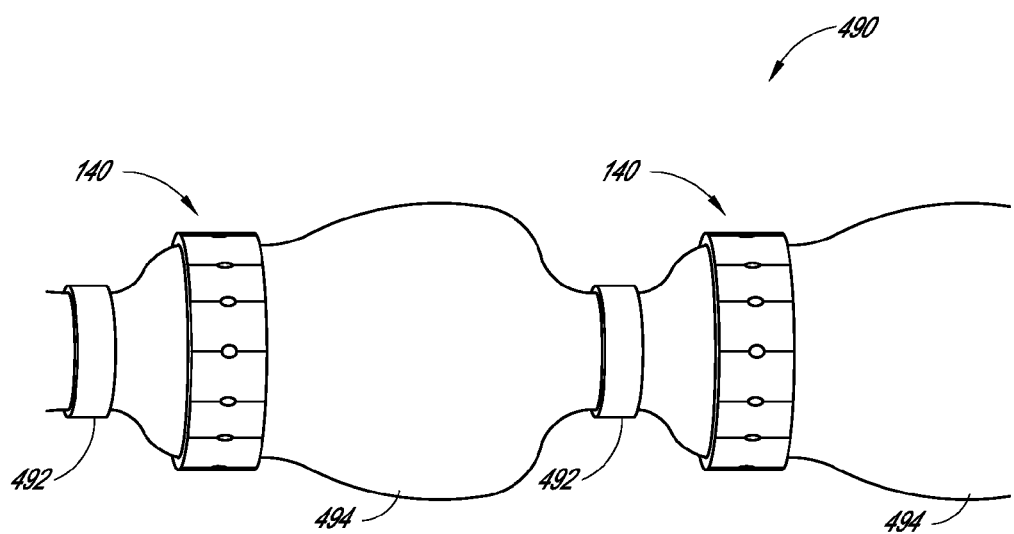
FIG. 45A shows a balloon for deploying multiple tacks.

A balloon 490 can also include a number of constraints, such as constraining bands 492, which limit expansion of the balloon to certain areas of the balloon as shown in FIG. 45A. For example, the balloon 490 can be used with a series of non-self-expanding tacks 140 spaced along the length of the balloon 490. FIG. 45A illustrates one section of such a balloon. As balloons can have a tendency to expand from one end, the constraining bands can limit this type of expansion and focus expansion at each region that includes a tack 140. Segments 494 of the balloon that do not include a tack or a constraining band can be used to ensure proper spacing between the tacks and can form a barrier between successive tacks as the balloon expands to its fully expanded position.

4. Deployment Systems

As discussed above in connection with FIGS. 4A, 32A, and 33A, a variety of tools and components can be provided for the proximal end of the delivery system 100. FIGS. 46-48D illustrate addition details of these and other embodiments of a deployment system 500 for the delivery system 100. The deployment system 500 preferably includes a housing 504 that can be held by the user and that includes a trigger device 508. The housing 504 is connected to the proximal end of the catheter assembly 104, e.g., is connected to the elongate body 132 and the sheath 136 (see FIG. 34) to impart relative motion between these two components. In certain embodiments, it is preferred that the elongate body 132 be stationary and the sheath 136 be retracted to provide relative motion. But under other circumstances, this can be reversed so that the elongate body 132 is caused to move while the sheath 136 is stationary.

In one arrangement, the housing and trigger 504, 508 comprise a single deployment ratchet handle arrangement that is manually powered. In this arrangement, each time the trigger 508 is activated, relative proximal movement of the sheath 136 would uncover one prosthesis (e.g., tack 140). The trigger 508 preferably would be spring loaded such that after being depressed it would spring back to an original position.

a. Power Assisted Deployment Devices

As discussed above, a variety of indications are advantageously treated with a plurality of discrete prostheses. For some treatments, the location of the treatment is remote from the location where the delivery system enters the vasculature or body lumen system. Both of these conditions can increase the amount of force needed to actuate the trigger 508. For such conditions and also to make deployment easier, the deployment system can include a mechanical energy source 516 to generate a force needed to provide relative movement of the sheath 136 relative to the elongate body 132. The energy source 516 can be configured to generate about the same force at the distal end of the system 100 for deployment of one tack 140 or for deployment of a plurality of tacks 140. The energy source 516 can be configured to generate a force that is constant over a stroke length that is more than two times the axial length of the tacks disposed in the system 100. In some embodiments, the energy source 516 is configured to maintain about the same rate of relative movement (e.g., sheath retraction) at the location of a distally located tack and a proximally located tack.

Figure 47:
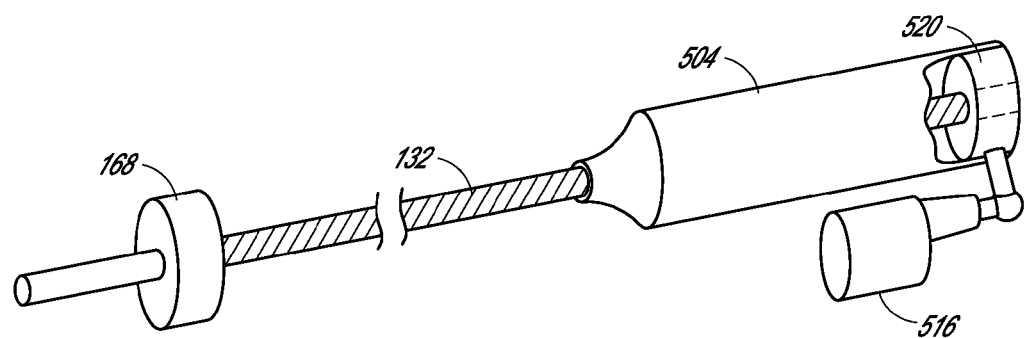

The energy source 516 can incorporate a variety of components and to impart energy or power to the system. For example in one embodiment, the energy source 516 comprises a gas cylinder that offers a controlled retraction of the sheath the required distance. The energy source 516 could be external to the housing 504, as illustrated in FIG. 47, for example, including a fluid passage connected to an external tank of gas. In one variant, the gas is contained within the housing 504 in a small vessel offering the required energy. In these embodiments, the system is not under any strain until the gas source is engaged To induce retraction of the sheath 136 relative to the elongate body 132 and marker 168, a proximal plunger 520 is coupled with the sheath 136. The plunger 520 also is arranged within the housing 504 to form a portion of an enclosed space that is in fluid communication with the gas of the energy source 516. The deployment system 500 is configured such that as a bolus of gas is delivered into this enclosed space, the plunger 520 moves proximally within the housing 504. The proximal movement produces corresponding proximal movement of the sheath 136.

The energy source 516 need not be limited to a gas cylinder. In another embodiment, a compression spring is provided that is adapted to produce a substantially constant force. Preferably the spring is arranged to provide sufficient force over a longitudinal length that is sufficient to uncover as many prostheses, e.g., tacks 140, as are desired for the treatment. This distance or stroke length can be between about 10 mm and about 200 mm (e.g., for a system carrying or operated to deploy up to 20 tacks). In certain embodiments, the stroke length is between about 8 mm and about 80 mm (e.g., for a system carrying or operated to deploy up to 10 tacks). In other embodiments, the stroke length is between about 7 mm and about 10 mm (e.g., for a system carrying or operated to deploy 1 tack). In one arrangement, the spring is tensioned prior to retraction of the sheath 136. In another embodiment, the spring is tensioned prior to use by the clinician (e.g., at the factory).

As discussed further below, it may be desirable to be able to select the number of devices to be deployed. In such circumstances, the deployment system 500 can be configured such that only a portion of the stroke of the spring is engaged. When selecting number of tacks to be deployed, the handle would automatically engage the correct length of spring and hence would supply the adequate amount of force. As discussed below in SECTION IV(A)(4)(b), a selector can be included to enable the clinician to choose a series of tacks 140 to be deployed, e.g., a subset of the full number of tacks on the delivery system to be deployed in a given deployment event.

A spring-like force can be generated by compressing gas as well. For example, a structure analogous to the plunger 520 could be urged and held distally within the handle and only released once deployment is to occur. The compressed gas would cause the plunger to be displaced proximally, along with the sheath. This effect may be considered as a form of spring recoil.

Another spring arrangement that could be employed comprises a bellows spring, which would be advantageous in designs where a longer motion is required to retract the sheath. In this arrangement the energy source 516 is adapted to act across two point of the bellows spring. The energy source could include a gas or liquid under pressure acting on one end of the bellow to actuate the motion of the bellow. As the energy spring is allowed to recoil the distance the bellow retracts is a multiplier of the distance travelled by the energy source spring. This system offers a conversion between a high force spring and a controlled long distance low force retraction.

Another option would be to employ a rotary spring driving lead screw. The spring could be pre-tensioned and connected to a lead screw. The sheath 136 would then be connected to a follower that moves as the lead screw rotates. This would allow the rotary motion provided by the spring to be converted, with adequate strength through the lead screw, to proximal (linear) movement of the sheath.

b. Selector for Multi-Prosthesis Deployment

An elongated treatment zone, which can comprise, for example, plaque or an elongate vessel flap, may be treated with a plurality of tacks 140. In certain procedures, it is possible through visualization or other surgical planning tool to know the number of tacks or prostheses needed to provide sufficient treatment. For such procedures, the deployment system 500 can include a selector 532 to determine the number of prostheses or tacks to be deployed. In one form, the selector 532 can include markings 534 on one or more of the elongate body 132 and the sheath 136. These markings can give a visual cue to the clinician holding the handle 11F, the fixture 108, or the housing 504 of how many tack have been deployed. FIG. 32A shows the markings 534 disposed on a proximal portion of the elongate body 132. Proximal movement of the sheath 136 causes the adapter 208 to pass each of a plurality of the markings 534. Each time the adapter 208 passes a marking 534, a tack 140 is exposed and can be deployed. Thus, the user can know how many tacks 140 are deployed by observing the movement of the adapter 208 over the markings 534.

FIG. 4A shows that the markings can also be placed on the handle 11F. In particular, the handle 11F is provided with a series of markings 534 that indicate how far the sheath 13 has moved. Each time the actuator 11G moves past a marking 534, another tack 140 is moved out of the sheath 13 and can be deployed.

Figure 48A:
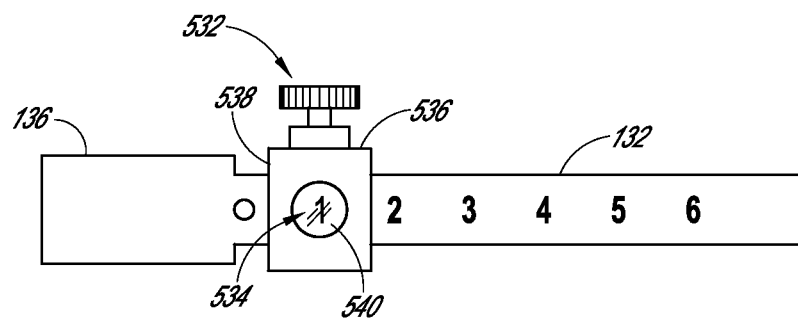

In certain embodiments, it is preferred that the selector 532 be configured to prevent conditions that would permit deployment of more than a selected number of tacks 140. In these embodiments, the selector 532 also includes a limiter 536 that prevents deployment of more than a pre-selected number of tacks. FIG. 48A shows that in one embodiment, the limiter 536 includes a slideable stop 538 that can be disposed about a proximal portion of the elongate member 132. A locking device, such as a thumb screw, is provided for immobilizing the limiter 536 on the elongate member 132. A viewable window 540 in the limiter 536 displays indicia of how many tacks will be been deployed if the sheath 136 is moved proximally into contact with the stop 538, how many remain in the system or some other useful indicator of the status of the deployment. In this case, if the limiter 536 is disposed on a proximal portion of the elongate body 132 indicating "1". This informs the clinician that when the sheath 136 sheath contacts the stop 538, one tack will be deployed.

Figure 48C:
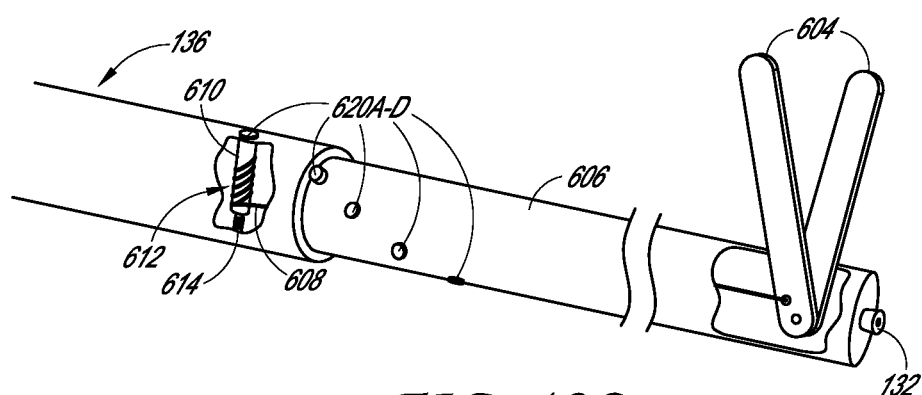
Figure 48D:
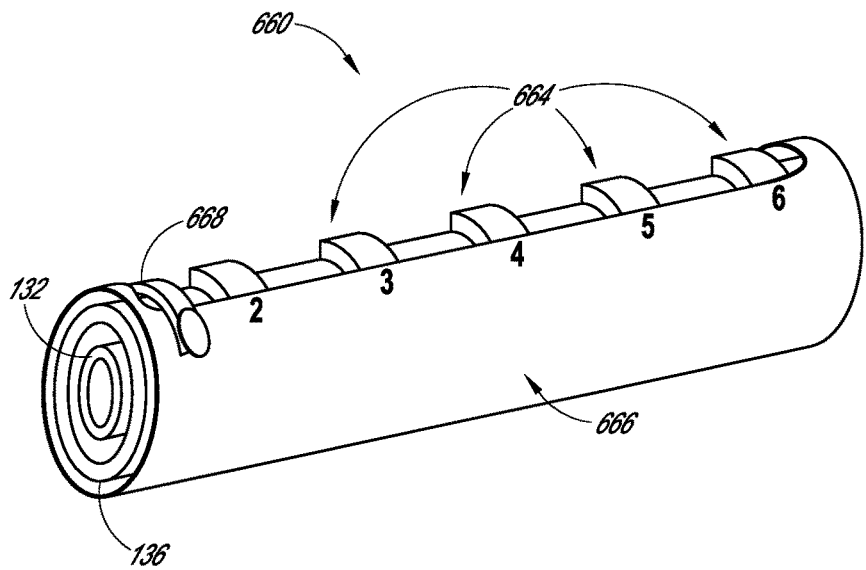
Figure 48B:
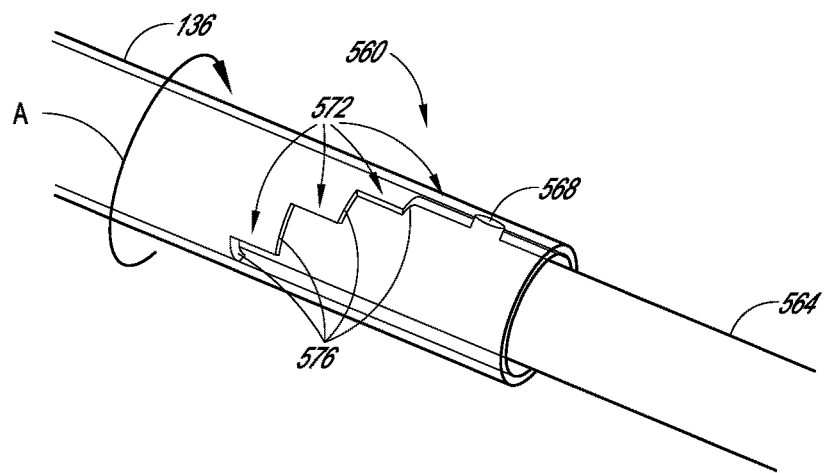

FIG. 48B illustrates another variation in which relative rotation of a proximal portion of the sleeve 136 and a selector 560 disposed within the housing 504 can enable the user to select the number of prostheses (e.g., tacks 140) to be deployed. In one variation the selector 560 includes a rod 564 that extends into the lumen formed in the sheath 136. The rod includes a pin or other radial protrusion 568 that extends outwardly into one of a plurality of notches 572 disposed on the inner surface of the sheath 136. The notches include proximal facing surfaces 576. Each notch 572 in the counter-clockwise direction as seen in the figure is progressively farther from the proximal end of the sheath 136. Each progressively farther notch 572 permits an additional increment of axial movement of the sheath 136 relative to the pin 568. Each increment of axial movement corresponding to the amount of movement needed at the distal end to expose a delivery platform 160 and corresponding tack 140. By rotating the sheath 136 relative to the pin from the position illustrated according to the arrow A, a greater number tacks can be deployed in a single stroke. Relative rotation can be provided by coupling the rod 564 with a dial and an indicator disposed on the outside of the housing 504.

In one variation of the embodiment of FIG. 48B, the selector 560 can be configured as a sleeve disposed around the sheath 136. The sheath 136 can be modified to include an outwardly protruding pin similar to the pin 568 and the sleeve can be modified to have notches. In this arrangement, the structure in FIG. 48 labeled "564" is a sheath and the structure labeled "136" is the sleeve disposed about the sheath.

Figure 46:
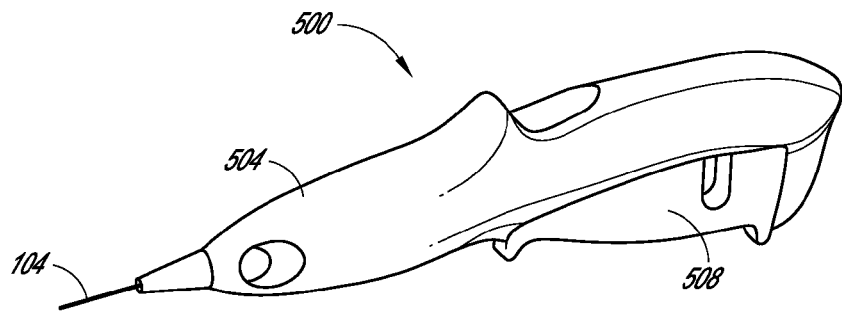
FIG. 46-48D illustrates a portion of a deployment system that can be used with any of the delivery systems disclosed herein.

FIG. 48C illustrates a deployment system 600 that can be disposed a housing similar to that illustrated in FIG. 46. The system includes both a mechanical energy source and a selector for selecting the number of tacks to be deployed. The system includes an actuator 604 coupled by a cable 608 to an energy storing device 612. The actuator 604 is mounted on a rigid body 610 that is also coupled with the elongate body 132. The energy storing device 612 can include a rotary spring driving a lead screw. More specifically, the cable 608 is wound around a barrel 610 that can rotate about the axis of a base screw 614. A spring is coupled with the barrel 610 such that as the barrel rotates to unwind the cable 608, the spring is loaded and after the tension is removed from the cable, the spring causes the barrel to rotate in the opposite direction, winding the cable back onto the barrel. The length of the cable 608 wound on the barrel is equal to or greater than the linear distance from the distal end of the distal most delivery platform 160 to the proximal end of the proximal-most delivery platform 160. The selector includes a plurality of stops 620 that are disposed proximal of the sheath 136. The stops can be activated or deactivated. A first stop 620A is located closest to the distal end of the sheath 136 and permits movement of the sheath by an amount sufficient to only deploy one tack 140. After the first tack has been deployed, the first stop 620A can be deactivated by being depressed into the rigid body 606 and a second stop 620B can be activated. The second stop permits travel of the sheath 136 a distance sufficient to expose the second-most distal delivery platform 160 and tack 140. After the second tack has been deployed, the second stop 620B can be deactivated by being depressed into the rigid body 606 and a third stop 620C can be activated. The third stop permits travel of the sheath 136 a distance sufficient to expose the third-most distal delivery platform 160 and tack 140. After the third tack has been deployed, the third stop 620C can be deactivated by being depressed into the rigid body 606 and a fourth stop 620D can be activated. The fourth stop permits travel of the sheath 136 a distance sufficient to expose the fourth-most distal delivery platform 160 and tack 140. If more than four tacks and platforms are provided, additional stops 620 can be provided. The energy stored in the energy storing device 612 causes the actuator 604 to be automatically returned to the home position for further triggering.

FIG. 48D illustrated another concept that could be used for a deployment sequence where only one tack at a time is deployed. This arrangement is similar to a bolt-action mechanism The deployment system includes a selector device 660 that has a plurality of tines 664 spaced out axially along a rigid body 666. The tines 664 provide a rigid stop structure. A moveable member 668 coupled with a proximal portion of sheath 136 can be disposed between adjacent tines 664, e.g., distal of the "2" tine 664, between the "2" and "3" tines, etc. The moveable member 668 could be disposed proximal of but adjacent to the "2" tine prior to deployment of a tack 140. An energy source driven actuator could be triggered, after which the sheath 136 and the moveable member 668 coupled thereto will slide proximally. The moveable member 668 will slide into contact with the "3" tine. This provides a hard stop and may be useful if relatively high power energy source is used. To deploy additional tacks, the moveable member 668 would be sequentially moved to the "4", "5", and "6" tines.

5. Shuttle Deployment Device

A shuttle deployment device 700 as shown in FIG. 49 can have one or more delivery platforms 160. The delivery platform 160 can include a marker band 168 at one or both ends thereof, as discussed above. A set of rails, fingers, or tines 702 can extend from one end of each marker band 168. In the illustrated embodiment there are 4 rails 702, though a greater or lesser number can be used. The rails 702 extend distally from a proximal marker band 168A. In another embodiment, the rails 702 extend proximally from a distal marker band 168B. The proximal and distal marker bands 168A, 168B are shown in FIG. 36A and can be proximal and distal sections of a single band or separate bands that are axially spaced apart. Also, only one set of rails 702 is illustrated. However, it is to be understood that in other embodiments, a set of rails 702 can be provided for each delivery platform 160. The rails 702 can have a compressed position, such as when they are within the sheath 136, and an expanded position where they are unrestrained. In the expanded position the rails can have be curved, flared, angled, or otherwise configured such that the shuttle 700 has a reduced dimension transverse to the longitudinal axis of the elongate member 132 proximally along its length.

As the sheath 136 is retracted, the rails move radially outwards towards the vascular wall to the expanded position as shown. This can center the catheter and establish a type of ramp or gradual increase in diameter to guide the positioning and expansion of the tack 140. As the tack 140 expands, it can slide down the rails into position in the vascular wall. The radial expansion of the tack 140 is thereby controlled as the struts are limited to the amount of expansion by the radial rails. The tacks 140 may be crimped around the rails 702 or may be crimped with some rails inside the tack 140 and some rails around the rails.

The shuttle device 700 can be disposed at the distal end of the elongate body 132. As illustrated, the shuttle device 700 has a plurality of gaps between the plurality of rails 702. These gaps can be used to assist in the proper positioning of the tack 140. For example, anchors, markers and/or other features of the tack 140 can project radially through the gap, such that a portion of the tack is radially between the rails and the longititudal axis of the elongate member and another portion protrudes to a radial position circumferentially between (or beyond) adjacent rails. In this position, at least a portion of the rail can be considered to be disposed radially between a portion of the tack and the longitudinal axis of the elongate member 132.

This configuration can provide many benefits such as preventing rotation and providing addition control of the placement of the tack 140 in the vasculature. The gaps can also permit anchor portions of the tack anchors 20 to connect to the vasculature at the distal end of the shuttle device 700 or rail 702.

In some embodiments, the rails 702 of the shuttle are biased to the closed position. At the same time, the tack 140 can be a self-expanding tack that biased to move to its expanded configuration. When the self-expanding tack is loaded into the shuttle these two opposed biases create stored energy within the shuttle once the sheath is in place and the two are confined in position. The bias of the tack can be greater than the bias of the rails such that the tendency to collapse is slightly less then the energy of the tacks to expand. Thus, once the sheath has been retracted from the delivery platform 160, the counteracting forces can provide a controlled expansion as the tacks leaves the distal end of the delivery catheter. This can advantageously reduce or eliminate too rapid expansion of the tack 140, which can result in unpredictable or placement.

Use of Plaque Tack after Drug Eluting Balloon Angioplasty

The use of plaque tack devices can be combined with use of drug eluting balloon (DEB) angioplasty to manage post angioplasty dissection and avoid the need for stents. In DEB angioplasty, a drug-eluting balloon or a drug coated balloon is prepared in a conventional manner. The drug may be one, or a combination, of biologically active agents that are used for various functions, such as anti-thrombotic, anti-mitotic, anti-proliferative, anti-inflammatory, stimulative of healing, or other functions. The DEB is delivered on a guidewire across an area of blockage or narrowing in the blood vessel system. The DEB is inflated to a specific pressure and for a period of time consistent with the manufactures guidelines of use for treatment purposes, as it pertains the drug coating and the intended outcomes, then the DEB is deflated and removed. At this stage the medication from the DEB has been transferred to the wall of the blood vessel. Intravascular imaging by ultrasound is then used to assess the integrity of the artery and the smoothness of the blood vessel surface at the site where the balloon was inflated. The presence of damage along the surface may be indicated as dissection, elevation of plaque, disruption of tissue, irregularity of surface. The plaque tack is used to tack down the damaged, disrupted, dissected, or irregular blood vessel surface. This permits continuation of a "stent-free" environment even if damage to the blood vessel has occurred as a result of balloon angioplasty.

At this stage the medication from the DEB has been transferred to the wall of the blood vessel. Contrast is administered into the blood vessel under fluoroscopic guidance or another method such as intravascular ultrasound is used to assess the integrity of the artery and the smoothness of the blood vessel surface at the site where the balloon was inflated. In some cases, one or more of these completion studies will demonstrate the presence of damage along the surface at the site of the balloon inflation. This damage may include dissection, elevation of plaque, disruption of tissue, irregularity of surface.

The plaque tack delivery catheter is loaded with multiple tacks that may be placed at the discretion of the operator, and advanced over a guidewire in the blood vessel to the location where the dissection or disruption or irregularity has occurred. The location is specifically and carefully identified using angiography. The plaque tack(s) is or are deployed at the location(s) of the lesion. More than one tack may be placed to tack down a major dissection. If more than one tack is placed, it may be placed only according to the rules of proper spacing of tacks. That is, the tack should be at least one tack axial length apart. After placement of the tack, it may be further expanded into the wall of the blood vessel using a standard angioplasty balloon or a drug-eluting or drug coated balloon (either as a stand alone (separate) device or integral to the delivery system). The purpose of the tack is generally not to hold the blood vessel lumen open but to tack down the non-smooth or dissected surface of the blood vessel. This "touch-up strategy" permits the resolution of the damage created by the drug-eluting or drug coated balloon without resorting to stent placement and thereby maintaining a "stent-free" environment.

As a further measure, described above, the plaque tack device itself can be used to deliver medication to the blood vessel. In addition to the delivery of medication from the anchors, the tack can be coated with medication prior to tack placement. The purpose of this activity is to permit the tack to elute biologically active agent or agents that have positive effects on the blood vessel.

One or more of the tacks deployed in accordance with the present invention may be coated with or otherwise carry a drug to be eluted over time at the deployment site. Any of a variety of therapeutically useful agents may be used, including but not limited to, for example, agents for inhibiting restenosis, inhibiting platelet aggregation, or encouraging endothelialization. Some of the suitable agents may include smooth muscle cell proliferation inhibitors such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine; antimicrobials such astriclosan, cephalosporins, aminoglycosides, and nitorfurantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promotors; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Intergrilin, abciximab), seratonin antagonist, and 5-HT uptake inhibitors; cholesterol-lowering agents; vasodilating agents; and agents which interfere with endogeneus vascoactive mechanisms. Polynucleotide sequences may also function as anti-restenosis agents, such as p15, p16, p18, p19, p21, p27, p53, p57, Rb, nFkB and E2F decoys, thymidine kinase ("TK") and combinations thereof and other agents useful for interfering with cell proliferation. The selection of an active agent can be made taking into account the desired clinical result and the nature of a particular patient's condition and contraindications. With or without the inclusion of a drug, any of the tacks disclosed herein can be made from a bioabsorbable material. Various polymeric carriers, binding systems or other coatings to permit controlled release of active agent from the tack or its coating are well known in the coronary stent arts and not reproduced herein.

In summary, the plaque tack can be used for plaque retention following balloon angioplasty treatment of atherosclerotic occlusive disease while avoiding problems with the use of stents due to installing a large mass of foreign material in the body which may cause injury, inflammation, and/or provide sites for restenosis. In contrast with stents, the plaque tack device minimizes the material structure while only being installed at one or more plaque dissection sites that require retention. The focal elevating elements on the tack periphery minimizes the contact surface area of the plaque tack with the blood vessel walls and reduces the risk of causing plaque dissection or injury to the blood vessel walls. This approach offers clinicians the ability to perform a minimally invasive post-angioplasty treatment and produce a stent-like result without using a stent.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, it is contemplated that various aspects and features of the invention described can be practiced separately, combined together, or substituted for one another, and that a variety of combination and sub-combinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. A system for delivering a vascular prosthesis, comprising:
    an elongate body comprising a proximal end, a distal end, and a plurality of delivery platforms disposed adjacent the distal end, each of the delivery platforms comprising a recess having a fixed axial length and defined between an axially fixed cylindrical protrusion having a proximal annular shoulder and an axially fixed cylindrical protrusion having a distal annular shoulder, the proximal and distal shoulders having corresponding radially extending faces perpendicular to a longitudinal axis of the elongate body to prevent proximal and distal slippage of an intravascular tack along the elongate body, wherein the axially fixed cylindrical protrusion having a proximal annular shoulder and the axially fixed cylindrical protrusion having a distal annular shoulder comprise a constant axial diameter;
    a sheath having a proximal end and a distal end, the sheath being moveable relative to the elongate body from a first position in which the distal end of the sheath is disposed distally of a distal-most delivery platform to a second position in which the distal end of the sheath is disposed proximally of at least the distal-most delivery platform; and
    a plurality of self-expanding intravascular tacks, each intravascular tack of the plurality of intravascular tacks having a single column of cells with a series of radiopaque markers, wherein each cell is defined by both a proximal-most ring and a distal-most ring of the tack, and being disposed about a corresponding delivery platform and a distal end of a proximal intravascular tack of the plurality of intravascular tacks being spaced away a distance from a proximal end of an adjacent-most distal intravascular tack of the plurality of intravascular tacks, the distance being greater than half of a length of each of the intravascular tacks of the plurality of intravascular tacks;
    wherein the system is configured to separately place at least the proximal tack and the distal tack at a treatment zone one at a time at spaced apart locations such that a gap is provided in the treatment zone between the distal end of the proximal tack and the proximal end of the distal tack;
    and wherein radial expansion force drops from no more than about 2 Newtons at 3 mm diameter to no more than about 1 Newton at 6 mm diameter.

2. The system of claim 1, further comprising a stabilization device disposed on an outer surface of the system configured to minimize at least one of axial or radial shifting of at least one of the delivery platforms along or away from a longitudinal axis of a blood vessel in which the tacks are to be deployed.

3. The system of claim 2, wherein the stabilization device is disposed between the distal end of the elongate body and at least one of the delivery platforms, the stabilization device adapted to directly engage a plurality of locations disposed about a body lumen to minimize movement of the elongate body relative to the body lumen when relative movement is provided between the sheath and the elongate body.

4. The system of claim 2, wherein the stabilization device comprises an expandable balloon having a cylindrical configuration.

5. The system of claim 2, wherein the stabilization device comprises a self-expanding member.

6. The system of claim 5, wherein the self-expanding member comprises a plurality of axially extending arms, each arm having a proximal end coupled with the elongate body and a distal end, each of the arms configured to be held by the sheath in a low profile configuration in which the distal end of the arms are adjacent to the elongate body and to extend radially away from the elongate body when the sheath is disposed proximally of the arms such that the distal ends of the arms are positioned to appose a body lumen.

7. The system of claim 1, wherein the system includes between 3 and 20 tacks disposed on corresponding delivery platforms.

8. The system of claim 1, wherein the sheath is a first sheath and further comprising:
a second sheath disposed about the first sheath, the second sheath being configured to prevent friction forces along the outer surface of the first sheath from causing unwanted movement of the elongate body during placement of the tacks.

9. The system of claim 8, wherein the system has a pre-deployment configuration in which the first sheath is fully inserted into the second sheath, and wherein, in the pre-deployment configuration, at least one intravascular tack is disposed distal of the distal end of the second sheath.

10. The system of claim 1, further comprising a hand-held trigger device connected to the proximal end of at least one of the elongate body and the sheath to cause retraction of the distal end of the sheath relative to the elongate body to expose the delivery platforms to permit the tacks to be deployed.

11. The system of claim 10, wherein the hand-held trigger comprises a selector to set an increment of movement of the sheath corresponding to a number of tacks to be deployed.

12. The system of claim 1, wherein the distance the distal end of the proximal tack is spaced away from the proximal end of the adjacent-most distal tack is greater than the length of each of the intravascular tacks.

13. The system of claim 1, wherein the length of each of the intravascular tacks is 15 mm or less.

14. The system of claim 13, wherein the length of each of the intravascular tacks is 8 mm or less.

15. The system of claim 14, wherein the distance the distal end of the proximal tack is spaced away from the proximal end of the adjacent-most distal tack is at least 5 mm.

16. The system of claim 14, wherein the distance the distal end of the proximal tack is spaced away from the proximal end of the adjacent-most distal tack is between 6 and 10 mm.

17. The system of claim 13, wherein the length of each of the intravascular tacks is 6 mm or less.

18. The system of claim 1, wherein the series of radiopaque markers are positioned along a midline of the tack.

19. The system of claim 1 wherein the axially fixed cylindrical protrusion having a proximal annular shoulder comprises an annular marker band.

20. The system of claim 1 wherein the axially fixed cylindrical protrusion having a distal annular shoulder comprises an annular marker band.

21. A system for delivering a vascular prosthesis, comprising:
an elongate body extending along a longitudinal axis between a proximal end and a distal end, the elongate body comprising:
a plurality of annular recesses disposed adjacent the distal end;
a plurality of proximal shoulders;
a plurality of distal shoulders, each of the annular recess situated between one of the plurality of proximal shoulders and one of the plurality of distal shoulders, each shoulder of the pluralities of proximal and distal shoulders having a radially extending face perpendicular to the longitudinal axis; and
a plurality of axially fixed cylindrical regions, each axially fixed cylindrical region formed by a proximal shoulder at an adjacent first annular recess of the plurality of annular recesses and a distal shoulder at an adjacent second annular recess of the plurality of annular recesses, each axially fixed cylindrical region having an outer diameter greater than an outer diameter of the adjacent first and second annular recesses, being non-expandable, and comprising an annular radiopaque marker band;
a sheath having a proximal end, a distal end, the sheath being moveable relative to the elongate body from a first position in which the distal end of the sheath is disposed distally of a distal-most annular recess of the plurality of annular recesses to a second position in which the distal end of the sheath is disposed proximally of at least the distal-most annular recess; and
a plurality of self expanding intravascular tacks, each intravascular tack having no more than a single column of cells with a series of radiopaque markers, wherein each cell is defined by both a proximal-most ring and a distal-most ring of the tack, and being disposed about a corresponding annular recess of the plurality of annular recesses and therefore between corresponding proximal and distal shoulders with corresponding radially extending faces perpendicular to the longitudinal axis to prevent proximal and distal slippage of the intravascular tack along the elongate body; and
wherein radial expansion force drops from no more than about 2 Newtons at 3 mm diameter to no more than about 1 Newton at 6 mm diameter.

22. The system of claim 21, wherein each intravascular tack disposed about a corresponding delivery platform such that a distal end of a proximal intravascular tack is a spaced away a distance from a proximal end of an adjacent-most distal intravascular tack, the distance being greater than half of a length of each of the intravascular tacks.

23. The system of claim 22, wherein the distance the distal end of the proximal tack is spaced away from the proximal end of the adjacent-most distal tack is greater than the length of each of the intravascular tacks.

24. The system of claim 21, further comprising a stabilization device disposed on an outer surface of the system configured to minimize at least one of axial or radial shifting of at least one of the plurality of annular recesses along or away from a longitudinal axis of a blood vessel in which the intravascular tacks are to be deployed.

25. The system of claim 24, wherein the stabilization device is disposed between the distal end of the elongate body and at least one of the annular recesses, the stabilization device adapted to directly engage a plurality of locations disposed about a body lumen to minimize movement of the elongate body relative to the body lumen when relative movement is provided between the sheath and the elongate body.

26. The system of claim 21, wherein the system includes between 3 and 20 intravascular tacks disposed on corresponding annular recesses.

27. The system of claim 21, wherein the sheath is a first sheath and further comprising:
   a second sheath disposed about the first sheath, the second sheath being configured to prevent friction forces along the outer surface of the first sheath from causing unwanted movement of the elongate body during placement of the intravascular tacks.

28. The system of claim 21, further comprising a handheld trigger device connected to the proximal end of at least one of the elongate body and the sheath to cause retraction of the distal end of the sheath relative to the elongate body to expose the annular recesses to permit the intravascular tacks to be deployed.

29. The system of claim 21, wherein the series of radiopaque markers are positioned along a midline of the tack.

* * * * *